US007148406B2

(12) United States Patent
Helentjaris et al.

(10) Patent No.: US 7,148,406 B2
(45) Date of Patent: Dec. 12, 2006

(54) GENES ENCODING ENZYMES FOR LIGNIN BIOSYNTHESIS AND USES THEREOF

(75) Inventors: Timothy G. Helentjaris, Ankeny, IA (US); Benjamin A. Bowen, Berkeley, CA (US); Xun Wang, San Diego, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 83 days.

(21) Appl. No.: 10/361,460

(22) Filed: Feb. 10, 2003

(65) Prior Publication Data

US 2003/0163839 A1 Aug. 28, 2003

Related U.S. Application Data

(63) Continuation of application No. 09/076,851, filed on May 12, 1998, now abandoned.

(60) Provisional application No. 60/057,082, filed on Aug. 27, 1997.

(51) Int. Cl.
  C12N 15/29 (2006.01)
  C12N 15/82 (2006.01)
  C12N 15/87 (2006.01)
  C12N 5/04 (2006.01)
  A01H 5/00 (2006.01)
(52) U.S. Cl. .................. 800/298; 800/320.1; 536/23.6; 435/320.1; 435/410; 435/419
(58) Field of Classification Search ............... 536/23.1, 536/23.6, 24.1; 800/278, 298, 320.1; 435/468, 435/419, 320.1, 410
See application file for complete search history.

(56) References Cited

U.S. PATENT DOCUMENTS

| | | | |
|---|---|---|---|
| 5,451,514 A | 9/1995 | Boudet et al. | |
| 5,538,880 A | 7/1996 | Lundquist et al. | |
| 5,728,570 A | 3/1998 | Matern et al. | |
| 5,850,020 A | 12/1998 | Bloksberg et al. | |
| 5,952,486 A | 9/1999 | Bloksberg et al. | |
| 5,959,178 A | 9/1999 | Fritig et al. | |
| 5,981,837 A | 11/1999 | Chapple | |
| 6,005,167 A | 12/1999 | Van Tunen et al. | |
| 6,015,943 A | 1/2000 | Boudet et al. | |
| 6,066,780 A | 5/2000 | Boudet et al. | |
| 6,087,557 A | 7/2000 | Clausen et al. | |
| 6,114,601 A | 9/2000 | Kikuchi et al. | |
| 6,204,434 B1 | 3/2001 | Bloksberg et al. | |
| 6,251,951 B1 | 6/2001 | Emerson et al. | |

FOREIGN PATENT DOCUMENTS

| | | |
|---|---|---|
| EP | 0 359 617 A2 | 3/1990 |
| EP | 1 000 543 A1 | 5/2000 |
| WO | WO 89/12059 A1 | 12/1989 |
| WO | WO 89/12230 A1 | 12/1989 |
| WO | WO 93/05159 A1 | 3/1993 |
| WO | WO 93/05180 A1 | 3/1993 |
| WO | WO 97/12982 A1 | 4/1997 |
| WO | WO 97/23599 A2 | 7/1997 |
| WO | WO 97/45549 A1 | 12/1997 |
| WO | WO 98/03535 A1 | 1/1998 |
| WO | WO 98/11205 A2 | 3/1998 |
| WO | WO 98/41642 A1 | 9/1998 |
| WO | WO 99/24561 A2 | 5/1999 |
| WO | WO 99/24561 A3 | 5/1999 |
| WO | WO 99/31243 A1 | 6/1999 |
| WO | WO 99/37788 A2 | 7/1999 |

OTHER PUBLICATIONS

Kajita et al (1997, Plant Science 128:109-118).*
Reinold et al (1993, Plant Physiol. 101:373-383).*
Bowie et al, Science 247:1306-1310, 1990.*
McConnell et al, Nature 411 (6838):709-713, 2001.*
Fourgoux-Nicol et al (1999, Plant Molecular Biology 40:857-872).*
Hotze et al (1995, FEBS Lett. 374(3):345-350).*
Uhlmann et al., Molecular Cloning and Expression of 4-Coumarate:Coenzyme A Ligase, an Enzyme Involved in the Resistance Response of Soybean (Glycine max L.) against Pathogen Attack, Plant Physiol. (1993) 102: 1147-1156.
Akashi et al., Cloning of cytochrome P450 cDNAs from cultured Glycyrrhiza echinata L. cells and their transcriptional activation by elicitor-treatment, Plant Science (1997) 126:39-47.
Hotze et al., Cinnamata 4-hydroxylase from Catharanthus roseus, and a strategy for the functional expression of plant cytochrome P450 proteins as translational fusions with P450 reductase in *Escherichia coli*, FEBS Letters (1995) 374:345-350.
Kiedrowski et al., Rapid activation of a novel plant defense gene is strictly dependent on the Arabidopsis RPM1 disease resistance locus, EMBO Journal (1992) 11(13):4677-4684.
Meyer et al., Ferulate-5-hydroxylase from Arabidopsis thaliana defines a new family of cytochrome P450-dependent monooxygenases. Proc. Natl. Acad. Sci. USA (1996) 93:6869-6874.
Mizutani et al., Molecular Cloning ans Sequencing of a cDNA Encoding Mung Bean Cytochrome P450 (P450C4H) Possessing Cinnamate 4-Hydroxylase Activity. Biochemical and Biophysical Research Communications (1993) 190(3):875-880.
Campbell, W., Populus tremuloides caffeoyl-CoA 3-O-methyltransferase mRNA, complete cds, Database EMBL/Genbank/DDBJ Accession No. U27118 (1995).
Lafayette et al., Liriodendron tulipifera high-pI laccasse (LAC2-4) mRNA, complete cds, Database EMBL/Genbank/DDBJ Accession No. U73106 (1996).

(Continued)

Primary Examiner—Stuart F. Baum
(74) Attorney, Agent, or Firm—Kathryn K. Lappegard; Pioneer Hi-Bred International, Inc.

(57) ABSTRACT

The present invention provides methods and compositions relating to altering lignin biosynthesis content and/or composition of plants. The invention provides isolated nucleic acids and their encoded proteins which are involved in lignin biosynthesis. The invention further provides recombinant expression cassettes, host cells, transgenic plants, and antibody compositions.

9 Claims, No Drawings

OTHER PUBLICATIONS

Sasaki et al., Rice cDNA, partial sequence, Database EMBL/Genbank/DDBJ Accession No. D42011 (1994).

Baysdorfer et al., zEST00832 maize leaf, Stratagene #937005 *Zea mays* cDNA clone csuh00832 5' end, Database EMBL/Genbank/DDBJ Accession No. W21750 (1996).

Civardi et al., *Zea mays* mRNA for cinnamyl CoA reductase, Database EMBL/Genbank/DDBJ Accession No. Y13734 (1997).

Lozoya et al., Primary structures And catalytic properties of isoenzymes encoded by the two 4-coumarate:CoA ligase genes in parsley, Eur. J. Biochem. (1998): 176-661-667.

Voo et al., 4-Coumarate:Coenzyme A Ligase from Lobiolty Pine Xylem (Isolation, Characterization, and Complementary DNA Cloning), Plant Physiol. (1995) 108:85-97.

Lee et al., Two Divergent Members of a Tobacco 4-Coumarate:Coenzyme A Ligase (4CL) Gene Family (cDNA Structure, Gene Inheritance and Expression, and Properties of Recombinant Proteins), Plant Physiol. (1996) 112:193-205.

Kajita et al., Immunological characterization of transgenic tobacco plants with a chimeric gene for 4-coumarate:CoA ligase that have altered lignin in their xylem tissue, Plant Science (1997) 128:109-118.

Brodelius et al., Isolation and characterization of a cDNA from cell suspension cultures of Vanilla planifolia encoding 4-coumarate:coenzyme A ligase, Plant Physiol. Biochem. (1997) 35(7):497-506.

Teutsch et al., Isolation and sequence of a cDNA encoding the Jerusalem artichoke cinnamate 4-hydroxylase, a major plant cytochrome P450 Involved in the general phenylpropanoid pathway, Proc. Natl. Acad. Sci. USA (1993) 90:4102-4106.

Mizutani et al., Isolation of a cDNA and a Genomic Clone Enxoding Cinnamate 4-Hydroxylase from Arabidopsis and Its Expression Manner in Planta, Plant Physiol. (1997) 113:755-763.

Bell-Lelong et al., Cinnamate-4-Hydroxylase Expression in Arabidopsis, Plant Physiol. (1997) 113:729-738.

Sewalt et al., Reduced Lignin Content and Altered Lignin Composition in Transgenic Tobacco Down-Regulated in Expression of L-Phenytalanine Ammonia-Lyase or Cinnamate 4-Hydroxylase, Plant Physiol. (1997) 115:41-50.

Kajita et al., Alterations in the Biosynthesis of Lignin in Transgenic Plants with Chimeric Genes for 4-Coumarate:Coenzyme A Ligase, Plant Cell Physiol. (1996) 37(7):957-965.

Kajita et al., Structural Characterization of Modified Lignin in Transgenic Tobacco Plants in Which the Activity of 4-Coumarate:Coenzyme A Ligase Is Depressed, Plant Physiol. (1997) 114:871-879.

Lee et al., Antisense Suppression of 4-Coumarate:Coenzyme A Ligase Activity in Arabidopsis Leads to Altered Lignin Subunit Composition, Plant Cell (1997) 9:1985-1998.

Huang et al., Chromosomal localization of parsely 4-coumarate:CoA ligase genes by in situ hybridization with a complementary DNA, Plant Cell Reports (1989) 8:59-62.

Boudet et al., Lignin genetic engineering, Molecular Breeding (1996) 2:25-39.

Lacombe et al., Cinnamoyl CoA reductase, the first committed enzyme of the lignin branch biosynthetic pathway; cloning, expression and phiogenetic relationships, Plant Journal (1997) 11(3):429-441.

Collazo et al., Structure and expression of the lignin O-methyltransferase gene from *Zea mays* L., Plant Mol. Biol. (1992) 20:857-867.

Ni et al., Reduced lignin in transgenic plants containing a caffeic acid O-methyltransferase antisense gene, Transgenic Research (1994) 3:120-126.

Ye et al., Differential expression of two O-Methyltransferases in Lignin Biosynthesis in Zinnia elegans, Plant Physiol. (1995) 108:459-467.

Vignols et al., The brown midrib3 (bm3) Mutation in Maize Occurs in the Gene Encoding Caffeic Acid O-Methyltransferase, Plant Cell (1995) 7:407-416.

Capellades et al., The maize caffeic acid O-methyltransferase gene promoter is active in transgenic tobacco and maize plant tissues, Plant. Mol. Biol. (1996) 31:307-322.

Morrow et al., Molecular characterization of a brown modrib3 deletion mutation in maize, Molecular Breeding (1997) 3:351-357.

Sewalt et al., Lignin Impact on Fiber Degradation: Increased Enzymatic Digestibility of Genetically Engineered Tobacco (Nicotiana Tabacum) Stems Reduced in Lignin Content, J. Agric. Food Chem. (1997) 45:1977-1983.

Walter et al., Cinnamyl-alcohol dehydrogenase, a molecular marker specific for lignin synthesis: cDNA cloning and mRNA induction by fungal elicitor, Proc. Natl. Acad. Sci. USA (1988) 85:5546-5550.

Knight et al., Identification and characterisation of cDNA clones encoding cinnamyl alcohol dehydrogenase from tobacco, Plant Mol. Biol. (1992) 19:793-801.

Hibino et al., Cinnamyl Alcohol Dehydrogenase from Aralia cordata: Cloning of the cDNA and Expression of the Gene in Lignified Tissues, Plant Cell Physiol. (1993) 34(5):659-665.

Grima-Pettanati et al., Molecular cloning and expression of a Eucalyptus gunnii cDNA clone encoding cinnamyl alcohol dehydrogenase, Plant Mol. Biol. (1993) 21:1085-1095.

Galliano et al., Molecular cloning, sequence analysis and elicitor-*l*ozone-induced accumulation of cinnamyl alcohol dehydrogenase from Norway spruce (*Picea abies* L.), Plant Mol. Biol. (1993) 23:145-156.

Halpin et al., Manipulation of Lignin quality by downregulation of cinnamyl alcohol dehydrogenase, Plant Journal (1994) 6(3):339-350.

Higuchi et al., Red-brown color of lignified tissues of transgenic plants with antisense CAD gene: Wine-red lignin from coniferyl aldehyde, Journal of Biotechnology (1994) 37:151-158.

Boudet et al., Tansley Review No. 80: Biochemistry and molecular biology of lignification, New Phytol. (1995) 129:203-236.

Hibino et al., Increase of Cinnamaldehyde Groups in Lignin of Transgenic Tobacco Plants Carrying an Antisense Gene for Cinnarmyl Alcohol Dehydrogenase, Biosci. Biotech. Biochem. (1995) 59(5):929-931.

Feuillet et al., Tissue- and cell-specific expression of cinnamyl alcohol dehydrogenase promoter in transgenic poplar plants, Plant Mol. Biol. (1995) 27:651-667.

Bernard-Vialhe et al., Cell Wall Degradability of Transgenic Tobacco Stems in Relation to Their Chemical Extraction and Lignin Quality, J. Agric. Food Chem. (1996) 44:1164-1169.

Sato et al., Changes in the Activity and mRNA of Cinnamyl Alcohol Dehydrogenase during Tracheary Element Differentiation in Zinnia, Plant Physiol. (1997) 113:425-430.

Baucher et al., Red Xylem and higher Lignin Extractability by Down-Regulating a Cinnamyl Alcohol Dehydrogenase in Poplar, Plant Physiol. 91996) 112:1479-1490.

Mackay et al., Inheritance, gene expression, and lignin characterization in a mutant pine deficient in cinnamyl alcohol dehydrogenase, Proc. Natl. Acad. Sci. USA (1997) 94:8255-8260.

Schmitt et al., Molecular Cloning, Induction, and Taxonomic Distribution of Caffeoyl-CoA 3-O-Methyltransferase, an Enzyme Involved in Disease Resistance, J. Biol. Chem. (1991) 266(26):17416-17423.

Ye et al., An Alternative Methylation Pathway inLignin Biosynthesis in Zinnia, Plant Cell (1994) 6:1427-1439.

Busam et al., Isolation of Tobacco cDNAs Encoding Caffeoyl-CoA 3-O-Methyltransferase (Accession Nos. Z56282 and Z82982), Plant Gene Register PGR 97-039, Plant Physiol (1997) 113:1003.

Grimmig et al., Structure of the parsley caffeoyl-CoA O-methyltransferase gene, harbouring a novel elicitor responsive cis-acting element, Plant Mol. Biol. (1997) 33:323-341.

Zhang et al., Molecular characterization of a cDNA encoding caffeoyl-coenzyme A 3-O-methyltransferase of Stellaria longipes, J. Biosci. (1997) 22(2):161-176.

Dixon et al., Metabolic engineering: prospects for crop improvement through the genetic manipulation of phenylpropanoid biosynthesis and defense responses—a review, Gene (1996) 179:61-71.

Gordon-Kamm et al., Transformation of Maize Cells and Regeneration of Fertile Transgenic Plants, Plant Cell (1990) 2:603-618.

Reinold et al., Tobacco and Parsley 4-Coumarate:Coenzyme A Ligase Genes Are Temporally and Spatially Regulated in a Cell Type-Specific Manner during Tobacco Flower Development, Plant Physiol. (1993) 101:373-383.

Hu et al., Repression of lignin biosynthesis promotes cellulose accumulation and growth in transgenic trees, Nature Biotechnology (1999) 17:808-812.

Burgess et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue, J. Cell Biology (1990) 111:2129-2138.

Bowie et al., Deciphering the Message in Protein Sequences: Tolerance to Amino Acid Substitutions, Science (1990) 247:1306-1310.

Zhao et al., Oryza sativa 4-coumarata:CoA isoform 2(4cl.2) mRNA, complete cds., NCBI Accession No. L43362 (1995).

* cited by examiner

SEQUENCE LISTING

<160> NUMBER OF SEQ ID NOS: 85

<210> SEQ ID NO 1
<211> LENGTH: 559
<212> TYPE: PRT
<213> ORGANISM: Zea mays

<400> SEQUENCE: 1

Met Gly Asp Ala Ala Ile Ala Ala Val His Leu His Glu Ser Glu Glu
 1               5                  10                  15

Glu His Ile Phe Arg Ser Arg Phe Pro Pro Val Ala Val Pro Asp Asp
            20                  25                  30

Val Thr Val Pro Glu Phe Val Leu Ala Asp Ala Glu Ala Tyr Ala Asp
        35                  40                  45

Lys Thr Ala Leu Val Glu Ala Ala Pro Gly Gly Arg Ser Tyr Thr Tyr

```
                    50                  55                  60
Gly Glu Leu Val Arg Asp Val Ala Arg Phe Ala Arg Ala Leu Arg Ser
 65                      70                  75                  80

Ile Gly Val Arg Arg Gly His Val Val Val Ala Leu Pro Asn Leu
                 85                  90                  95

Ala Val Tyr Pro Val Val Ser Leu Gly Ile Met Ser Ala Gly Ala Val
             100                 105                 110

Phe Ser Gly Val Asn Pro Arg Ala Val Ala Ala Glu Ile Lys Lys Gln
             115                 120                 125

Val Glu Asp Ser Glu Ala Arg Leu Val Val Ala Asp Ala Val Ala Tyr
130                 135                 140

Asp Lys Val Lys Asp Ala Gly Val Pro Val Ile Gly Ile Gly Asp Val
145                 150                 155                 160

Ala Arg Leu Pro Gly Ala Ile Gly Trp Asp Glu Leu Leu Ala Met Ala
                 165                 170                 175

Asp Arg Ala Gly Ala Pro Val Val Ala Leu Glu Pro Ala Gln Gln Ser
             180                 185                 190

Asp Leu Cys Ala Leu Pro Tyr Ser Ser Gly Thr Thr Gly Val Ser Lys
             195                 200                 205

Gly Val Met Leu Ser His Arg Asn Leu Val Ser Ser Leu Cys Ser Ser
210                 215                 220

Met Phe Ala Val Gly Gln Glu Leu Val Gly Gln Val Val Thr Leu Gly
225                 230                 235                 240

Leu Met Pro Phe Phe His Ile Tyr Gly Ile Thr Gly Ile Cys Cys Ala
                 245                 250                 255

Thr Leu Arg His Lys Gly Thr Val Val Met Asp Arg Phe Asp Leu
             260                 265                 270

Arg Ala Phe Leu Gly Ala Leu Leu Thr His Arg Val Met Phe Ala Pro
             275                 280                 285

Val Val Pro Pro Val Met Leu Ala Met Val Lys Ser Pro Val Ala Asp
                 290                 295                 300

Glu Phe Asp Leu Ser Gly Leu Ala Leu Arg Ser Val Met Thr Ala Ala
305                 310                 315                 320

Ala Pro Leu Ala Pro Asp Leu Leu Ala Ala Phe Glu Arg Lys Phe Pro
                 325                 330                 335

Gly Val Gln Val Glu Glu Ala Tyr Gly Leu Thr Glu His Ser Cys Ile
             340                 345                 350

Thr Leu Thr His Ala Ser Gly Gly Glu Asp Val Gly Ser Ala Val
             355                 360                 365

Gln Val Ala Lys Lys Ser Val Gly Phe Ile Leu Pro Asn Leu Glu
370                 375                 380

Val Lys Phe Val Asp Pro Asp Thr Gly Arg Ser Leu Pro Lys Asn Thr
385                 390                 395                 400

Pro Gly Glu Ile Cys Val Arg Ser Gln Ala Val Met Gln Gly Tyr Tyr
                 405                 410                 415

Arg Lys Lys Glu Glu Thr Glu Arg Thr Ile Asp Ala Ala Gly Trp Leu
             420                 425                 430

His Thr Gly Asp Val Gly Tyr Ile Asp Asp Gly Asp Val Phe Ile
             435                 440                 445

Val Asp Arg Ile Lys Glu Leu Ile Lys Tyr Lys Gly Phe Gln Val Ala
         450                 455                 460

Pro Ala Glu Leu Glu Ala Ile Leu Leu Ser His Pro Ser Val Glu Asp
465                 470                 475                 480
```

```
Ala Ala Val Phe Gly Leu Pro Asp Glu Glu Ala Gly Glu Val Pro Ala
            485                 490                 495

Ser Cys Val Val Arg Arg Gly Ala Pro Glu Ser Glu Ala Asp Met
        500                 505                 510

Met Ala Tyr Val Ala Gly Arg Val Ala Ser Tyr Lys Lys Leu Arg Leu
            515                 520                 525

Leu Arg Phe Val Asp Ala Ile Pro Lys Ser Val Ser Gly Lys Ile Leu
            530                 535                 540

Arg Arg Gln Leu Arg Asp Glu Phe Val Lys Lys Thr Ala Ala Ala
545                 550                 555
```

<210> SEQ ID NO 2
<211> LENGTH: 555
<212> TYPE: PRT
<213> ORGANISM: Zea mays

<400> SEQUENCE: 2

```
Met Gly Ser Val Asp Ala Ala Ile Ala Val Pro Val Pro Ala Ala Glu
 1               5                  10                  15

Glu Lys Ala Val Glu Lys Ala Met Val Phe Arg Ser Lys Leu Pro
            20                  25                  30

Asp Ile Glu Ile Asp Ser Ser Met Ala Leu His Thr Tyr Cys Phe Gly
            35                  40                  45

Lys Met Gly Glu Val Ala Glu Arg Ala Cys Leu Ile Asp Gly Leu Thr
        50                  55                  60

Gly Ala Ser Tyr Thr Tyr Ala Glu Val Glu Ser Leu Ser Arg Arg Ala
65                  70                  75                  80

Ala Ser Gly Leu Arg Ala Met Gly Val Gly Lys Gly Asp Val Val Met
                85                  90                  95

Ser Leu Leu Arg Asn Cys Pro Glu Phe Ala Phe Thr Phe Leu Gly Ala
            100                 105                 110

Ala Arg Leu Gly Ala Ala Thr Thr Thr Ala Asn Pro Phe Tyr Thr Pro
            115                 120                 125

His Glu Val His Arg Gln Ala Glu Ala Ala Gly Ala Arg Leu Ile Val
        130                 135                 140

Thr Glu Ala Cys Ala Val Glu Lys Val Arg Glu Phe Ala Ala Glu Arg
145                 150                 155                 160

Gly Ile Pro Val Val Thr Val Asp Gly Arg Phe Asp Gly Cys Val Glu
                165                 170                 175

Phe Ala Glu Leu Ile Ala Ala Glu Glu Leu Glu Ala Asp Ala Asp Ile
            180                 185                 190

His Pro Asp Asp Val Val Ala Leu Pro Tyr Ser Ser Gly Thr Thr Gly
        195                 200                 205

Leu Pro Lys Gly Val Met Leu Thr His Arg Ser Leu Ile Thr Ser Val
210                 215                 220

Ala Gln Gln Val Asp Gly Glu Asn Pro Asn Leu Tyr Phe Arg Lys Asp
225                 230                 235                 240

Asp Val Val Leu Cys Leu Leu Pro Leu Phe His Ile Tyr Ser Leu Asn
                245                 250                 255

Ser Val Leu Leu Ala Gly Leu Arg Ala Gly Ser Thr Ile Val Ile Met
            260                 265                 270

Arg Lys Phe Asp Leu Gly Ala Leu Val Asp Leu Val Arg Arg Tyr Val
        275                 280                 285

Ile Thr Ile Ala Pro Phe Val Pro Pro Ile Val Val Glu Ile Ala Lys
```

```
                  290                 295                 300
Ser Pro Arg Val Thr Ala Gly Asp Leu Ala Ser Ile Arg Met Val Met
305                 310                 315                 320

Ser Gly Ala Ala Pro Met Gly Lys Glu Leu Gln Asp Ala Phe Met Ala
                325                 330                 335

Lys Ile Pro Asn Ala Val Leu Gly Gln Gly Tyr Gly Met Thr Glu Ala
                340                 345                 350

Gly Pro Val Leu Ala Met Cys Leu Ala Phe Ala Lys Glu Pro Tyr Pro
                355                 360                 365

Val Lys Ser Gly Ser Cys Gly Thr Val Val Arg Asn Ala Glu Leu Lys
370                 375                 380

Ile Val Asp Pro Asp Thr Gly Ala Ala Leu Gly Arg Asn Gln Pro Gly
385                 390                 395                 400

Glu Ile Cys Ile Arg Gly Glu Gln Ile Met Lys Gly Tyr Leu Asn Asp
                405                 410                 415

Pro Glu Ser Thr Lys Asn Thr Ile Asp Lys Asp Gly Trp Leu His Thr
                420                 425                 430

Gly Asp Ile Gly Tyr Val Asp Asp Asp Glu Ile Phe Ile Val Asp
                435                 440                 445

Arg Leu Lys Glu Ile Ile Lys Tyr Lys Gly Phe Gln Val Pro Pro Ala
450                 455                 460

Glu Leu Glu Ala Leu Leu Ile Thr His Pro Glu Ile Lys Asp Ala Ala
465                 470                 475                 480

Val Val Ser Met Asn Asp Asp Leu Ala Gly Glu Ile Pro Val Ala Phe
                485                 490                 495

Ile Val Arg Thr Glu Gly Ser Gln Val Thr Glu Asp Glu Ile Lys Gln
                500                 505                 510

Phe Val Ala Lys Glu Val Val Phe Tyr Lys Lys Ile His Lys Val Phe
                515                 520                 525

Phe Thr Glu Ser Ile Pro Lys Asn Pro Ser Gly Lys Ile Leu Arg Lys
                530                 535                 540

Asp Leu Arg Ala Arg Leu Ala Ala Gly Val Gln
545                 550                 555

<210> SEQ ID NO 3
<211> LENGTH: 575
<212> TYPE: PRT
<213> ORGANISM: Zea mays

<400> SEQUENCE: 3

Met Ile Thr Val Ala Ala Pro Glu Ala Gln Pro Gln Val Ala Ala
  1                 5                  10                  15

Ala Ala Val Ala Ala Pro Glu Glu Thr Val Phe Arg Ser Lys Leu Pro
                 20                  25                  30

Asp Ile Asp Ile Pro Thr His Leu Pro Leu His Asp Tyr Cys Phe Ser
                 35                  40                  45

Arg Ala Ala Glu Ala Ala Gly Ala Pro Cys Leu Ile Ala Ala Ala Thr
             50                  55                  60

Gly Arg Thr Tyr Thr Tyr Ala Glu Thr Arg Leu Leu Cys Arg Lys Ala
 65                  70                  75                  80

Ala Ala Cys Leu His Gly Leu Gly Val Ala Gln Gly Asp Arg Val Met
                 85                  90                  95

Leu Leu Leu Gln Asn Ser Val Glu Phe Val Leu Ala Phe Phe Gly Ala
                100                 105                 110
```

```
Ser Phe Leu Gly Ala Val Thr Ala Ala Asn Pro Phe Cys Thr Pro
        115                 120                 125

Gln Glu Ile His Lys Gln Phe Ser Ala Ser Gly Ala Lys Val Val
130                 135                 140

Thr His Ser Ala Tyr Val Ala Lys Leu Arg His Gly Ala Phe Pro Arg
145                 150                 155                 160

Ile Gly Thr Val Ser Gly Gly Val Asp Gly Asn Ala Leu Leu Thr
                    165                 170                 175

Val Leu Thr Ile Asp Gly Asp Ala Ala Asp Thr Pro Glu Gly Cys Leu
                180                 185                 190

Ala Phe Trp Glu Leu Leu Thr Ser Gly Asp Gly Asp Ala Leu Pro Glu
        195                 200                 205

Val Ser Ile Ser Pro Asp Asp Pro Val Ala Leu Pro Phe Ser Ser Gly
210                 215                 220

Thr Thr Gly Leu Pro Lys Gly Val Val Leu Thr His Gly Gly Gln Val
225                 230                 235                 240

Thr Asn Val Ala Gln Gln Val Asp Gly Ala Asn Pro Asn Leu Tyr Met
                245                 250                 255

Arg Glu Gly Asp Val Ala Leu Cys Val Leu Pro Leu Phe His Ile Phe
            260                 265                 270

Ser Leu Asn Ser Val Leu Leu Cys Ala Met Arg Ala Gly Ala Ala Val
        275                 280                 285

Met Leu Met Pro Lys Phe Glu Met Gly Ala Met Leu Glu Gly Ile Gln
290                 295                 300

Arg Trp Arg Val Thr Val Ala Ala Val Val Pro Pro Leu Val Leu Ala
305                 310                 315                 320

Leu Ala Lys Asn Pro Ala Leu Glu Lys Tyr Asp Leu Ser Ser Ile Arg
                325                 330                 335

Ile Val Leu Ser Gly Ala Ala Pro Leu Gly Lys Asp Leu Val Asp Ala
            340                 345                 350

Leu Arg Ala Arg Val Pro Gln Ala Val Phe Gly Gln Gly Tyr Gly Met
        355                 360                 365

Thr Glu Ala Gly Pro Val Leu Ser Met Cys Pro Ala Phe Ala Lys Glu
        370                 375                 380

Pro Ala Pro Ala Lys Pro Gly Ser Cys Gly Thr Val Val Arg Asn Ala
385                 390                 395                 400

Glu Leu Lys Val Val Asp Pro Asp Thr Gly Leu Ser Leu Gly Arg Asn
                405                 410                 415

Leu Pro Gly Glu Ile Cys Ile Arg Gly Pro Gln Ile Met Lys Gly Tyr
            420                 425                 430

Leu Asn Asp Pro Glu Ala Thr Ala Arg Thr Ile Asp Val His Gly Trp
        435                 440                 445

Leu His Thr Gly Asp Ile Gly Tyr Val Asp Asp Asp Glu Val Phe
450                 455                 460

Ile Val Asp Arg Val Lys Glu Leu Ile Lys Phe Lys Gly Phe Gln Val
465                 470                 475                 480

Pro Pro Ala Glu Leu Glu Ala Leu Leu Val Ala His Pro Ser Ile Ala
                485                 490                 495

Asp Ala Ala Val Val Pro Gln Lys Asp Glu Ala Ala Gly Glu Val Pro
            500                 505                 510

Val Ala Phe Val Val Arg Ala Ala Asp Ala Asp Ile Ala Glu Asp Ala
        515                 520                 525

Ile Lys Glu Phe Ile Ser Lys Gln Val Val Leu Tyr Lys Arg Ile His
```

```
                530                 535                 540
Lys Val Tyr Phe Thr Pro Ser Ile Pro Lys Ser Ala Ser Gly Lys Ile
545                 550                 555                 560

Leu Arg Arg Glu Leu Arg Ala Lys Leu Ala Ala Ala Thr Ala
                565                 570                 575

<210> SEQ ID NO 4
<211> LENGTH: 354
<212> TYPE: PRT
<213> ORGANISM: Zea mays

<400> SEQUENCE: 4

Met Ala Thr Ala Ile Val Pro Thr Asp Ala Glu Leu Leu Gln Ala Gln
1               5                   10                  15

Ala Asp Leu Trp Arg His Ser Leu Tyr Tyr Leu Thr Ser Met Ala Leu
                20                  25                  30

Lys Cys Ala Val Glu Leu His Ile Pro Thr Ala Ile His Asn Leu Gly
            35                  40                  45

Gly Ser Ala Thr Leu Pro Asp Leu Val Ala Ala Leu Ser Leu Pro Ala
        50                  55                  60

Ala Lys Leu Pro Phe Leu Gly Arg Val Met Arg Leu Leu Val Thr Ser
65                  70                  75                  80

Gly Val Phe Ala Ser Ser Asp Val Gln Tyr Arg Leu Asn Pro Leu
                85                  90                  95

Ser Trp Leu Leu Val Glu Gly Val Glu Ser Glu Asp His Thr Tyr Gln
                100                 105                 110

Lys Tyr Phe Val Leu Gly Thr Val Ser Arg His Tyr Val Glu Ala Gly
            115                 120                 125

Met Ser Leu Ala Asp Trp Phe Lys Lys Glu Glu Asp Glu Asp Arg Gln
        130                 135                 140

Leu Pro Ser Pro Phe Glu Ala Leu His Gly Val Pro Leu Val His Glu
145                 150                 155                 160

Ser Thr Lys Leu Leu Asp Glu Glu Leu Asp Arg Val Val Glu Glu Gly
                165                 170                 175

Val Ala Ala His Asp Asn Leu Ala Ile Gly Thr Val Ile Arg Glu Cys
            180                 185                 190

Gly Ala Asp Val Phe Ser Gly Leu Arg Ser Leu Thr Tyr Cys Cys Gly
        195                 200                 205

Arg Gln Gly Asn Ala Ser Ala Ala Ala Ile Val Lys Ala Phe Pro Asp
210                 215                 220

Ile Lys Cys Thr Val Leu Asn Leu Pro Arg Val Val Glu Glu Thr Thr
225                 230                 235                 240

Thr Lys Thr Ile Thr Ile Pro Pro Ala Gln Ala Val Met Leu Lys Leu
                245                 250                 255

Val Leu His Phe Trp Ser Asp Asp Cys Val Lys Ile Leu Glu Leu
            260                 265                 270

Cys Arg Lys Ala Ile Pro Ser Arg Gln Glu Gly Gly Lys Val Ile Ile
        275                 280                 285

Ile Glu Ile Leu Leu Gly Pro Tyr Met Gly Pro Val Met Tyr Glu Ala
290                 295                 300

Gln Leu Leu Met Asp Met Leu Met Val Asn Thr Lys Gly Arg Gln
305                 310                 315                 320

Arg Gly Glu Asp Asp Trp Arg His Ile Phe Thr Lys Ala Gly Phe Ser
                325                 330                 335
```

```
Asp Tyr Lys Val Val Lys Lys Ile Gly Ala Arg Gly Val Ile Glu Val
            340                 345                 350
Tyr Pro
```

<210> SEQ ID NO 5
<211> LENGTH: 375
<212> TYPE: PRT
<213> ORGANISM: Zea mays

<400> SEQUENCE: 5

```
Met Ala Leu Met Gln Glu Ser Ser Gln Asp Leu Leu Gln Ala His
 1               5                  10                  15

Asp Glu Leu Leu His His Ser Leu Cys Phe Ala Lys Ser Leu Ala Leu
             20                  25                  30

Ala Val Ala Leu Asp Leu Arg Ile Pro Asp Ala Ile His His Gly
         35                  40                  45

Ala Gly Gly Ala Thr Leu Leu Gln Ile Leu Ala Glu Thr Ala Leu His
     50                  55                  60

Pro Ser Lys Leu Arg Ala Leu Arg Arg Leu Met Arg Val Leu Thr Val
65                  70                  75                  80

Thr Gly Ile Phe Ser Val Val Glu Gln Pro Ala Gly Gly Gly Asp
             85                  90                  95

Asp Ser Thr Val His Thr Ser Asp Asp Glu Ala Val Val Tyr Arg
             100                 105                 110

Leu Thr Ala Ala Ser Arg Phe Leu Val Ser Asp Asp Val Ser Thr Ala
         115                 120                 125

Thr Leu Ala Pro Phe Val Ser Leu Ala Leu Gln Pro Ile Ala Ala Cys
     130                 135                 140

Pro His Ala Leu Gly Ile Ser Ala Trp Phe Arg Gln Glu Gln His Glu
145                 150                 155                 160

Pro Ser Pro Tyr Gly Leu Ala Phe Arg Gln Thr Pro Thr Ile Trp Glu
                165                 170                 175

His Ala Asp Asp Val Asn Ala Leu Leu Asn Lys Gly Met Ala Ala Asp
            180                 185                 190

Ser Arg Phe Leu Met Pro Ile Val Leu Arg Glu Cys Gly Glu Thr Phe
        195                 200                 205

Arg Gly Ile Asp Ser Leu Val Asp Val Gly Gly His Gly Gly Ala
    210                 215                 220

Ala Ala Ile Ala Ala Ala Phe Pro His Leu Lys Cys Ser Val Leu
225                 230                 235                 240

Asp Leu Pro His Val Val Ala Gly Ala Pro Ser Asp Gly Asn Val Gln
                245                 250                 255

Phe Val Ala Gly Asn Met Phe Glu Ser Ile Pro Pro Ala Thr Ala Val
            260                 265                 270

Phe Leu Lys Lys Thr Leu His Asp Trp Gly Asp Glu Cys Val Lys
        275                 280                 285

Ile Leu Lys Asn Cys Lys Gln Ala Ile Ser Pro Arg Asp Ala Gly Gly
    290                 295                 300

Lys Val Ile Ile Leu Asp Val Val Gly Tyr Lys Gln Ser Asn Ile
305                 310                 315                 320

Lys His Gln Glu Thr Gln Val Met Phe Asp Leu Tyr Met Met Ala Val
                325                 330                 335

Asn Gly Val Glu Arg Asp Glu Gln Glu Trp Lys Lys Ile Phe Thr Glu
            340                 345                 350
```

```
Ala Gly Phe Lys Asp Tyr Lys Ile Leu Pro Val Ile Gly Asp Val Ser
        355                 360                 365

Val Ile Ile Glu Val Tyr Pro
370                 375

<210> SEQ ID NO 6
<211> LENGTH: 370
<212> TYPE: PRT
<213> ORGANISM: Zea mays

<400> SEQUENCE: 6

Met Ala Leu Met Gln Glu Ser Ser Gln Asp Gln Asp Met Leu Gln
 1                5                  10                  15

Ala His Asp Glu Leu Leu His His Ser Leu Cys Phe Ala Lys Ser Leu
            20                  25                  30

Ala Leu Thr Val Ala Leu Asp Leu Arg Ile Pro Asp Ala Ile His His
            35                  40                  45

His Gly Gly Gly Ala Thr Leu Leu Gln Ile Leu Ala Glu Thr Gly Leu
 50                  55                  60

His Pro Ser Lys Leu Arg Ala Leu Arg Arg Leu Met Arg Val Leu Thr
65                   70                  75                  80

Val Thr Gly Thr Phe Ser Val Gln Val Gln Gln Pro Pro Ala Gly Ser
                    85                  90                  95

Asp Asp Asp Glu Ala Val Val Tyr Arg Leu Thr Ala Ala Ser Arg
                100                 105                 110

Phe Leu Val Ser Asp Glu Val Ser Thr Ala Thr Thr Leu Ala Pro Phe
            115                 120                 125

Val Ser Leu Ala Leu Gln Pro Ile Ala Ala Ser Pro His Ala Leu Gly
130                 135                 140

Ile Cys Ala Trp Phe Arg Gln Glu Gln His Glu Pro Ser Pro Tyr Gly
145                 150                 155                 160

Leu Ala Phe Arg Gln Thr Pro Thr Leu Trp Glu His Ala Asp Asp Val
                165                 170                 175

Asn Ala Leu Leu Asn Lys Gly Met Val Ala Asp Ser Arg Phe Leu Met
            180                 185                 190

Pro Ile Val Leu Arg Gln Cys Gly Glu Met Phe Arg Gly Ile Asn Ser
            195                 200                 205

Leu Val Asp Val Gly Gly Gly His Gly Gly Ala Ala Ala Ile Ala
210                 215                 220

Ala Ala Phe Pro His Val Lys Cys Ser Val Leu Asp Leu Pro His Val
225                 230                 235                 240

Val Ala Gly Ala Pro Ser Asp Gly Asn Val Gln Phe Val Ala Gly Asn
                245                 250                 255

Met Phe Glu Ser Ile Pro Pro Ala Thr Ala Val Phe Leu Lys Lys Thr
            260                 265                 270

Leu His Asp Trp Gly Asp Glu Cys Val Lys Ile Leu Lys Asn Cys
            275                 280                 285

Lys Gln Ala Ile Pro Pro Arg Asp Ala Gly Gly Lys Val Ile Ile Leu
290                 295                 300

Asp Val Val Gly Tyr Lys Gln Ser Asn Ile Lys His Gln Glu Thr
305                 310                 315                 320

Gln Val Met Phe Asp Leu Tyr Met Met Ala Val Asn Gly Val Glu Arg
                325                 330                 335

Asp Glu Gln Glu Trp Lys Lys Ile Phe Ala Glu Ala Gly Phe Lys Asp
            340                 345                 350
```

Tyr Lys Ile Leu Pro Val Ile Gly Asp Val Ser Val Ile Glu Val
        355                 360                 365
Tyr Pro
    370

<210> SEQ ID NO 7
<211> LENGTH: 366
<212> TYPE: PRT
<213> ORGANISM: Zea mays

<400> SEQUENCE: 7

Met Ala Leu Met Gln Glu Ser Ser Gln Asp Leu Leu Glu Ala His Asp
 1               5                  10                  15

Glu Leu Phe His His Cys Leu Cys Phe Ala Lys Ser Leu Ala Leu Ala
            20                  25                  30

Val Ala Gln Asp Leu Arg Ile Pro Asp Ala Ile His His Gly Gly
        35                  40                  45

Gly Ala Thr Leu His Gln Ile Leu Ala Glu Ala Ala Leu His Pro Ser
    50                  55                  60

Lys Leu Arg Ala Leu Arg Arg Leu Met Arg Val Leu Thr Val Ser Gly
65                  70                  75                  80

Val Phe Thr Val Gln Tyr Ser Ser Thr Val Asp Ala Ser Asp Gly Ala
                85                  90                  95

Asp Val Val Tyr Arg Leu Thr Ala Ala Ser Arg Phe Leu Val Ser Asp
            100                 105                 110

Ser Asp Glu Ala Gly Thr Ala Ser Leu Ala Pro Phe Ala Asn Leu Ala
        115                 120                 125

Leu His Pro Ile Ala Ile Ser Pro His Ala Val Gly Ile Cys Ala Trp
    130                 135                 140

Phe Arg Gln Glu Gln His Asp Pro Ser Pro Tyr Gly Leu Ala Phe Arg
145                 150                 155                 160

Gln Ile Pro Thr Ile Trp Glu His Ala Asp Asn Val Asn Ala Leu Leu
                165                 170                 175

Asn Lys Gly Leu Leu Ala Glu Ser Arg Phe Leu Met Pro Ile Val Leu
            180                 185                 190

Arg Glu Cys Gly Asp Glu Val Phe Arg Gly Ile Asp Ser Leu Val Asp
        195                 200                 205

Val Gly Gly Gly His Gly Gly Ala Ala Thr Ile Ala Ala Ala Phe
    210                 215                 220

Pro His Val Lys Cys Ser Val Leu Asp Leu Pro His Val Val Ala Gly
225                 230                 235                 240

Ala Pro Ser Asp Ala Cys Val Gln Phe Val Ala Gly Asn Met Phe His
                245                 250                 255

Ser Ile Pro Pro Ala Thr Ala Val Phe Phe Lys Thr Thr Leu Cys Asp
            260                 265                 270

Trp Gly Asp Asp Glu Cys Ile Lys Ile Leu Lys Asn Cys Lys Gln Ala
        275                 280                 285

Ile Ser Pro Arg Asp Glu Gly Gly Lys Val Ile Ile Met Asp Val Val
    290                 295                 300

Val Gly Tyr Gly Gln Ser Asn Met Lys Arg Leu Glu Thr Gln Val Met
305                 310                 315                 320

Phe Asp Leu Val Met Met Ala Val Asn Gly Val Glu Arg Asp Glu Gln
                325                 330                 335

Glu Trp Lys Glu Met Phe Ile Glu Ala Gly Phe Lys Asp Tyr Lys Ile

```
                  340             345             350
Arg Pro Val Ala Gly Leu Met Ser Val Ile Glu Val Tyr Pro
            355             360             365

<210> SEQ ID NO 8
<211> LENGTH: 505
<212> TYPE: PRT
<213> ORGANISM: Zea mays
<220> FEATURE:
<221> NAME/KEY: VARIANT
<222> LOCATION: (1)...(505)
<223> OTHER INFORMATION: Xaa = Any Amino Acid

<400> SEQUENCE: 8

Met Val Leu Leu Phe Val Glu Lys Leu Leu Val Gly Leu Leu Ala Ser
 1               5                  10                  15

Val Met Val Ala Ile Ala Val Ser Lys Ile Arg Gly Arg Lys Leu Arg
            20                  25                  30

Leu Pro Pro Gly Pro Val Pro Val Pro Val Phe Gly Asn Trp Leu Gln
        35                  40                  45

Val Gly Asp Asp Leu Asn His Arg Asn Leu Ala Ala Leu Ser Arg Lys
50                  55                  60

Phe Gly Asp Val Phe Leu Leu Arg Met Gly Gln Arg Asn Leu Val Val
65                  70                  75                  80

Val Ser Ser Pro Pro Leu Ala Arg Glu Val Leu His Thr Gln Gly Val
                85                  90                  95

Glu Phe Gly Ser Arg Thr Arg Asn Val Val Phe Asp Ile Phe Thr Asp
            100                 105                 110

Lys Gly Gln Asp Met Val Phe Thr Val Tyr Gly Asp His Trp Arg Lys
        115                 120                 125

Met Arg Arg Ile Met Thr Val Pro Phe Phe Thr Asn Lys Val Val Gln
    130                 135                 140

Gln Tyr Arg His Gly Trp Glu Ala Glu Ala Ala Val Val Asp Asp
145                 150                 155                 160

Val Arg Leu Asp Pro Lys Ala Ala Thr Asp Gly Ile Val Leu Arg Arg
                165                 170                 175

Arg Leu Gln Leu Met Met Tyr Asn Asn Val Tyr Arg Ile Met Phe Asp
            180                 185                 190

Arg Arg Phe Glu Ser Met Asp Asp Pro Leu Phe Leu Arg Leu Arg Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Arg
225                 230                 235                 240

Val Cys Lys Glu Val Lys Glu Thr Arg Leu Lys Leu Phe Lys Asp Phe
                245                 250                 255

Phe Leu Glu Glu Arg Lys Lys Leu Ala Ser Thr Lys Ala Thr Asp Ser
            260                 265                 270

Asn Gly Leu Lys Cys Ala Ile Asp His Ile Leu Glu Ala Gln Gln Lys
        275                 280                 285

Gly Glu Ile Asn Glu Asp Asn Val Leu Phe Ile Val Glu Asn Ile Asn
    290                 295                 300

Val Ala Ala Ile Glu Thr Thr Leu Trp Ser Ile Glu Trp Ala Val Ala
305                 310                 315                 320

Glu Leu Val Asn His Pro Glu Ile Gln Gln Lys Leu Arg Gln Glu Leu
                325                 330                 335
```

-continued

Asp Thr Val Leu Gly Pro Gly His Gln Ile Thr Glu Pro Asp Thr His
            340                 345                 350

Asn Leu Pro Tyr Leu Gln Ala Val Ile Lys Glu Thr Leu Arg Leu Arg
            355                 360                 365

Met Ala Ile Pro Leu Leu Val Pro His Met Asn Leu His Asp Ala Lys
        370                 375                 380

Leu Gly Xaa Tyr Asp Ile Pro Ala Glu Ser Lys Ile Leu Val Asn Ala
385                 390                 395                 400

Trp Tyr Leu Ala Asn Asn Pro Asp Xaa Trp Arg Arg Pro Glu Glu Phe
                405                 410                 415

Arg Pro Glu Arg Phe Xaa Glu Glu Lys His Val Glu Ala Asn Gly
            420                 425                 430

Asn Asp Phe Arg Tyr Leu Pro Phe Gly Val Gly Arg Arg Ser Cys Pro
            435                 440                 445

Gly Ile Ile Leu Ala Leu Pro Ile Leu Gly Ile Thr Ile Gly Arg Leu
        450                 455                 460

Val Gln Asn Phe Glu Leu Leu Pro Pro Gly Gln Asp Lys Xaa Asp
465                 470                 475                 480

Thr Thr Glu Lys Gly Gly Gln Phe Ser Leu His Ile Leu Lys His Ser
            485                 490                 495

Thr Ile Val Cys Lys Pro Arg Thr Leu
            500                 505

<210> SEQ ID NO 9
<211> LENGTH: 501
<212> TYPE: PRT
<213> ORGANISM: Zea mays

<400> SEQUENCE: 9

Met Asp Leu Ala Leu Leu Glu Lys Ala Leu Leu Gly Leu Phe Ala Ala
1               5                   10                  15

Ala Val Val Ala Ile Ala Val Ala Lys Leu Thr Gly Lys Arg Tyr Arg
            20                  25                  30

Leu Pro Pro Gly Pro Pro Gly Ala Pro Val Val Gly Asn Trp Leu Gln
        35                  40                  45

Val Gly Asp Asp Leu Asn His Arg Asn Leu Met Ala Met Ala Lys Arg
50                  55                  60

Phe Gly Asp Ile Phe Leu Leu Arg Met Gly Val Arg Asn Leu Val Val
65              70                  75                  80

Val Ser Thr Pro Glu Leu Ala Lys Glu Val Leu His Thr Gln Gly Val
            85                  90                  95

Glu Phe Gly Ser Arg Thr Arg Asn Val Val Phe Asp Ile Phe Thr Gly
        100                 105                 110

Lys Gly Gln Asp Met Val Phe Thr Val Tyr Gly Asp His Trp Arg Lys
    115                 120                 125

Met Arg Arg Ile Met Thr Val Pro Phe Phe Thr Asn Lys Val Val Ala
130                 135                 140

Gln Asn Arg Ala Gly Trp Glu Glu Glu Ala Arg Leu Val Val Glu Asp
145                 150                 155                 160

Val Arg Lys Asp Pro Glu Ala Ala Gly Gly Val Val Leu Arg Arg
            165                 170                 175

Arg Leu Gln Leu Met Met Tyr Asn Asp Met Phe Arg Ile Met Phe Asp
        180                 185                 190

Arg Arg Phe Asp Ser Glu His Asp Pro Leu Phe Asn Lys Leu Lys Ala

```
                195                 200                 205
Leu Asn Ala Glu Arg Ser Arg Leu Ser Gln Ser Phe Glu Tyr Asn Tyr
    210                 215                 220

Gly Asp Phe Ile Pro Val Leu Arg Pro Phe Leu Arg Gly Tyr Leu Asn
225                 230                 235                 240

Arg Cys His Asp Leu Lys Thr Arg Arg Met Lys Val Phe Glu Asp Asn
                245                 250                 255

Phe Val Gln Glu Arg Lys Lys Val Met Ala Gln Thr Gly Glu Ile Arg
            260                 265                 270

Cys Ala Met Asp His Ile Leu Glu Ala Glu Arg Lys Gly Glu Ile Asn
        275                 280                 285

His Asp Asn Val Leu Tyr Ile Val Glu Asn Ile Asn Val Ala Ala Ile
290                 295                 300

Glu Thr Thr Leu Trp Ser Ile Glu Trp Gly Ile Ala Glu Leu Val Asn
305                 310                 315                 320

His Pro Ala Ile Gln His Lys Leu Arg Glu Glu Leu Ala Ser Val Leu
                325                 330                 335

Gly Ala Gly Val Pro Val Thr Glu Pro Asp Leu Glu Arg Leu Pro Tyr
            340                 345                 350

Leu Gln Ala Ile Val Lys Glu Thr Leu Arg Leu Arg Met Ala Ile Pro
        355                 360                 365

Leu Leu Val Pro His Met Asn Leu Asn Asp Gly Lys Leu Ala Gly Phe
    370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Pro Asp Glu Phe Arg Pro Glu Arg
                405                 410                 415

Phe Leu Glu Glu Glu Lys Ser Val Glu Ala His Gly Asn Asp Phe Arg
            420                 425                 430

Phe Val Pro Phe Gly Val Gly Arg Arg Ser Cys Pro Gly Ile Ile Leu
        435                 440                 445

Ala Leu Pro Ile Ile Gly Ile Thr Leu Gly Arg Leu Val Gln Asn Phe
    450                 455                 460

Gln Leu Leu Pro Pro Gly Leu Asp Lys Ile Asp Thr Thr Glu Lys
465                 470                 475                 480

Pro Gly Gln Phe Ser Asn Gln Ile Ala Lys His Ala Thr Ile Val Cys
                485                 490                 495

Lys Pro Leu Glu Ala
            500

<210> SEQ ID NO 10
<211> LENGTH: 370
<212> TYPE: PRT
<213> ORGANISM: Zea mays
<220> FEATURE:
<221> NAME/KEY: VARIANT
<222> LOCATION: (1)...(370)
<223> OTHER INFORMATION: Xaa = Any Amino Acid

<400> SEQUENCE: 10

Met Ala Pro Val Glu Ala Glu Gln His Arg Arg Ala Leu Ala Leu
1               5                   10                  15

Ala Ala His Asp Ala Ser Gly Ala Val Ser Pro Ile Arg Ile Ser Arg
            20                  25                  30

Arg Asp Thr Gly Asp Asp Val Ala Ile Gln Ile Leu Tyr Cys Gly
        35                  40                  45
```

```
Ile Cys His Ser Asp Leu His Thr Ile Lys Asn Glu Trp Lys Asn Ala
         50                  55                  60

Asn Tyr Pro Val Val Pro Gly His Glu Ile Ala Gly Leu Ile Thr Glu
 65                  70                  75                  80

Val Gly Lys Asn Val Lys Arg Phe Asn Val Gly Asp Lys Val Gly Val
                 85                  90                  95

Gly Cys Met Val Asn Thr Cys Gln Ser Cys Glu Ser Cys Glu Gly Gly
             100                 105                 110

His Glu Asn Tyr Cys Ser Lys Ile Ile Phe Thr Tyr Asn Ser His Asp
         115                 120                 125

Arg Asp Gly Thr Val Thr Tyr Gly Gly Tyr Ser Asp Met Val Val Val
     130                 135                 140

Asn Glu Arg Phe Val Ile Arg Phe Pro Asp Gly Met Pro Leu Asp Arg
145                 150                 155                 160

Gly Ala Pro Leu Leu Cys Ala Gly Ile Thr Val Tyr Asn Pro Met Lys
                165                 170                 175

His His Gly Leu Asn Xaa Ala Gly Lys His Ile Xaa Val Xaa Gly Leu
            180                 185                 190

Gly Gly Leu Gly His Val Ala Val Lys Phe Ala Lys Ala Phe Gly Met
        195                 200                 205

Xaa Val Thr Val Ile Ser Thr Ser Pro Gly Xaa Xaa Xaa Glu Ala Met
    210                 215                 220

Glu Thr Leu Gly Ala Asp Ala Phe Val Val Ser Gly Asp Ala Asn Gln
225                 230                 235                 240

Met Lys Ala Ala Lys Gly Thr Met Asp Gly Ile Met Asn Thr Ala Ser
                245                 250                 255

Ala Ser Met Ser Met Tyr Ala Tyr Leu Ala Leu Leu Lys Pro Gln Gly
            260                 265                 270

Lys Met Ile Leu Leu Gly Leu Pro Glu Lys Pro Leu Gln Ile Ser Ala
        275                 280                 285

Phe Ser Leu Val Thr Gly Gly Lys Thr Leu Ala Gly Ser Cys Met Gly
    290                 295                 300

Ser Ile Arg Asp Thr Gln Glu Met Met Asp Phe Ala Ala Lys His Gly
305                 310                 315                 320

Leu Ala Ala Asp Ile Glu Leu Ile Gly Thr Glu Glu Val Asn Glu Ala
                325                 330                 335

Met Glu Arg Leu Ala Lys Gly Glu Val Arg Tyr Arg Phe Val Ile Asp
            340                 345                 350

Ile Gly Asn Thr Leu Asn Ala Ala Ser Leu Gly Ser Ser Pro Val Pro
        355                 360                 365

Ala Leu
    370

<210> SEQ ID NO 11
<211> LENGTH: 359
<212> TYPE: PRT
<213> ORGANISM: Zea mays

<400> SEQUENCE: 11

Met Glu Glu Gln Gly Gly Gln Ala Ala Leu Gly Trp Ala Ala Arg Asp
  1               5                  10                  15

Asp Ser Gly Val Leu Ser Pro Tyr Ser Phe Ser Arg Arg Val Pro Lys
             20                  25                  30

Asp Asp Val Thr Ile Lys Val Leu Tyr Cys Gly Ile Cys His Thr
```

-continued

```
            35                  40                  45
Asp Leu His Val Ile Lys Asn Asp Trp Arg Asn Ala Met Tyr Pro Val
 50                  55                  60
Val Pro Gly His Glu Ile Val Gly Val Thr Gly Val Gly Gly
 65                  70                  75                  80
Val Thr Arg Phe Lys Ala Gly Asp Thr Val Gly Val Gly Tyr Phe Val
                 85                  90                  95
Gly Ser Cys Arg Ser Cys Asp Ser Cys Gly Lys Gly Asp Asp Asn Tyr
                100                 105                 110
Cys Ala Gly Ile Val Leu Thr Ser Asn Gly Val Asp His Ala His Gly
            115                 120                 125
Gly Ala Pro Thr Arg Gly Gly Phe Ser Asp Val Leu Val Ala Ser Glu
130                 135                 140
His Tyr Val Val Arg Val Pro Asp Gly Leu Ala Leu Asp Arg Thr Ala
145                 150                 155                 160
Pro Leu Leu Cys Ala Gly Val Thr Val Tyr Ser Pro Met Met Arg His
                165                 170                 175
Gly Leu Asn Glu Pro Gly Lys His Ser Ala Phe Val Gly Leu Gly Gly
                180                 185                 190
Leu Gly His Val Ala Val Lys Phe Gly Lys Ala Phe Gly Met Lys Val
            195                 200                 205
Thr Val Ile Ser Thr Ser Ala Ser Lys Arg Gln Glu Ala Ile Glu Asn
        210                 215                 220
Leu Gly Ala Asp Glu Phe Leu Ile Ser Arg Asp Glu Asp Gln Met Lys
225                 230                 235                 240
Ala Ala Thr Gly Thr Met Asp Gly Ile Ile Asp Thr Val Ser Ala Trp
                245                 250                 255
His Pro Ile Thr Pro Leu Leu Ala Leu Leu Lys Pro Leu Gly Gln Met
                260                 265                 270
Val Val Val Gly Ala Pro Ser Lys Pro Leu Glu Leu Pro Ala Tyr Ala
            275                 280                 285
Ile Val Pro Gly Lys Gly Val Ala Gly Asn Asn Val Gly Ser Val
        290                 295                 300
Arg Asp Cys Gln Ala Met Leu Glu Phe Ala Gly Lys His Gly Ile Gly
305                 310                 315                 320
Ala Glu Val Glu Val Ile Lys Met Asp Tyr Val Asn Thr Ala Met Glu
                325                 330                 335
Arg Leu Glu Lys Asn Asp Val Arg Tyr Arg Phe Val Ile Asp Val Ala
                340                 345                 350
Gly Ser Leu Gly Ser Ala Ala
            355

<210> SEQ ID NO 12
<211> LENGTH: 358
<212> TYPE: PRT
<213> ORGANISM: Zea mays

<400> SEQUENCE: 12

Met Ala Gly Gly Lys Glu Ala His Gly Trp Ala Ala Arg Asp Val Ser
 1               5                  10                  15
Gly His Leu Ser Pro Tyr His Phe Ser Arg Arg Val Gln Arg Asp Asp
                20                  25                  30
Asp Val Thr Ile Lys Val Leu Phe Cys Gly Leu Cys His Thr Asp Leu
            35                  40                  45
```

```
His Val Ile Lys Asn Glu Phe Gly Asn Ala Lys Tyr Pro Val Pro
 50                  55                  60

Gly His Glu Ile Val Gly Val Thr Asp Val Gly Ser Gly Val Thr
 65                  70                  75                  80

Ser Phe Lys Pro Gly Asp Thr Val Gly Val Tyr Phe Val Asp Ser
                 85                  90                  95

Cys Arg Ser Cys Asp Ser Cys Ser Lys Gly Tyr Glu Ser Tyr Cys Pro
                100                 105                 110

Gln Leu Val Glu Thr Ser Asn Gly Val Ser Leu Asp Asp Asp Gly
                115                 120                 125

Gly Ala Thr Thr Lys Gly Gly Phe Ser Asp Ala Leu Val Val His Gln
130                 135                 140

Arg Tyr Val Val Arg Val Pro Ala Ser Leu Pro Pro Ala Gly Ala Ala
145                 150                 155                 160

Pro Leu Leu Cys Ala Gly Val Thr Val Phe Ser Pro Met Val Gln Tyr
                165                 170                 175

Gly Leu Asn Ala Pro Gly Lys His Leu Gly Val Val Gly Leu Gly Gly
                180                 185                 190

Leu Gly His Leu Ala Val Arg Phe Gly Lys Ala Phe Gly Met Lys Val
    195                 200                 205

Thr Val Ile Ser Thr Ser Leu Gly Lys Arg Asp Glu Ala Leu Gly Arg
    210                 215                 220

Leu Gly Ala Asp Ala Phe Leu Val Ser Arg Asp Pro Glu Gln Met Arg
225                 230                 235                 240

Ala Ala Ala Gly Thr Leu Asp Gly Val Ile Asp Thr Val Ser Ala Asp
                245                 250                 255

His Pro Val Val Pro Leu Leu Asp Leu Leu Lys Pro Met Gly Gln Met
                260                 265                 270

Val Val Val Gly Leu Pro Thr Lys Pro Leu Gln Val Pro Ala Phe Ser
                275                 280                 285

Leu Val Ala Gly Gly Lys Arg Val Ala Gly Ser Ala Gly Gly Gly Val
                290                 295                 300

Gly Glu Cys Gln Ala Met Leu Asp Phe Ala Gly Glu His Gly Ile Thr
305                 310                 315                 320

Ala Asp Val Glu Val Gly Met Asp Tyr Val Asn Thr Ala Ile Gln
                325                 330                 335

Arg Leu Glu Arg Asn Asp Val Arg Tyr Arg Phe Val Val Asp Val Ala
                340                 345                 350

Gly Ser Lys Ile Gly Gly
                355

<210> SEQ ID NO 13
<211> LENGTH: 258
<212> TYPE: PRT
<213> ORGANISM: Zea mays

<400> SEQUENCE: 13

Met Ala Thr Thr Ala Thr Glu Ala Ala Pro Ala Gln Glu Gln Gln Ala
  1               5                  10                  15

Asn Gly Asn Gly Glu Gln Lys Thr Arg His Ser Glu Val Gly His Lys
                 20                  25                  30

Ser Leu Leu Lys Ser Asp Asp Leu Tyr Gln Tyr Ile Leu Asp Thr Ser
                 35                  40                  45

Val Tyr Pro Arg Glu Pro Glu Ser Met Lys Glu Leu Arg Glu Ile Thr
 50                  55                  60
```

```
Ala Lys His Pro Trp Asn Leu Met Thr Thr Ser Ala Asp Glu Gly Gln
 65                  70                  75                  80

Phe Leu Asn Met Leu Ile Lys Leu Ile Gly Ala Lys Lys Thr Met Glu
                 85                  90                  95

Ile Gly Val Tyr Thr Gly Tyr Ser Leu Leu Ala Thr Ala Leu Ala Leu
            100                 105                 110

Pro Glu Asp Gly Thr Ile Leu Ala Met Asp Ile Asn Arg Glu Asn Tyr
        115                 120                 125

Glu Leu Gly Leu Pro Cys Ile Glu Lys Ala Gly Val Ala His Lys Ile
130                 135                 140

Asp Phe Arg Glu Gly Pro Ala Leu Pro Val Leu Asp Asp Leu Ile Ala
145                 150                 155                 160

Glu Glu Lys Asn His Gly Ser Phe Asp Phe Val Phe Val Asp Ala Asp
                165                 170                 175

Lys Asp Asn Tyr Leu Asn Tyr His Glu Arg Leu Leu Lys Leu Val Lys
            180                 185                 190

Leu Gly Gly Leu Ile Gly Tyr Asp Asn Thr Leu Trp Asn Gly Ser Val
        195                 200                 205

Val Leu Pro Asp Asp Ala Pro Met Arg Lys Tyr Ile Arg Phe Tyr Arg
210                 215                 220

Asp Phe Val Leu Val Leu Asn Lys Ala Leu Ala Ala Asp Asp Arg Val
225                 230                 235                 240

Glu Ile Cys Gln Leu Pro Val Gly Asp Gly Val Thr Leu Cys Arg Arg
                245                 250                 255

Val Lys

<210> SEQ ID NO 14
<211> LENGTH: 248
<212> TYPE: PRT
<213> ORGANISM: Zea mays

<400> SEQUENCE: 14

Met Ala Ser Ala Gly Ala Gly Glu Gly Lys Glu Thr Ala Ala Gly Ser
 1               5                  10                  15

Ser Leu His Ser Lys Thr Leu Leu Lys Ser Gln Pro Leu Tyr Gln Tyr
             20                  25                  30

Ile Leu Glu Ser Thr Val Phe Pro Arg Glu Pro Asp Cys Leu Arg Glu
         35                  40                  45

Leu Arg Val Ala Thr Ala Thr His Pro Met Ala Gly Met Ala Ala Ser
     50                  55                  60

Pro Asp Glu Val Gln Leu Leu Gln Leu Leu Ile Glu Ile Leu Gly Ala
 65                  70                  75                  80

Lys Asn Ala Ile Glu Val Gly Val Phe Thr Gly Tyr Ser Leu Leu Ala
                 85                  90                  95

Thr Ala Leu Ala Leu Pro Asp Asp Gly Lys Ile Val Ala Ile Asp Val
            100                 105                 110

Thr Arg Glu Ser Tyr Asp Gln Ile Gly Ser Pro Val Ile Glu Lys Ala
        115                 120                 125

Gly Val Ala His Lys Ile Asp Phe Arg Val Gly Leu Ala Leu Pro Val
130                 135                 140

Leu Asp Gln Met Val Ala Glu Glu Gly Asn Lys Gly Lys Phe Asp Phe
145                 150                 155                 160

Ala Phe Val Asp Ala Asp Lys Val Asn Phe Leu Asn Tyr His Glu Arg
                165                 170                 175
```

-continued

Leu Leu Gln Leu Leu Arg Val Gly Gly Leu Ile Ala Tyr Asp Asn Thr
            180                 185                 190

Leu Trp Gly Gly Ser Val Ala Ala Ser Pro Asp Glu Pro Leu Ser Glu
        195                 200                 205

Arg Asp Arg Ala Leu Ala Ala Ala Thr Arg Glu Phe Asn Ala Ala Val
    210                 215                 220

Ala Ala Asp Pro Arg Val His Val Cys Gln Val Ala Ile Ala Asp Gly
225                 230                 235                 240

Leu Thr Leu Cys Arg Arg Val Ala
                245

<210> SEQ ID NO 15
<211> LENGTH: 248
<212> TYPE: PRT
<213> ORGANISM: Zea mays

<400> SEQUENCE: 15

Met Ala Ala Gly Gly Asp Asp Thr Thr Ile Ala Gln Val His Ser Gly
1               5                   10                  15

Ile Asp Ser Ser Asn Lys Thr Leu Leu Lys Ser Glu Ala Leu Tyr Lys
            20                  25                  30

Tyr Val Leu Asp Thr Ser Val Leu Pro His Glu Pro Glu Ser Met Arg
        35                  40                  45

Glu Leu Arg Leu Val Thr Asp Lys His Glu Trp Gly Phe Met Gln Ser
    50                  55                  60

Ser Pro Asp Glu Ala Ser Leu Leu Arg Met Leu Ile Lys Leu Ser Gly
65                  70                  75                  80

Ala Arg Arg Thr Leu Glu Val Gly Val Phe Thr Gly Tyr Ser Leu Leu
                85                  90                  95

Ala Thr Ala Leu Ala Leu Pro Ala Asp Gly Lys Val Ile Ala Phe Asp
            100                 105                 110

Val Ser Arg Glu Tyr Tyr Asp Ile Gly Arg Pro Phe Ile Glu Arg Ala
        115                 120                 125

Gly Val Ala Gly Lys Val Asp Phe Arg Glu Gly Pro Ala Leu Glu Gln
    130                 135                 140

Leu Asp Glu Leu Leu Ala Asp Pro Ala Asn His Gly Ala Phe Asp Phe
145                 150                 155                 160

Ala Phe Val Asp Ala Asp Lys Pro Asn Tyr Val Arg Tyr His Glu Gln
                165                 170                 175

Leu Leu Arg Leu Val Arg Val Gly Gly Thr Val Val Tyr Asp Asn Thr
            180                 185                 190

Leu Trp Ala Gly Thr Val Ala Leu Pro Pro Asp Ala Pro Leu Ser Asp
        195                 200                 205

Leu Asp Arg Arg Phe Ser Ala Ala Ile Arg Glu Leu Asn Val Arg Leu
    210                 215                 220

Ser Gln Asp Pro Arg Val Glu Val Cys Gln Leu Ala Ile Ala Asp Gly
225                 230                 235                 240

Val Thr Ile Cys Arg Arg Val Val
                245

<210> SEQ ID NO 16
<211> LENGTH: 371
<212> TYPE: PRT
<213> ORGANISM: Zea mays
<220> FEATURE:
<221> NAME/KEY: VARIANT
<222> LOCATION: (1)...(371)
<223> OTHER INFORMATION: Xaa = Any Amino Acid

<400> SEQUENCE: 16

```
Met Thr Val Val Asp Ala Val Ser Ser Thr Asp Ala Gly Ala Pro
 1               5                  10                  15

Ala Ala Ala Ala Thr Ala Val Pro Ala Gly Asn Gly Gln Thr Val Cys
             20                  25                  30

Val Thr Gly Ala Ala Gly Tyr Ile Ala Ser Trp Leu Val Lys Leu Leu
             35                  40                  45

Leu Glu Lys Gly Tyr Thr Val Lys Gly Thr Val Arg Asn Pro Asp Asp
 50                  55                  60

Pro Lys Asn Ala His Leu Lys Ala Leu Asp Gly Ala Ala Glu Arg Leu
 65                  70                  75                  80

Ile Leu Cys Lys Ala Asp Leu Leu Asp Tyr Asp Ala Ile Cys Arg Ala
                 85                  90                  95

Val Gln Gly Cys Gln Gly Val Phe His Thr Ala Ser Pro Val Thr Asp
            100                 105                 110

Asp Pro Glu Gln Met Val Glu Pro Ala Val Arg Gly Thr Glu Tyr Val
            115                 120                 125

Ile Asn Ala Ala Ala Asp Ala Gly Thr Val Arg Arg Val Val Phe Thr
            130                 135                 140

Ser Ser Ile Gly Ala Val Thr Met Asp Pro Lys Arg Gly Pro Asp Val
145                 150                 155                 160

Val Val Asp Glu Ser Cys Trp Ser Asp Leu Glu Phe Cys Glu Lys Thr
                165                 170                 175

Arg Asn Trp Tyr Cys Tyr Gly Lys Ala Val Ala Glu Gln Ala Ala Trp
                180                 185                 190

Glu Thr Ala Arg Arg Gly Val Asp Leu Val Val Asn Pro Val
                195                 200                 205

Leu Val Val Gly Pro Leu Leu Gln Ala Thr Val Asn Ala Ser Ile Ala
            210                 215                 220

His Ile Leu Lys Tyr Leu Asp Gly Ser Ala Arg Thr Phe Ala Asn Ala
225                 230                 235                 240

Val Gln Ala Tyr Val Asp Val Arg Asp Val Ala Asp Ala His Leu Arg
                245                 250                 255

Val Phe Glu Ser Pro Arg Ala Ser Gly Arg Xaa Leu Cys Ala Glu Arg
                260                 265                 270

Val Leu His Arg Glu Asp Val Val Arg Ile Leu Ala Lys Leu Phe Pro
            275                 280                 285

Glu Tyr Pro Val Pro Ala Arg Cys Ser Asp Glu Val Asn Pro Arg Lys
290                 295                 300

Gln Pro Tyr Lys Phe Ser Asn Gln Lys Leu Arg Asp Leu Gly Leu Gln
305                 310                 315                 320

Phe Arg Pro Val Ser Gln Ser Leu Tyr Asp Thr Val Lys Asn Leu Gln
                325                 330                 335

Glu Lys Gly His Leu Pro Val Leu Gly Glu Arg Thr Thr Glu Ala
            340                 345                 350

Ala Asp Lys Asp Ala Pro Thr Ala Glu Met Gln Gln Gly Gly Ile Ala
            355                 360                 365

Ile Arg Ala
    370
```

<210> SEQ ID NO 17

```
<211> LENGTH: 177
<212> TYPE: PRT
<213> ORGANISM: Zea mays

<400> SEQUENCE: 17

Thr Arg Pro Val Val Gly Leu Asp Arg Asn Val Ser Glu Ser Asp Leu
1               5                   10                  15

Asp Arg Leu Pro Phe Leu Arg Cys Val Ile Lys Glu Thr Leu Arg Leu
            20                  25                  30

His Pro Pro Ile Pro Leu Leu Leu His Glu Thr Ala Asp Asp Cys Val
        35                  40                  45

Val Ala Gly Tyr Ser Val Pro Arg Gly Ser Arg Val Met Val Asn Val
    50                  55                  60

Trp Ala Ile Gly Arg His Arg Ala Ser Trp Lys Asp Ala Asp Ala Phe
65                  70                  75                  80

Arg Pro Ser Arg Phe Ala Ala Pro Glu Gly Glu Ala Ala Gly Leu Asp
                85                  90                  95

Phe Lys Gly Gly Cys Phe Glu Phe Leu Pro Phe Gly Ser Gly Arg Arg
            100                 105                 110

Ser Cys Pro Gly Met Ala Leu Gly Leu Tyr Ala Leu Glu Leu Ala Val
        115                 120                 125

Ala Gln Leu Ala His Ala Phe Asn Trp Ser Leu Pro Asp Gly Met Lys
    130                 135                 140

Pro Ser Glu Met Asp Met Gly Asp Ile Phe Gly Leu Thr Ala Pro Arg
145                 150                 155                 160

Ala Thr Arg Leu Tyr Ala Val Pro Thr Pro Arg Leu Asn Cys Pro Leu
                165                 170                 175

Tyr

<210> SEQ ID NO 18
<211> LENGTH: 235
<212> TYPE: PRT
<213> ORGANISM: Zea mays

<400> SEQUENCE: 18

Ala Arg Asp Phe Pro Asp Gly Pro Pro Ser Gly Thr Ala Met Ser
1               5                   10                  15

Val Gly Thr Lys Leu Asn Lys Leu Ser Tyr Asn Ser Val Val Glu Ile
            20                  25                  30

Val Leu Gln Asn Pro Ala Ala Val Pro Thr Glu Asn His Pro Ile His
        35                  40                  45

Leu His Gly Phe Asn Phe Phe Val Leu Ala Gln Gly Met Gly Thr Phe
    50                  55                  60

Ala Pro Gly Ser Val Ala Tyr Asn Leu Val Asp Pro Val Ala Arg Asn
65                  70                  75                  80

Thr Ile Ala Val Pro Gly Gly Trp Ala Val Ile Arg Phe Val Ala
                85                  90                  95

Asn Asn Pro Gly Met Trp Phe Phe His Cys His Leu Asp Pro His Val
            100                 105                 110

Pro Met Gly Leu Gly Met Val Phe Gln Val Asp Ser Gly Thr Thr Pro
        115                 120                 125

Gly Ser Thr Leu Pro Thr Pro Pro Gly Asp Trp Val Gly Val Cys Asp
    130                 135                 140

Ala Gln His Tyr Ala Ala Ala Ala Val Ala Ala Ala Pro Val Pro
145                 150                 155                 160
```

```
Val Pro Ala Pro Ala Pro Val Pro Ala Pro Ile Leu Ala Pro Ala Pro
                165                 170                 175

Ala Glu Ser Pro Leu Pro Pro Arg Ala Val Asp His Lys Pro Ser
            180                 185                 190

Pro Asn Leu Pro Gln Arg Arg Glu His Thr Gly Thr Ser Asn Ser Ala
            195                 200                 205

Ala Gly Arg Arg Ala Lys Gly His Leu Ala Cys Phe Leu Cys Ser Val
210                 215                 220

Leu Leu Phe Phe Leu Leu Arg Gln His Lys Ala
225                 230                 235

<210> SEQ ID NO 19
<211> LENGTH: 1924
<212> TYPE: DNA
<213> ORGANISM: Zea mays
<220> FEATURE:
<221> NAME/KEY: CDS
<222> LOCATION: (16)...(1692)

<400> SEQUENCE: 19
cagcagcagc tgagg atg ggc gac gcg gcc atc gcc gcc gtg cat ttg cat      51
                 Met Gly Asp Ala Ala Ile Ala Ala Val His Leu His
                  1               5                  10 gag tct gag gag gag cac atc ttc cgg agc cgg ttc ccg ccc gtg gcc      99
Glu Ser Glu Glu Glu His Ile Phe Arg Ser Arg Phe Pro Pro Val Ala
         15                  20                  25 gta cca gac gac gtc acc gtg ccg gag ttc gtg ctg gcg gac gcc gag     147
Val Pro Asp Asp Val Thr Val Pro Glu Phe Val Leu Ala Asp Ala Glu
 30                  35                  40 gcc tac gcg gac aag acg gcg ctc gtg gag gcc gcg ccg ggt ggc cgg     195
Ala Tyr Ala Asp Lys Thr Ala Leu Val Glu Ala Ala Pro Gly Gly Arg
 45                  50                  55                  60 tcc tac acc tac ggc gag ctg gtc cgg gac gtg gcg cgg ttc gcc agg     243
Ser Tyr Thr Tyr Gly Glu Leu Val Arg Asp Val Ala Arg Phe Ala Arg
                 65                  70                  75 gcg ctg cgg tcc atc ggc gtc cgc agg ggc cac gtc gtg gtg gtc gcg     291
Ala Leu Arg Ser Ile Gly Val Arg Arg Gly His Val Val Val Val Ala
             80                  85                  90 ctc ccg aac ctg gcg gtg tac ccc gtg gtg agc ctc ggg atc atg tcc     339
Leu Pro Asn Leu Ala Val Tyr Pro Val Val Ser Leu Gly Ile Met Ser
         95                 100                 105 gcc gga gcg gtc ttc tcc ggc gtg aac ccg cgc gcc gtc gcc gcc gag     387
Ala Gly Ala Val Phe Ser Gly Val Asn Pro Arg Ala Val Ala Ala Glu
110                 115                 120 atc aag aag cag gtg gag gac tcc gag gcc agg ctc gtg gtc gcc gac     435
Ile Lys Lys Gln Val Glu Asp Ser Glu Ala Arg Leu Val Val Ala Asp
125                 130                 135                 140 gcg gtg gcc tac gac aag gtg aag gac gct ggc gtg ccg gtg atc ggc     483
Ala Val Ala Tyr Asp Lys Val Lys Asp Ala Gly Val Pro Val Ile Gly
                145                 150                 155 atc ggg gac gtg gcg cgg ctt ccc ggc gcc ata ggc tgg gac gag ctc     531
Ile Gly Asp Val Ala Arg Leu Pro Gly Ala Ile Gly Trp Asp Glu Leu
                160                 165                 170 ctc gcc atg gcg gac cgc gcg ggc gcg ccg gtg gtg gcg ctt gag ccg     579
Leu Ala Met Ala Asp Arg Ala Gly Ala Pro Val Val Ala Leu Glu Pro
            175                 180                 185 gcg cag cag tcc gac ctg tgc gcg ctc ccc tac tcg tct ggt acg acg     627
Ala Gln Gln Ser Asp Leu Cys Ala Leu Pro Tyr Ser Ser Gly Thr Thr
        190                 195                 200 ggg gtg tcc aag ggc gtg atg ctg agc cac cgg aac ctg gtg tcc agc     675
Gly Val Ser Lys Gly Val Met Leu Ser His Arg Asn Leu Val Ser Ser
```

-continued

| | | |
|---|---|---|
| Gly Val Ser Lys Gly Val Met Leu Ser His Arg Asn Leu Val Ser Ser<br>205                         210                         215                        220 | | |
| ctc tgc tcc tcc atg ttc gcc gtc ggg cag gag ctg gtc ggg cag gtg<br>Leu Cys Ser Ser Met Phe Ala Val Gly Gln Glu Leu Val Gly Gln Val<br>                      225                         230                        235 | 723 | |
| gtc acc ctg ggc ctg atg ccc ttc ttc cac atc tac ggc atc acc ggc<br>Val Thr Leu Gly Leu Met Pro Phe Phe His Ile Tyr Gly Ile Thr Gly<br>              240                        245                        250 | 771 | |
| atc tgc tgc gcc acg ctg cgg cac aag ggc acg gtg gtg gtg atg gac<br>Ile Cys Cys Ala Thr Leu Arg His Lys Gly Thr Val Val Val Met Asp<br>        255                        260                        265 | 819 | |
| cgc ttc gac ctg cgc gcg ttc ctg ggc gcg ctg ctg acg cac cgc gtc<br>Arg Phe Asp Leu Arg Ala Phe Leu Gly Ala Leu Leu Thr His Arg Val<br>270                         275                         280 | 867 | |
| atg ttc gcg ccc gtc gtg ccg ccg gtc atg ctg gcc atg gtg aag agc<br>Met Phe Ala Pro Val Val Pro Pro Val Met Leu Ala Met Val Lys Ser<br>285                         290                        295                        300 | 915 | |
| ccc gtg gcc gac gag ttc gac ctg tcc ggc ctg gcc ctc agg tcc gtc<br>Pro Val Ala Asp Glu Phe Asp Leu Ser Gly Leu Ala Leu Arg Ser Val<br>                               305                        310                        315 | 963 | |
| atg acg gcc gcc gcg ccg ctc gcg ccg gac ctc ctg gcg gcg ttc gag<br>Met Thr Ala Ala Ala Pro Leu Ala Pro Asp Leu Leu Ala Ala Phe Glu<br>        320                        325                        330 | 1011 | |
| cgc aag ttc ccg ggc gtg cag gtg gag gag gcg tac ggg ctc acg gag<br>Arg Lys Phe Pro Gly Val Gln Val Glu Glu Ala Tyr Gly Leu Thr Glu<br>              335                        340                        345 | 1059 | |
| cac agc tgc atc acg ctg acg cac gcc agc ggc ggc ggc gag gac gtg<br>His Ser Cys Ile Thr Leu Thr His Ala Ser Gly Gly Gly Glu Asp Val<br>350                         355                         360 | 1107 | |
| ggg tcg gcg gtg cag gtc gcc aag aag aag tcg gtc ggc ttc atc ctg<br>Gly Ser Ala Val Gln Val Ala Lys Lys Lys Ser Val Gly Phe Ile Leu<br>365                         370                        375                        380 | 1155 | |
| ccc aac ctg gag gtg aag ttc gtg gac ccc gac acg ggg cgg tcg ctg<br>Pro Asn Leu Glu Val Lys Phe Val Asp Pro Asp Thr Gly Arg Ser Leu<br>                      385                        390                        395 | 1203 | |
| ccc aag aac acg ccg ggg gag atc tgc gtg cgg agc cag gcc gtg atg<br>Pro Lys Asn Thr Pro Gly Glu Ile Cys Val Arg Ser Gln Ala Val Met<br>              400                        405                        410 | 1251 | |
| cag ggc tac tac agg aag aag gag gag acg gag cgc acc atc gac gcc<br>Gln Gly Tyr Tyr Arg Lys Lys Glu Glu Thr Glu Arg Thr Ile Asp Ala<br>                      415                        420                        425 | 1299 | |
| gcg ggg tgg ctc cac acg ggc gac gtc ggg tac atc gac gac gac ggc<br>Ala Gly Trp Leu His Thr Gly Asp Val Gly Tyr Ile Asp Asp Asp Gly<br>430                         435                        440 | 1347 | |
| gac gtg ttc atc gtg gac cgc atc aag gag ctc atc aag tac aag ggc<br>Asp Val Phe Ile Val Asp Arg Ile Lys Glu Leu Ile Lys Tyr Lys Gly<br>445                         450                        455                        460 | 1395 | |
| ttc caa gtc gcc cct gcc gag ctg gag gcc atc ctg ctg tct cac ccg<br>Phe Gln Val Ala Pro Ala Glu Leu Glu Ala Ile Leu Leu Ser His Pro<br>                      465                        470                        475 | 1443 | |
| tcc gtc gag gac gcc gcc gtc ttc ggg ctg ccg gac gag gag gcc ggc<br>Ser Val Glu Asp Ala Ala Val Phe Gly Leu Pro Asp Glu Glu Ala Gly<br>                               480                        485                        490 | 1491 | |
| gag gtc ccg gcg tcg tgc gtg gtg cgg cga cgt ggc gcg ccg gag agc<br>Glu Val Pro Ala Ser Cys Val Val Arg Arg Arg Gly Ala Pro Glu Ser<br>        495                        500                        505 | 1539 | |
| gag gcg gac atg atg gcg tac gtg gcg ggg cgc gtt gcg tcg tac aag<br>Glu Ala Asp Met Met Ala Tyr Val Ala Gly Arg Val Ala Ser Tyr Lys<br>510                         515                        520 | 1587 | |

-continued

| | |
|---|---|
| aag ctc cgg ctg ctg cgc ttc gtg gac gcc atc ccc aag tcg gtg tcc<br>Lys Leu Arg Leu Leu Arg Phe Val Asp Ala Ile Pro Lys Ser Val Ser<br>525                    530                    535                  540 | 1635 |
| ggc aag atc ctg cgg agg cag ctc agg gac gag ttc gtc aag aag acg<br>Gly Lys Ile Leu Arg Arg Gln Leu Arg Asp Glu Phe Val Lys Lys Thr<br>                  545                    550                    555 | 1683 |
| gca gca gcg taataatgca catcatcctg tgggtgggtg cttgcttata<br>Ala Ala Ala | 1732 |
| ccagtgcaag atcctgcatt cgccacttga tgaagacaat aatacaatta gggtacagtc | 1792 |
| agatgttcca agctactgat acaattgttg tttctgcaaa cagtactcca aactagtgca | 1852 |
| tatacattgg cgttgtggac ccaaaaaaaa ctgctgttcc tgaataactt gagcttcccc | 1912 |
| cagttccctc cc | 1924 |

<210> SEQ ID NO 20
<211> LENGTH: 2122
<212> TYPE: DNA
<213> ORGANISM: Zea mays
<220> FEATURE:
<221> NAME/KEY: CDS
<222> LOCATION: (156)...(1820)

<400> SEQUENCE: 20

| | |
|---|---|
| gtcgacccac gcgtccggcc ccggcgaggt cgcaccgcac cagccatcgt ctccttcctt | 60 |
| ccttcctata ctaccatcca accagctgcc cagcgcaacg ttacctgccc gacatccgac | 120 |
| aagccagtcc atccggcagc gagcaaaggt ctgag atg ggt tcc gta gac gcg<br>                                                          Met Gly Ser Val Asp Ala<br>                                                          1                  5 | 173 |
| gcg atc gcg gtg ccg gtg ccg gcg gcg gag gag aag gcg gtg gag gag<br>Ala Ile Ala Val Pro Val Pro Ala Ala Glu Glu Lys Ala Val Glu Glu<br>          10                    15                    20 | 221 |
| aag gcg atg gtg ttc cgg tcc aag ctt ccc gac atc gag atc gac agc<br>Lys Ala Met Val Phe Arg Ser Lys Leu Pro Asp Ile Glu Ile Asp Ser<br> 25                    30                    35 | 269 |
| agc atg gcg ctg cac acc tac tgc ttc ggg aag atg ggc gag gtg gcg<br>Ser Met Ala Leu His Thr Tyr Cys Phe Gly Lys Met Gly Glu Val Ala<br>    40                    45                    50 | 317 |
| gag cgg gcg tgc ctg atc gac ggg ctg acg ggc gcg tcg tac acg tac<br>Glu Arg Ala Cys Leu Ile Asp Gly Leu Thr Gly Ala Ser Tyr Thr Tyr<br>55                    60                    65                    70 | 365 |
| gcg gag gtg gag tcc ctg tcc cgg cgc gcc gcg tcg ggg ctg cgc gcc<br>Ala Glu Val Glu Ser Leu Ser Arg Arg Ala Ala Ser Gly Leu Arg Ala<br>                  75                    80                    85 | 413 |
| atg ggg gtg ggc aag ggc gac gtg gtg atg agc ctg ctc cgc aac tgc<br>Met Gly Val Gly Lys Gly Asp Val Val Met Ser Leu Leu Arg Asn Cys<br>          90                    95                    100 | 461 |
| ccc gag ttc gcc ttc acc ttc ctg ggc gcc gcc cgc ctg ggc gcc gcc<br>Pro Glu Phe Ala Phe Thr Phe Leu Gly Ala Ala Arg Leu Gly Ala Ala<br> 105                    110                    115 | 509 |
| acc acc acg gcc aac ccg ttc tac acc ccg cac gag gtg cac cgc cag<br>Thr Thr Thr Ala Asn Pro Phe Tyr Thr Pro His Glu Val His Arg Gln<br>    120                    125                    130 | 557 |
| gcg gag gcg gcc ggc gcc agg ctc atc gtg acc gag gcc tgc gcc gtg<br>Ala Glu Ala Ala Gly Ala Arg Leu Ile Val Thr Glu Ala Cys Ala Val<br>135                    140                    145                    150 | 605 |
| gag aag gtg cgg gag ttc gcg gcg gag cgg ggc atc ccc gtg gtc acc<br>Glu Lys Val Arg Glu Phe Ala Ala Glu Arg Gly Ile Pro Val Val Thr<br>                  155                    160                    165 | 653 |
| gtc gac ggg cgc ttc gac ggc tgc gtg gag ttc gcc gag ctg atc gcg | 701 |

```
                                                                -continued

Val Asp Gly Arg Phe Asp Gly Cys Val Glu Phe Ala Glu Leu Ile Ala
        170                 175                 180 gcc gag gag ctg gag gcc gac gcc gac atc cac ccc gac gac gtc gtc       749
Ala Glu Glu Leu Glu Ala Asp Ala Asp Ile His Pro Asp Asp Val Val
            185                 190                 195 gcg ctg ccc tac tcc tcc ggc acc acc ggg ctg ccc aag ggc gtc atg       797
Ala Leu Pro Tyr Ser Ser Gly Thr Thr Gly Leu Pro Lys Gly Val Met
200                 205                 210 ctc acc cac cgc agc ctc atc acc agc gtc gcg cag cag gtt gat ggc       845
Leu Thr His Arg Ser Leu Ile Thr Ser Val Ala Gln Gln Val Asp Gly
215                 220                 225                 230 gag aac ccg aac ctg tac ttc cgc aag gac gac gtg gtg ctg tgc ctg       893
Glu Asn Pro Asn Leu Tyr Phe Arg Lys Asp Asp Val Val Leu Cys Leu
                235                 240                 245 ctg ccg ctg ttc cac atc tac tcg ctg aac tcg gtg ctg ctg gcc ggc       941
Leu Pro Leu Phe His Ile Tyr Ser Leu Asn Ser Val Leu Leu Ala Gly
            250                 255                 260 ctg cgc gcg ggc tcc acc atc gtg atc atg cgc aag ttc gac ctg ggc       989
Leu Arg Ala Gly Ser Thr Ile Val Ile Met Arg Lys Phe Asp Leu Gly
        265                 270                 275 gcg ctg gtg gac ctg gtg cgc agg tac gtg atc acc atc gcg ccc ttc      1037
Ala Leu Val Asp Leu Val Arg Arg Tyr Val Ile Thr Ile Ala Pro Phe
    280                 285                 290 gtg ccg ccc atc gtg gtg gag atc gcc aag agc ccc cgc gtg acc gcc      1085
Val Pro Pro Ile Val Val Glu Ile Ala Lys Ser Pro Arg Val Thr Ala
295                 300                 305                 310 ggc gac ctc gcg tcc atc cgc atg gtc atg tcc ggc gcc gcg ccc atg      1133
Gly Asp Leu Ala Ser Ile Arg Met Val Met Ser Gly Ala Ala Pro Met
                315                 320                 325 ggc aag gag ctc cag gac gcc ttc atg gcc aag att ccc aat gcc gtg      1181
Gly Lys Glu Leu Gln Asp Ala Phe Met Ala Lys Ile Pro Asn Ala Val
            330                 335                 340 ctc ggg cag ggg tac ggg atg acg gag gca ggc ccc gtg ctg gcg atg      1229
Leu Gly Gln Gly Tyr Gly Met Thr Glu Ala Gly Pro Val Leu Ala Met
        345                 350                 355 tgc ctg gcc ttc gcc aag gag ccg tac ccg gtc aag tcc ggg tcg tgc      1277
Cys Leu Ala Phe Ala Lys Glu Pro Tyr Pro Val Lys Ser Gly Ser Cys
    360                 365                 370 ggc acc gtg gtg cgg aac gcg gag ctg aag atc gtc gac ccc gac acc      1325
Gly Thr Val Val Arg Asn Ala Glu Leu Lys Ile Val Asp Pro Asp Thr
375                 380                 385                 390 ggc gcc gcc ctc ggc cgg aac cag ccc ggc gag atc tgc atc cgc ggg      1373
Gly Ala Ala Leu Gly Arg Asn Gln Pro Gly Glu Ile Cys Ile Arg Gly
                395                 400                 405 gag cag atc atg aaa ggt tac ctg aac gac ccc gag tcg acg aag aac      1421
Glu Gln Ile Met Lys Gly Tyr Leu Asn Asp Pro Glu Ser Thr Lys Asn
            410                 415                 420 acc atc gac aag gac ggc tgg ctg cac acc gga gac atc ggc tac gtg      1469
Thr Ile Asp Lys Asp Gly Trp Leu His Thr Gly Asp Ile Gly Tyr Val
        425                 430                 435 gac gac gac gac gag atc ttc atc gtc gac agg ctc aag gag atc atc      1517
Asp Asp Asp Asp Glu Ile Phe Ile Val Asp Arg Leu Lys Glu Ile Ile
    440                 445                 450 aag tac aag ggc ttc cag gtg ccg ccg gcg gag ctg gag gcg ctc ctc      1565
Lys Tyr Lys Gly Phe Gln Val Pro Pro Ala Glu Leu Glu Ala Leu Leu
455                 460                 465                 470 atc acg cac ccg gag atc aag gac gcc gcc gtc gtc tca atg aac gat      1613
Ile Thr His Pro Glu Ile Lys Asp Ala Ala Val Val Ser Met Asn Asp
                475                 480                 485
```

```
gac ctt gct ggt gaa atc ccg gtc gcc ttc atc gtg cgg acc gaa ggt        1661
Asp Leu Ala Gly Glu Ile Pro Val Ala Phe Ile Val Arg Thr Glu Gly
            490                 495                 500 tct caa gtc acc gag gat gag atc aag caa ttc gtc gcc aag gag gtg        1709
Ser Gln Val Thr Glu Asp Glu Ile Lys Gln Phe Val Ala Lys Glu Val
        505                 510                 515 gtt ttc tac aag aag atc cac aag gtc ttc ttc acc gaa tcc atc ccc        1757
Val Phe Tyr Lys Lys Ile His Lys Val Phe Phe Thr Glu Ser Ile Pro
    520                 525                 530 aag aac ccg tcg ggc aag atc ctg agg aag gac ttg aga gcc agg ctc        1805
Lys Asn Pro Ser Gly Lys Ile Leu Arg Lys Asp Leu Arg Ala Arg Leu
535                 540                 545                 550 gcc gcc ggt gtt cag tgaggcccgt atgcagcttc ttctcagacg cccaccacac        1860
Ala Ala Gly Val Gln
                555 tgctgcgaaa aaaaaggcg atgtaatggc ggtaacacta ctattcatga acaggcaaca       1920 gaagggacac gtattcctgt ggaacacatg ttgccagaaa gaggttttag tttgtctgtt       1980 tgttggccct gtgtgtaatg ttcataaacg atatagacgt ctctctatgt tgtttttgac       2040 ccaaagaaca agcctgatta cggcaataca gctatggagt accgtgtttc ataaaaaaaa       2100 aaaaaaaaaa aagggcggcc gc                                                2122

<210> SEQ ID NO 21
<211> LENGTH: 1970
<212> TYPE: DNA
<213> ORGANISM: Zea mays
<220> FEATURE:
<221> NAME/KEY: CDS
<222> LOCATION: (43)...(1767)

<400> SEQUENCE: 21
ccacgcgtcc gcactggtcc ggattcgcag agcaaaacgg aa atg atc acg gtg          54
                                               Met Ile Thr Val
                                                 1 gca gca ccg gag gcg cag ccg cag gtg gcg gcg gcg gcg gcg gtt gcg        102
Ala Ala Pro Glu Ala Gln Pro Gln Val Ala Ala Ala Ala Ala Val Ala
  5                  10                  15                  20 gcg ccg gag gag acc gtg ttc cgg tcg aag ctg ccg gac atc gac atc        150
Ala Pro Glu Glu Thr Val Phe Arg Ser Lys Leu Pro Asp Ile Asp Ile
                 25                  30                  35 ccc acc cac ctg ccg ctc cac gac tac tgc ttc tcg agg gcg gcg gag        198
Pro Thr His Leu Pro Leu His Asp Tyr Cys Phe Ser Arg Ala Ala Glu
         40                  45                  50 gcg gcg ggc gcg ccg tgc ctc atc gcg gcg gcc acg ggg agg acc tac        246
Ala Ala Gly Ala Pro Cys Leu Ile Ala Ala Ala Thr Gly Arg Thr Tyr
     55                  60                  65 acg tac gcc gag acg cgc ctc ctg tgc cgc aag gcc gcg gcg tgc ctc        294
Thr Tyr Ala Glu Thr Arg Leu Leu Cys Arg Lys Ala Ala Ala Cys Leu
 70                  75                  80 cac ggg ctc ggc gtc gcc cag ggc gac cgc gtc atg ctc ctg ctc cag        342
His Gly Leu Gly Val Ala Gln Gly Asp Arg Val Met Leu Leu Leu Gln
 85                  90                  95                 100 aac tcc gtc gag ttc gtg ctc gcc ttc ttc ggc gcg tcc ttc ctc ggc        390
Asn Ser Val Glu Phe Val Leu Ala Phe Phe Gly Ala Ser Phe Leu Gly
                105                 110                 115 gcc gtc acc acg gcc gcc aac cca ttc tgc acg ccg cag gag atc cac        438
Ala Val Thr Thr Ala Ala Asn Pro Phe Cys Thr Pro Gln Glu Ile His
        120                 125                 130 aag cag ttc agc gcc tcc ggc gcg aag gtc gtc gtc acc cac tcc gcc        486
Lys Gln Phe Ser Ala Ser Gly Ala Lys Val Val Val Thr His Ser Ala
```

```
              135                 140                 145
tac gtc gcc aag ctc cgg cac ggc gcc ttc ccg agg atc ggc acg gtg       534
Tyr Val Ala Lys Leu Arg His Gly Ala Phe Pro Arg Ile Gly Thr Val
    150                 155                 160 agc ggc ggc ggt gtg gac ggc aat gcc ctc ctc acc gtc ctc acc atc       582
Ser Gly Gly Gly Val Asp Gly Asn Ala Leu Leu Thr Val Leu Thr Ile
165                 170                 175                 180 gac ggc gac gcg gcc gac acc ccg gaa ggc tgc ctg gcg ttc tgg gag       630
Asp Gly Asp Ala Ala Asp Thr Pro Glu Gly Cys Leu Ala Phe Trp Glu
                185                 190                 195 ctc ctc acg tcc ggc gac ggc gac gcc ctc ccg gag gtg tcc atc tcc       678
Leu Leu Thr Ser Gly Asp Gly Asp Ala Leu Pro Glu Val Ser Ile Ser
                200                 205                 210 ccg gac gac ccc gtg gcg ctg ccg ttc tcg tcg ggc acc acg ggg ctg       726
Pro Asp Asp Pro Val Ala Leu Pro Phe Ser Ser Gly Thr Thr Gly Leu
                215                 220                 225 ccc aag ggc gtc gtg ctg acc cac ggc ggc cag gtc acg aac gtg gcg       774
Pro Lys Gly Val Val Leu Thr His Gly Gly Gln Val Thr Asn Val Ala
230                 235                 240 cag cag gtg gac ggc gcg aac ccc aac ctg tac atg cgg gag ggc gac       822
Gln Gln Val Asp Gly Ala Asn Pro Asn Leu Tyr Met Arg Glu Gly Asp
245                 250                 255                 260 gtc gcg ctc tgc gtg ctg cct ctg ttc cac atc ttc tcc ctc aac tcc       870
Val Ala Leu Cys Val Leu Pro Leu Phe His Ile Phe Ser Leu Asn Ser
                265                 270                 275 gtg ctg ctc tgc gcc atg cgg gcc ggc gcg gcg gtc atg ctc atg ccc       918
Val Leu Leu Cys Ala Met Arg Ala Gly Ala Ala Val Met Leu Met Pro
                280                 285                 290 aag ttc gag atg ggc gcc atg ctg gag ggc atc cag cgg tgg cgc gtc       966
Lys Phe Glu Met Gly Ala Met Leu Glu Gly Ile Gln Arg Trp Arg Val
            295                 300                 305 aca gtg gca gcc gtc gtg ccg ccg ctg gtg ctc gcc ctg gcc aag aac      1014
Thr Val Ala Ala Val Val Pro Pro Leu Val Leu Ala Leu Ala Lys Asn
310                 315                 320 ccc gcg ctc gag aag tac gac ctc agc tcc atc cgg atc gtg ctc tcc      1062
Pro Ala Leu Glu Lys Tyr Asp Leu Ser Ser Ile Arg Ile Val Leu Ser
325                 330                 335                 340 ggc gcc gcg ccg ctt ggc aag gac ctc gtc gac gca ctc cgc gcc cgc      1110
Gly Ala Ala Pro Leu Gly Lys Asp Leu Val Asp Ala Leu Arg Ala Arg
                345                 350                 355 gtg cca cag gcc gtc ttc gga cag gga tac ggg atg acg gag gcc ggg      1158
Val Pro Gln Ala Val Phe Gly Gln Gly Tyr Gly Met Thr Glu Ala Gly
                360                 365                 370 ccc gtg ctg tcc atg tgc ccg gcg ttc gcc aag gag ccg gcg ccc gcc      1206
Pro Val Leu Ser Met Cys Pro Ala Phe Ala Lys Glu Pro Ala Pro Ala
                375                 380                 385 aag ccg ggg tcg tgc ggc aca gtg gtg cgc aac gcg gag ctc aag gtg      1254
Lys Pro Gly Ser Cys Gly Thr Val Val Arg Asn Ala Glu Leu Lys Val
        390                 395                 400 gtg gac ccg gac acg ggc ctc tcc ctc ggc cgc aac ctc ccc ggc gag      1302
Val Asp Pro Asp Thr Gly Leu Ser Leu Gly Arg Asn Leu Pro Gly Glu
405                 410                 415                 420 atc tgc atc cgg ggc ccg cag atc atg aaa ggg tac ctg aac gac ccg      1350
Ile Cys Ile Arg Gly Pro Gln Ile Met Lys Gly Tyr Leu Asn Asp Pro
                425                 430                 435 gag gcc acc gcg agg acg atc gac gtc cac ggc tgg ctc cac acc ggc      1398
Glu Ala Thr Ala Arg Thr Ile Asp Val His Gly Trp Leu His Thr Gly
                440                 445                 450 gac atc ggc tac gtc gac gac gac gac gag gtc ttc atc gtc gac cgc      1446
Asp Ile Gly Tyr Val Asp Asp Asp Asp Glu Val Phe Ile Val Asp Arg
```

-continued

```
Asp Ile Gly Tyr Val Asp Asp Asp Glu Val Phe Ile Val Asp Arg
        455                 460                 465 gtc aag gag ctc atc aag ttc aag ggc ttc cag gtg ccg ccg gcc gag    1494
Val Lys Glu Leu Ile Lys Phe Lys Gly Phe Gln Val Pro Pro Ala Glu
    470                 475                 480 ctc gag gct ctg ctc gtc gcc cac ccg tcc atc gcc gac gcg gcc gtc    1542
Leu Glu Ala Leu Leu Val Ala His Pro Ser Ile Ala Asp Ala Ala Val
485                 490                 495                 500 gtc ccg caa aag gac gaa gcc gcc ggc gag gtc ccc gtc gcc ttc gtg    1590
Val Pro Gln Lys Asp Glu Ala Ala Gly Glu Val Pro Val Ala Phe Val
                505                 510                 515 gtc cgc gcc gcc gac gcc gac atc gcg gag gac gcc atc aag gag ttc    1638
Val Arg Ala Ala Asp Ala Asp Ile Ala Glu Asp Ala Ile Lys Glu Phe
            520                 525                 530 atc tcc aag cag gtg gta tta tac aag agg ata cac aag gtg tac ttc    1686
Ile Ser Lys Gln Val Val Leu Tyr Lys Arg Ile His Lys Val Tyr Phe
        535                 540                 545 acc ccc tcc atc ccc aag tcg gcg tcc ggg aag atc ctg agg agg gag    1734
Thr Pro Ser Ile Pro Lys Ser Ala Ser Gly Lys Ile Leu Arg Arg Glu
    550                 555                 560 ctg cgc gcc aag ctc gcg gca gcc gcg acc gcc tgaggagctt gacgctcagg   1787
Leu Arg Ala Lys Leu Ala Ala Ala Thr Ala
565                 570                 575 ttccatgcct tgctacgtgc aactcgtttg gtagtggcgt ttactgccaa tccagtgtat    1847
gggtacaggc gtgaaacatg aggtaccgag aatgtactat caatatatgc tttgtatgcg    1907
agtgcttcgt caattaagga ccaccattta ttcccgtcat gattttattt ccaaaaaaaa    1967
aaa                                                                  1970

<210> SEQ ID NO 22
<211> LENGTH: 1269
<212> TYPE: DNA
<213> ORGANISM: Zea mays
<220> FEATURE:
<221> NAME/KEY: CDS
<222> LOCATION: (56)...(1117)

<400> SEQUENCE: 22
actagtggat ccaaagaatt cggcacgagg agagatcagc gacttaacaa caata atg    58
                                                              Met
                                                                1 gcc acc gcc ata gtt ccc acg gac gcc gag ctg ctg cag gcg cag gcc    106
Ala Thr Ala Ile Val Pro Thr Asp Ala Glu Leu Leu Gln Ala Gln Ala
        5                   10                  15 gac ctg tgg cgc cac agc ctc tac tac ctg aca tcc atg gcg ctc aag    154
Asp Leu Trp Arg His Ser Leu Tyr Tyr Leu Thr Ser Met Ala Leu Lys
    20                  25                  30 tgc gcg gtg gag ctc cac atc ccg acc gcc atc cac aac cta ggc ggg    202
Cys Ala Val Glu Leu His Ile Pro Thr Ala Ile His Asn Leu Gly Gly
35                  40                  45 tct gcc acg ctg ccg gac ctc gtg gcc gcg ctg tcc ctg cca gcg gcc    250
Ser Ala Thr Leu Pro Asp Leu Val Ala Ala Leu Ser Leu Pro Ala Ala
50                  55                  60                  65 aag ctc ccg ttc ctc ggg cgc gtg atg cgg ctg ctg gtc acg tcg ggc    298
Lys Leu Pro Phe Leu Gly Arg Val Met Arg Leu Leu Val Thr Ser Gly
                70                  75                  80 gtc ttc gcg tcg tcc gac gac gtg cag tac cgg ctg aac ccg ctg tcc    346
Val Phe Ala Ser Ser Asp Asp Val Gln Tyr Arg Leu Asn Pro Leu Ser
            85                  90                  95 tgg ctg ctg gtg gag ggc gtg gag tcg gag gac cac acc tac cag aag    394
```

-continued

```
Trp Leu Leu Val Glu Gly Val Glu Ser Glu Asp His Thr Tyr Gln Lys
        100                 105                 110 tac ttc gtg ctg ggc acc gtc tcc cgc cac tac gtg gag gcc ggc atg      442
Tyr Phe Val Leu Gly Thr Val Ser Arg His Tyr Val Glu Ala Gly Met
    115                 120                 125 tcc ctg gcc gac tgg ttc aag aag gag gag gac gag gac cgc cag ctg      490
Ser Leu Ala Asp Trp Phe Lys Lys Glu Glu Asp Glu Asp Arg Gln Leu
130                 135                 140                 145 ccg tcg ccg ttc gag gcc ctg cac ggg gtg ccc ctc gtc cac gag agc      538
Pro Ser Pro Phe Glu Ala Leu His Gly Val Pro Leu Val His Glu Ser
                150                 155                 160 acc aag ctg ctg gac gag gag ctg gac agg gtc gtg gag gaa ggc gtg      586
Thr Lys Leu Leu Asp Glu Glu Leu Asp Arg Val Val Glu Glu Gly Val
        165                 170                 175 gcc gcg cac gac aac ctg gcc atc ggg acc gtc ata cgg gag tgc ggc      634
Ala Ala His Asp Asn Leu Ala Ile Gly Thr Val Ile Arg Glu Cys Gly
    180                 185                 190 gcc gac gtc ttc agc ggc ctc cgc tcg ctc acc tac tgc tgc ggc agg      682
Ala Asp Val Phe Ser Gly Leu Arg Ser Leu Thr Tyr Cys Cys Gly Arg
195                 200                 205 cag ggg aac gcc agc gcg gcc gcc atc gtc aag gcc ttc cca gac atc      730
Gln Gly Asn Ala Ser Ala Ala Ala Ile Val Lys Ala Phe Pro Asp Ile
210                 215                 220                 225 aag tgc acc gtg ctc aac ctt ccc agg gtc gtc gag gag acg acg acc      778
Lys Cys Thr Val Leu Asn Leu Pro Arg Val Val Glu Glu Thr Thr Thr
                230                 235                 240 aag acc atc acc atc ccg cct gcg cag gct gtc atg ctc aag ctc gtc      826
Lys Thr Ile Thr Ile Pro Pro Ala Gln Ala Val Met Leu Lys Leu Val
        245                 250                 255 ctg cac ttc tgg agc gac gac gac tgc gtc aag atc ctg gag ctg tgc      874
Leu His Phe Trp Ser Asp Asp Asp Cys Val Lys Ile Leu Glu Leu Cys
    260                 265                 270 agg aag gcc atc cct tcc cgc caa gaa gga ggg aag gtg atc atc att      922
Arg Lys Ala Ile Pro Ser Arg Gln Glu Gly Gly Lys Val Ile Ile Ile
275                 280                 285 gag ata ctc ctg ggc ccg tac atg ggg ccg gtc atg tac gag gcc cag      970
Glu Ile Leu Leu Gly Pro Tyr Met Gly Pro Val Met Tyr Glu Ala Gln
290                 295                 300                 305 ctg ctg atg gac atg ctc atg atg gtg aac acc aag ggc agg cag cgc     1018
Leu Leu Met Asp Met Leu Met Met Val Asn Thr Lys Gly Arg Gln Arg
                310                 315                 320 ggc gaa gac gac tgg cgc cac atc ttt acc aag gct ggc ttc tcc gac     1066
Gly Glu Asp Asp Trp Arg His Ile Phe Thr Lys Ala Gly Phe Ser Asp
        325                 330                 335 tac aag gtt gtc aag aaa atc gga gct cgt ggt gtc atc gag gtc tac     1114
Tyr Lys Val Val Lys Lys Ile Gly Ala Arg Gly Val Ile Glu Val Tyr
    340                 345                 350 cca tgatccatga tcgatgtcat gtgactgtga gaggacgata ctgtacaatt          1167
Pro aaataaacgg ggtatctagc tactactcag cttttgtacc tcgagatcca tgcatgttaa   1227
ttacttgctt ccatctgttt tcaaaatgca tctatgtaat gt                      1269
```

<210> SEQ ID NO 23
<211> LENGTH: 1412
<212> TYPE: DNA
<213> ORGANISM: Zea mays
<220> FEATURE:
<221> NAME/KEY: CDS
<222> LOCATION: (139)...(1263)

<400> SEQUENCE: 23

```
gtcgacccac gcgtccgcca ggttccattc gtctctgcag tctcacccac aagagacaca      60
aacctagcgc aacaagcaat cgaaaaagag atttggctac aaccaattaa ccattggcca     120
gcagtgtacg tgggaacg atg gcc ctc atg cag gag agt agt agc cag gat       171
                    Met Ala Leu Met Gln Glu Ser Ser Ser Gln Asp
                     1               5                        10 ttg ctc caa gct cac gac gag ctc ttg cac cat tcc ctg tgc ttc gcc       219
Leu Leu Gln Ala His Asp Glu Leu Leu His His Ser Leu Cys Phe Ala
             15                  20                  25 aaa tcg ctc gcg ctc gcc gtg gcg ctg gac ctc cgc atc ccc gac gcg       267
Lys Ser Leu Ala Leu Ala Val Ala Leu Asp Leu Arg Ile Pro Asp Ala
         30                  35                  40 atc cac cac cac ggg gcc ggc ggc gcc acc ctt ctc cag atc ctc gcc       315
Ile His His His Gly Ala Gly Gly Ala Thr Leu Leu Gln Ile Leu Ala
     45                  50                  55 gag act gcg ctc cac cca agc aag ctt cgc gcc ctt cgc cgc ctc atg       363
Glu Thr Ala Leu His Pro Ser Lys Leu Arg Ala Leu Arg Arg Leu Met
 60                  65                  70                  75 cgc gtg ctc acc gtc acg ggc atc ttc agc gtc gtc gag caa cca cca       411
Arg Val Leu Thr Val Thr Gly Ile Phe Ser Val Val Glu Gln Pro Pro
                 80                  85                  90 gca ggt ggt ggt gat gat tca acc gtc cac acg tcg gac gac gaa gct       459
Ala Gly Gly Gly Asp Asp Ser Thr Val His Thr Ser Asp Asp Glu Ala
             95                 100                 105 gtc gtc gtc tac agg ttg acg gca gcc tcc cgc ttc ctc gtc agc gac       507
Val Val Val Tyr Arg Leu Thr Ala Ala Ser Arg Phe Leu Val Ser Asp
         110                 115                 120 gac gtg agc acg gcg acc ttg gct ccc ttt gtg agt ctg gcg ctc cag       555
Asp Val Ser Thr Ala Thr Leu Ala Pro Phe Val Ser Leu Ala Leu Gln
125                 130                 135 cct atc gct gcc tgt ccg cac gcc ctg ggt atc tcc gcg tgg ttc cgg       603
Pro Ile Ala Ala Cys Pro His Ala Leu Gly Ile Ser Ala Trp Phe Arg
140                 145                 150                 155 cag gag cag cac gag ccg tcc ccg tat ggc ctg gcg ttc cgc cag acc       651
Gln Glu Gln His Glu Pro Ser Pro Tyr Gly Leu Ala Phe Arg Gln Thr
                160                 165                 170 cca acg atc tgg gaa cat gct gac gac gta aac gcc ttg ctg aac aaa       699
Pro Thr Ile Trp Glu His Ala Asp Asp Val Asn Ala Leu Leu Asn Lys
            175                 180                 185 ggc atg gcc gcg gac agc cgc ttc ctc atg cca att gtg ctg agg gag       747
Gly Met Ala Ala Asp Ser Arg Phe Leu Met Pro Ile Val Leu Arg Glu
        190                 195                 200 tgc ggc gag acg ttt cgt ggg atc gac tcg ttg gtt gac gtc ggt ggt       795
Cys Gly Glu Thr Phe Arg Gly Ile Asp Ser Leu Val Asp Val Gly Gly
205                 210                 215 ggc cat ggt ggc gcc gcc gcc acc atc gcc gcc gcc ttc ccc cac ctc       843
Gly His Gly Gly Ala Ala Ala Thr Ile Ala Ala Ala Phe Pro His Leu
220                 225                 230                 235 aag tgc agc gtg ctt gac ctc ccg cac gtt gtc gcc ggt gct ccg tct       891
Lys Cys Ser Val Leu Asp Leu Pro His Val Val Ala Gly Ala Pro Ser
                240                 245                 250 gat ggc aac gtg cag ttc gtc gca ggc aat atg ttt gag agt att cca       939
Asp Gly Asn Val Gln Phe Val Ala Gly Asn Met Phe Glu Ser Ile Pro
            255                 260                 265 cct gca acc gct gtt ttc ctc aag aaa act cta cat gac tgg ggt gac       987
Pro Ala Thr Ala Val Phe Leu Lys Lys Thr Leu His Asp Trp Gly Asp
        270                 275                 280 gat gag tgt gtc aag ata ttg aag aat tgc aag caa gcc ata tct cca      1035
```

```
                Asp Glu Cys Val Lys Ile Leu Lys Asn Cys Lys Gln Ala Ile Ser Pro
                    285                 290                 295 cgg gat gca ggt ggg aag gta ata atc ttg gat gtg gta gtt gga tat          1083
Arg Asp Ala Gly Gly Lys Val Ile Ile Leu Asp Val Val Val Gly Tyr
300                 305                 310                 315 aaa cag tca aac ata aag cat caa gag aca caa gtt atg ttt gat ttg          1131
Lys Gln Ser Asn Ile Lys His Gln Glu Thr Gln Val Met Phe Asp Leu
                320                 325                 330 tat atg atg gcg gtt aac gga gtt gag cgt gac gag caa gag tgg aag          1179
Tyr Met Met Ala Val Asn Gly Val Glu Arg Asp Glu Gln Glu Trp Lys
            335                 340                 345 aag atc ttc act gaa gct gga ttc aaa gac tac aaa att cta ccc gtc          1227
Lys Ile Phe Thr Glu Ala Gly Phe Lys Asp Tyr Lys Ile Leu Pro Val
        350                 355                 360 att ggt gat gta tcg gtc atc atc gag gtc tat cct tgaatgcttt              1273
Ile Gly Asp Val Ser Val Ile Ile Glu Val Tyr Pro
365                 370                 375 gtgaacaaag gcctccataa taaactgaag accaagaggt gttgatagta tattatgaat       1333
tgttatttgt cctgtacact tgattctttg cgtatttgta atgacaagtt gagtaaaaaa       1393
aaaaaaaaag ggcggccgc                                                    1412

<210> SEQ ID NO 24
<211> LENGTH: 1315
<212> TYPE: DNA
<213> ORGANISM: Zea mays
<220> FEATURE:
<221> NAME/KEY: CDS
<222> LOCATION: (51)...(1160)

<400> SEQUENCE: 24
ccacgcgtcc gagccaacta gcagtatata cgttggcacg cacgaatacg atg gca           56
                                                         Met Ala
                                                           1 ctc atg caa gag agc agt agc cag gac cag gac atg ctc caa gct cac          104
Leu Met Gln Glu Ser Ser Ser Gln Asp Gln Asp Met Leu Gln Ala His
        5                   10                  15 gac gag ctc ttg cac cat tcc ttg tgc ttc gcc aaa tcg ctc gcg ctc          152
Asp Glu Leu Leu His His Ser Leu Cys Phe Ala Lys Ser Leu Ala Leu
    20                  25                  30 acc gtg gcg ctg gac ctc cgc atc cca gac gcc atc cac cac cac ggc          200
Thr Val Ala Leu Asp Leu Arg Ile Pro Asp Ala Ile His His His Gly
35                  40                  45                  50 ggc ggc gcc acc ctt ctc cag atc ctc gcg gag act ggg ctc cac cca          248
Gly Gly Ala Thr Leu Leu Gln Ile Leu Ala Glu Thr Gly Leu His Pro
                55                  60                  65 agc aag ctt cgc gcc cta cgc cgc ctc atg cgc gtg ctc acc gtc acg          296
Ser Lys Leu Arg Ala Leu Arg Arg Leu Met Arg Val Leu Thr Val Thr
            70                  75                  80 ggc acc ttc agc gtc cag gtc cag caa cca cca gcc ggt agt gac gac          344
Gly Thr Phe Ser Val Gln Val Gln Gln Pro Pro Ala Gly Ser Asp Asp
        85                  90                  95 gac gaa gct gtc gtc gtc tac agg ctg aca gca gcc tcc cgc ttc ctc          392
Asp Glu Ala Val Val Val Tyr Arg Leu Thr Ala Ala Ser Arg Phe Leu
    100                 105                 110 gtc agc gac gag gtg agc acg gca aca acc ttg gct ccc ttt gtg agc          440
Val Ser Asp Glu Val Ser Thr Ala Thr Thr Leu Ala Pro Phe Val Ser
115                 120                 125                 130 ctg gcg ctc cag cct atc gct gcc tct ccg cac gcc cta ggc atc tgc          488
Leu Ala Leu Gln Pro Ile Ala Ala Ser Pro His Ala Leu Gly Ile Cys
                135                 140                 145
```

```
gcg tgg ttt cgg cag gag cag cac gag ccg tcc ccg tat ggc ctg gca        536
Ala Trp Phe Arg Gln Glu Gln His Glu Pro Ser Pro Tyr Gly Leu Ala
            150                 155                 160 ttc cgc cag acc cca acg ctc tgg gaa cat gct gac gac gta aac gcc        584
Phe Arg Gln Thr Pro Thr Leu Trp Glu His Ala Asp Asp Val Asn Ala
        165                 170                 175 tta ctg aac aaa ggc atg gtg gcg gac agc cgc ttc ctg atg cca att        632
Leu Leu Asn Lys Gly Met Val Ala Asp Ser Arg Phe Leu Met Pro Ile
    180                 185                 190 gtg ctc agg cag tgc ggc gag atg ttt cgt ggg atc aac tca ttg gtt        680
Val Leu Arg Gln Cys Gly Glu Met Phe Arg Gly Ile Asn Ser Leu Val
195                 200                 205                 210 gac gtc ggc ggt ggg cat ggt ggc gcc gcc gcc gcc atc gcc gct gcc        728
Asp Val Gly Gly Gly His Gly Gly Ala Ala Ala Ala Ile Ala Ala Ala
                215                 220                 225 ttc ccg cac gtc aag tgc agc gtg ctt gac ctc ccg cac gtt gtc gcc        776
Phe Pro His Val Lys Cys Ser Val Leu Asp Leu Pro His Val Val Ala
            230                 235                 240 ggt gct cca tct gat ggc aac gtg cag ttc gtc gca gga aat atg ttt        824
Gly Ala Pro Ser Asp Gly Asn Val Gln Phe Val Ala Gly Asn Met Phe
        245                 250                 255 gag agt att cca cct gca acc gct gtt ttc ctc aag aaa act cta cat        872
Glu Ser Ile Pro Pro Ala Thr Ala Val Phe Leu Lys Lys Thr Leu His
    260                 265                 270 gac tgg ggt gac gat gag tgt gtc aag ata ttg aag aat tgc aag caa        920
Asp Trp Gly Asp Asp Glu Cys Val Lys Ile Leu Lys Asn Cys Lys Gln
275                 280                 285                 290 gcc ata cct cca cgg gat gca ggt gga aag gta ata atc ttg gac gtg        968
Ala Ile Pro Pro Arg Asp Ala Gly Gly Lys Val Ile Ile Leu Asp Val
                295                 300                 305 gta gtt gga tat aaa cag tca aac ata aag cat caa gag aca caa gtt       1016
Val Val Gly Tyr Lys Gln Ser Asn Ile Lys His Gln Glu Thr Gln Val
            310                 315                 320 atg ttc gat ttg tat atg atg gcc gtt aac gga gtt gag cgt gac gag       1064
Met Phe Asp Leu Tyr Met Met Ala Val Asn Gly Val Glu Arg Asp Glu
        325                 330                 335 caa gag tgg aag aag atc ttc gcc gaa gcc gga ttc aaa gac tac aaa       1112
Gln Glu Trp Lys Lys Ile Phe Ala Glu Ala Gly Phe Lys Asp Tyr Lys
    340                 345                 350 att cta ccc gtc att ggt gac gtg tcg gtc atc atc gag gtc tat cct       1160
Ile Leu Pro Val Ile Gly Asp Val Ser Val Ile Ile Glu Val Tyr Pro
355                 360                 365                 370 tgaatgcttt atttgtgaat aataaagggc gcctaattca taataaacct aggattgtga    1220
aggcgctggt attacattaa gaattgttcc tttttattac catgtgcttg aacctttgga    1280
caatttgtaa tatgagaagg tgagcaattg tgttt                               1315

<210> SEQ ID NO 25
<211> LENGTH: 1306
<212> TYPE: DNA
<213> ORGANISM: Zea mays
<220> FEATURE:
<221> NAME/KEY: CDS
<222> LOCATION: (57)...(1154)

<400> SEQUENCE: 25
ccacgcgtcc ggagaattag ctatagccag ccgtgtgtcg aacacgacac gcgata atg      59
                                                                 Met
                                                                  1 gca ctc atg cag gag agc agc cag gac ttg ctc gaa gcg cac gac gag       107
```

-continued

```
                Ala Leu Met Gln Glu Ser Ser Gln Asp Leu Leu Glu Ala His Asp Glu
                             5                  10                  15 ctc ttc cac cac tgc ctg tgc ttc gcc aaa tcg ctc gcg ctc gcc gtg            155
Leu Phe His His Cys Leu Cys Phe Ala Lys Ser Leu Ala Leu Ala Val
             20                  25                  30 gcg cag gac ctc cgc atc ccc gac gcg atc cac cac cac gga ggc ggc            203
Ala Gln Asp Leu Arg Ile Pro Asp Ala Ile His His His Gly Gly Gly
         35                  40                  45 gcc acc ctc cac cag atc ctc gcc gag gcc gcg ctc cac cca agc aag            251
Ala Thr Leu His Gln Ile Leu Ala Glu Ala Ala Leu His Pro Ser Lys
 50                  55                  60                  65 ctt cgc gcc cta cgc cgc ctg atg cgc gtg ctc acc gtc tcg ggc gtc            299
Leu Arg Ala Leu Arg Arg Leu Met Arg Val Leu Thr Val Ser Gly Val
                 70                  75                  80 ttc acc gtc cag tat tct tca acc gtc gac gcg tcg gac gga gct gat            347
Phe Thr Val Gln Tyr Ser Ser Thr Val Asp Ala Ser Asp Gly Ala Asp
             85                  90                  95 gtc gtc tac agg ctg acg gca gcc tcc cgc ttc ctc gtc agc gat agc            395
Val Val Tyr Arg Leu Thr Ala Ala Ser Arg Phe Leu Val Ser Asp Ser
        100                 105                 110 gac gag gcg ggc acg gcg tcc ttg gct ccc ttt gcg aac ctg gcg ctc            443
Asp Glu Ala Gly Thr Ala Ser Leu Ala Pro Phe Ala Asn Leu Ala Leu
        115                 120                 125 cac cct atc gcc atc tcc ccg cac gcc gtg ggc atc tgc gcg tgg ttc            491
His Pro Ile Ala Ile Ser Pro His Ala Val Gly Ile Cys Ala Trp Phe
130                 135                 140                 145 cgg cag gag cag cac gac ccg tcc ccg tac ggc ctg gcg ttc cgc cag            539
Arg Gln Glu Gln His Asp Pro Ser Pro Tyr Gly Leu Ala Phe Arg Gln
                150                 155                 160 atc ccg acc atc tgg gag cat gct gac aac gta aac gcc cta ctg aac            587
Ile Pro Thr Ile Trp Glu His Ala Asp Asn Val Asn Ala Leu Leu Asn
            165                 170                 175 aaa ggc ttg ctc gcg gaa agc cgc ttc ttg atg cca atc gta ctc agg            635
Lys Gly Leu Leu Ala Glu Ser Arg Phe Leu Met Pro Ile Val Leu Arg
        180                 185                 190 gag tgc gga gac gag gtg ttc cgt ggg atc gac tcg ttg gtc gac gtc            683
Glu Cys Gly Asp Glu Val Phe Arg Gly Ile Asp Ser Leu Val Asp Val
        195                 200                 205 ggc ggt ggg cac ggt ggc gcc gcc gcc acc atc gcc gcc gca ttc ccg            731
Gly Gly Gly His Gly Gly Ala Ala Ala Thr Ile Ala Ala Ala Phe Pro
210                 215                 220                 225 cac gtc aag tgc agc gtg ctt gac ctc ccg cac gtt gtc gcc ggt gct            779
His Val Lys Cys Ser Val Leu Asp Leu Pro His Val Val Ala Gly Ala
                230                 235                 240 cca tcc gat gcc tgc gtg cag ttc gtt gcg ggc aat atg ttc cac agt            827
Pro Ser Asp Ala Cys Val Gln Phe Val Ala Gly Asn Met Phe His Ser
            245                 250                 255 att cca cct gca acc gcc gtt ttc ttc aag aca act cta tgt gac tgg            875
Ile Pro Pro Ala Thr Ala Val Phe Phe Lys Thr Thr Leu Cys Asp Trp
        260                 265                 270 ggt gac gac gag tgc atc aag ata ttg aag aat tgc aag caa gcc ata            923
Gly Asp Asp Glu Cys Ile Lys Ile Leu Lys Asn Cys Lys Gln Ala Ile
275                 280                 285 tct cca cgg gat gag ggt ggg aag gta ata atc atg gac gtg gta gtc            971
Ser Pro Arg Asp Glu Gly Gly Lys Val Ile Ile Met Asp Val Val Val
290                 295                 300                 305 ggg tat ggg cag tca aac atg aag cgc cta gag aca caa gtt atg ttt           1019
Gly Tyr Gly Gln Ser Asn Met Lys Arg Leu Glu Thr Gln Val Met Phe
                310                 315                 320
```

-continued

```
gat ttg gtt atg atg gcg gtc aat gga gtc gag cgc gac gag caa gag      1067
Asp Leu Val Met Met Ala Val Asn Gly Val Glu Arg Asp Glu Gln Glu
            325                 330                 335 tgg aag gag atg ttc att gaa gct gga ttc aaa gac tac aaa atc cga      1115
Trp Lys Glu Met Phe Ile Glu Ala Gly Phe Lys Asp Tyr Lys Ile Arg
    340                 345                 350 cca gta gct ggc ctc atg tcg gtc atc gag gtc tat cca tgaattcttt      1164
Pro Val Ala Gly Leu Met Ser Val Ile Glu Val Tyr Pro
355                 360                 365 gtgaacaaaa ggccggctgc cataatataa actgaagacc acgacgtcgt catggagctg   1224
agcgtgttgt tttttagact actaggcact tgagcctctg agaatttgta ataataaata   1284
agctgagcaa cagcgttctg tt                                            1306

<210> SEQ ID NO 26
<211> LENGTH: 1794
<212> TYPE: DNA
<213> ORGANISM: Zea mays
<220> FEATURE:
<221> NAME/KEY: CDS
<222> LOCATION: (80)...(1594)
<220> FEATURE:
<221> NAME/KEY: misc_feature
<222> LOCATION: (1)...(1794)
<223> OTHER INFORMATION: n = A,T,C or G

<400> SEQUENCE: 26
gcgccacgcc acacaaaaag cagtgactga gtgagaaagg acagcaagca agccctccct    60
ccatctccgc cccgtcgcc atg gtc ctt ctc ttc gtg gag aag ctc ctg gtc   112
                     Met Val Leu Leu Phe Val Glu Lys Leu Leu Val
                      1               5                   10 ggc ctc ttg gcg tcc gtc atg gtc gcc atc gcg gtg tcc aag atc cgt    160
Gly Leu Leu Ala Ser Val Met Val Ala Ile Ala Val Ser Lys Ile Arg
            15                  20                  25 ggc cgc aag ctc cgg ctg cct ccc ggc ccc gtc ccc gtg ccc gtc ttc    208
Gly Arg Lys Leu Arg Leu Pro Pro Gly Pro Val Pro Val Pro Val Phe
        30                  35                  40 ggg aac tgg ctg cag gtc ggc gac gac ctc aac cac cgc aac ctc gcc    256
Gly Asn Trp Leu Gln Val Gly Asp Asp Leu Asn His Arg Asn Leu Ala
    45                  50                  55 gcg ctg tcc cgc aag ttc ggc gac gtc ttc ctc ctc cgg atg ggg cag    304
Ala Leu Ser Arg Lys Phe Gly Asp Val Phe Leu Leu Arg Met Gly Gln
60                  65                  70                  75 cgc aac ctg gtg gtg gtc tcg tcg ccg ccg ctg gcg cgg gag gtg ctc    352
Arg Asn Leu Val Val Val Ser Ser Pro Pro Leu Ala Arg Glu Val Leu
                80                  85                  90 cac acg cag ggc gtg gag ttc ggc tcc cgc acc cgc aac gtg gtc ttc    400
His Thr Gln Gly Val Glu Phe Gly Ser Arg Thr Arg Asn Val Val Phe
            95                  100                 105 gac atc ttc acg gac aag ggg cag gac atg gtg ttc acc gtg tac ggc    448
Asp Ile Phe Thr Asp Lys Gly Gln Asp Met Val Phe Thr Val Tyr Gly
        110                 115                 120 gac cac tgg cgc aag atg cgc cgc atc atg acc gtg ccc ttc ttc acc    496
Asp His Trp Arg Lys Met Arg Arg Ile Met Thr Val Pro Phe Phe Thr
    125                 130                 135 aac aag gtc gtg cag cag tac cgc cac ggc tgg gag gcc gag gcc gcc    544
Asn Lys Val Val Gln Gln Tyr Arg His Gly Trp Glu Ala Glu Ala Ala
140                 145                 150                 155 gcc gtc gtc gac gac gtg cgc ctc gac ccc aag gcg gcc acc gac gga    592
Ala Val Val Asp Asp Val Arg Leu Asp Pro Lys Ala Ala Thr Asp Gly
                160                 165                 170
```

| | | |
|---|---|---|
| atc gtg ctc cgc cga cgc ctg cag ctc atg atg tac aac aac gta tac<br>Ile Val Leu Arg Arg Arg Leu Gln Leu Met Met Tyr Asn Asn Val Tyr<br>            175                    180                    185 | 640 |
| cgg atc atg ttc gac cgg cgc ttc gag agc atg gac gac ccg ctc ttc<br>Arg Ile Met Phe Asp Arg Arg Phe Glu Ser Met Asp Asp Pro Leu Phe<br>       190                    195                    200 | 688 |
| ctc cgc ctc agg gcg ctc aac ggc gag cgc agc cgc ctc gcg cag agc<br>Leu Arg Leu Arg Ala Leu Asn Gly Glu Arg Ser Arg Leu Ala Gln Ser<br>205                    210                    215 | 736 |
| ttc gag tac aac tac ggc gac ttc atc ccc atc ctc cgt ccg ttc ctc<br>Phe Glu Tyr Asn Tyr Gly Asp Phe Ile Pro Ile Leu Arg Pro Phe Leu<br>220                    225                    230                    235 | 784 |
| cgc ggc tac ctc agg gtc tgc aag gag gtc aag gag acc cgc ctc aag<br>Arg Gly Tyr Leu Arg Val Cys Lys Glu Val Lys Glu Thr Arg Leu Lys<br>                    240                    245                    250 | 832 |
| ctc ttc aag gat ttc ttc ctc gag gag agg aag aag ctg gcg agc acc<br>Leu Phe Lys Asp Phe Phe Leu Glu Glu Arg Lys Lys Leu Ala Ser Thr<br>                    255                    260                    265 | 880 |
| aag gcc acg gac agc aac ggc ctc aag tgc gcc att gat cac ata ctg<br>Lys Ala Thr Asp Ser Asn Gly Leu Lys Cys Ala Ile Asp His Ile Leu<br>                  270                    275                    280 | 928 |
| gag gca cag cag aag ggt gag atc aac gag gac aac gtg ctc ttc atc<br>Glu Ala Gln Gln Lys Gly Glu Ile Asn Glu Asp Asn Val Leu Phe Ile<br>285                    290                    295 | 976 |
| gtc gag aac att aac gtt gca gcg atc gag acc acg ctg tgg tcg atc<br>Val Glu Asn Ile Asn Val Ala Ala Ile Glu Thr Thr Leu Trp Ser Ile<br>300                    305                    310                    315 | 1024 |
| gag tgg gcg gtc gct gag ctg gtg aac cac ccg gag atc cag cag aag<br>Glu Trp Ala Val Ala Glu Leu Val Asn His Pro Glu Ile Gln Gln Lys<br>                    320                    325                    330 | 1072 |
| ctg cgg cag gag ctg gac acg gtg ctc ggg ccg ggc cac cag atc acg<br>Leu Arg Gln Glu Leu Asp Thr Val Leu Gly Pro Gly His Gln Ile Thr<br>                    335                    340                    345 | 1120 |
| gag ccg gac acg cac aac ctc ccc tac ctg cag gcg gtg atc aag gag<br>Glu Pro Asp Thr His Asn Leu Pro Tyr Leu Gln Ala Val Ile Lys Glu<br>                350                    355                    360 | 1168 |
| acg ctg cgg ctg cgg atg gcc atc ccg ctg ctg gtg ccg cac atg aac<br>Thr Leu Arg Leu Arg Met Ala Ile Pro Leu Leu Val Pro His Met Asn<br>365                    370                    375 | 1216 |
| ctc cac gac gcc aag ctc ggc ggn tac gac atc ccc gcc gag agc aag<br>Leu His Asp Ala Lys Leu Gly Xaa Tyr Asp Ile Pro Ala Glu Ser Lys<br>380                    385                    390                    395 | 1264 |
| atc ctc gtc aac gcc tgg tac ctc gcc aac aac ccc gac agy tgg agg<br>Ile Leu Val Asn Ala Trp Tyr Leu Ala Asn Asn Pro Asp Xaa Trp Arg<br>                    400                    405                    410 | 1312 |
| cgg ccc gag gag ttc cgg ccc gag cga ttc ytc gag gag gag aag cac<br>Arg Pro Glu Glu Phe Arg Pro Glu Arg Phe Xaa Glu Glu Glu Lys His<br>                    415                    420                    425 | 1360 |
| gtc gag gcc aac ggc aac gac ttc agg tac ctg ccc ttc ggc gtc ggc<br>Val Glu Ala Asn Gly Asn Asp Phe Arg Tyr Leu Pro Phe Gly Val Gly<br>                430                    435                    440 | 1408 |
| cgc agg agc tgc ccc ggg atc atc ctc gcc ctg ccc atc ctc ggc atc<br>Arg Arg Ser Cys Pro Gly Ile Ile Leu Ala Leu Pro Ile Leu Gly Ile<br>445                    450                    455 | 1456 |
| acc atc ggt cgc ctc gtc cag aac ttc gag ctg ctg ccg ccg ccc ggg<br>Thr Ile Gly Arg Leu Val Gln Asn Phe Glu Leu Leu Pro Pro Pro Gly<br>460                    465                    470                    475 | 1504 |
| cag gac aag gtn gac acc acc gag aag gga ggc cag ttc agt ctc cac<br>Gln Asp Lys Xaa Asp Thr Thr Glu Lys Gly Gly Gln Phe Ser Leu His<br>                    480                    485                    490 | 1552 |

```
atc ttg aag cat tcc acc atc gtg tgc aag cca aga acg ctt    1594
Ile Leu Lys His Ser Thr Ile Val Cys Lys Pro Arg Thr Leu
            495                 500                 505 taagagcagc ccacacgtcg gttccatgcg gagcagtcga atgttntgct ccatcaccat   1654
gttattcggg cttaattaag cagtatcatt agtagacagt aggagtacag gaagaaaaaa   1714
agctntggat aatgttattt gcaacaaagg gaagggaagc gaagaatntg ataactattc   1774
aatgaagcgt tcgattnttg                                               1794

<210> SEQ ID NO 27
<211> LENGTH: 1669
<212> TYPE: DNA
<213> ORGANISM: Zea mays
<220> FEATURE:
<221> NAME/KEY: CDS
<222> LOCATION: (53)...(1555)

<400> SEQUENCE: 27
cgaacaaacc acacacccca cctaccccgg ccggaccggc aggcagcaca gc atg gac    58
                                                          Met Asp
                                                            1 ctc gcc ctc cta gag aag gcc ctg ctg ggc ctg ttc gcc gcg gct gtg     106
Leu Ala Leu Leu Glu Lys Ala Leu Leu Gly Leu Phe Ala Ala Ala Val
        5                   10                  15 gtg gcc atc gcc gtg gcc aag ctg acc ggc aag cgg tac cgc ctc cca     154
Val Ala Ile Ala Val Ala Lys Leu Thr Gly Lys Arg Tyr Arg Leu Pro
    20                  25                  30 ccg ggg ccc ccg ggc gcc ccc gtg gtg gga aac tgg ctg cag gtg ggc     202
Pro Gly Pro Pro Gly Ala Pro Val Val Gly Asn Trp Leu Gln Val Gly
 35              40                  45                  50 gac gac ctg aac cac cgc aac ctg atg gcc atg gcg aag cgg ttc ggc     250
Asp Asp Leu Asn His Arg Asn Leu Met Ala Met Ala Lys Arg Phe Gly
                55                  60                  65 gac atc ttc ctg ctg cgc atg ggc gtg cgc aac ctg gtg gtg gtg tcg     298
Asp Ile Phe Leu Leu Arg Met Gly Val Arg Asn Leu Val Val Val Ser
            70                  75                  80 acc ccg gag ctg gcc aag gag gtg ctc cac acg cag ggc gtg gag ttc     346
Thr Pro Glu Leu Ala Lys Glu Val Leu His Thr Gln Gly Val Glu Phe
        85                  90                  95 ggc tcc cgc acc cgc aac gtg gtg ttc gac atc ttc acg ggc aag ggg     394
Gly Ser Arg Thr Arg Asn Val Val Phe Asp Ile Phe Thr Gly Lys Gly
    100                 105                 110 cag gac atg gtg ttc acg gtg tac ggc gac cac tgg cgc aag atg cgg     442
Gln Asp Met Val Phe Thr Val Tyr Gly Asp His Trp Arg Lys Met Arg
115                 120                 125                 130 cgc atc atg acc gtc ccc ttc ttc acc aac aag gtg gtg gcc cag aac     490
Arg Ile Met Thr Val Pro Phe Phe Thr Asn Lys Val Val Ala Gln Asn
                135                 140                 145 cgc gcc ggg tgg gag gag gag gcc cgg ctg gtg gtg gag gac gtg agg     538
Arg Ala Gly Trp Glu Glu Glu Ala Arg Leu Val Val Glu Asp Val Arg
            150                 155                 160 aag gac ccc gag gcc gcg gcc ggc ggc gtc gtg ctc cgc cgc cgc ctc     586
Lys Asp Pro Glu Ala Ala Ala Gly Gly Val Val Leu Arg Arg Arg Leu
        165                 170                 175 cag ctg atg atg tac aac gac atg ttc cgc atc atg ttc gac cgc cgg     634
Gln Leu Met Met Tyr Asn Asp Met Phe Arg Ile Met Phe Asp Arg Arg
    180                 185                 190 ttc gac agc gag cac gac ccg ctc ttc aac aag ctc aag gcg ctc aac     682
Phe Asp Ser Glu His Asp Pro Leu Phe Asn Lys Leu Lys Ala Leu Asn
195                 200                 205                 210
```

```
gcg gag cgc agc cgc ctg tcg cag agc ttc gag tac aac tac ggc gac        730
Ala Glu Arg Ser Arg Leu Ser Gln Ser Phe Glu Tyr Asn Tyr Gly Asp
                215                 220                 225 ttc atc ccc gtg ctc cgc ccc ttc ctc cgc ggc tac ctc aac cgc tgc        778
Phe Ile Pro Val Leu Arg Pro Phe Leu Arg Gly Tyr Leu Asn Arg Cys
            230                 235                 240 cac gac ctc aag acg cgc cgc atg aag gtc ttc gag gac aac ttc gta        826
His Asp Leu Lys Thr Arg Arg Met Lys Val Phe Glu Asp Asn Phe Val
        245                 250                 255 cag gag cgc aag aag gtg atg gct cag act ggt gag atc cgg tgc gcc        874
Gln Glu Arg Lys Lys Val Met Ala Gln Thr Gly Glu Ile Arg Cys Ala
    260                 265                 270 atg gat cac atc ctc gag gcc gag agg aag ggc gag atc aac cac gac        922
Met Asp His Ile Leu Glu Ala Glu Arg Lys Gly Glu Ile Asn His Asp
275                 280                 285                 290 aac gtc ctc tac atc gtc gag aac atc aac gtc gca gcg atc gag acg        970
Asn Val Leu Tyr Ile Val Glu Asn Ile Asn Val Ala Ala Ile Glu Thr
                295                 300                 305 acg ctg tgg tcg atc gag tgg ggc atc gcc gag ctg gtg aac cac ccg       1018
Thr Leu Trp Ser Ile Glu Trp Gly Ile Ala Glu Leu Val Asn His Pro
            310                 315                 320 gcc atc cag cac aag ctc cgg gag gag ctc gcc tcg gtg ctg ggc gcc       1066
Ala Ile Gln His Lys Leu Arg Glu Glu Leu Ala Ser Val Leu Gly Ala
        325                 330                 335 ggc gtg cct gtg acg gag ccg gac ctc gag cgc ctc ccc tac ctt cag       1114
Gly Val Pro Val Thr Glu Pro Asp Leu Glu Arg Leu Pro Tyr Leu Gln
    340                 345                 350 gcc atc gtc aag gag acg ctc cgc ctc cgc atg gcc atc ccg ctg ctg       1162
Ala Ile Val Lys Glu Thr Leu Arg Leu Arg Met Ala Ile Pro Leu Leu
355                 360                 365                 370 gtc ccc cac atg aac ctc aac gac ggc aag ctc gcc ggc ttc gac atc       1210
Val Pro His Met Asn Leu Asn Asp Gly Lys Leu Ala Gly Phe Asp Ile
                375                 380                 385 ccc gcc gag tcc aag atc ctc gtc aat gcc tgg ttc ctc gcc aac gac       1258
Pro Ala Glu Ser Lys Ile Leu Val Asn Ala Trp Phe Leu Ala Asn Asp
            390                 395                 400 ccc aag agg tgg gtg cgc ccc gac gag ttc cgg ccc gag cgc ttc ctg       1306
Pro Lys Arg Trp Val Arg Pro Asp Glu Phe Arg Pro Glu Arg Phe Leu
        405                 410                 415 gag gag gag aag tcc gtg gag gcc cac ggc aac gac ttc cga ttc gtg       1354
Glu Glu Glu Lys Ser Val Glu Ala His Gly Asn Asp Phe Arg Phe Val
    420                 425                 430 ccc ttt ggg gtc ggc cgc cgg agc tgc cct ggg atc atc ctc gcg ctg       1402
Pro Phe Gly Val Gly Arg Arg Ser Cys Pro Gly Ile Ile Leu Ala Leu
435                 440                 445                 450 cct atc atc ggc atc acc ctg ggc cgg ctg gtg cag aac ttc cag ctg       1450
Pro Ile Ile Gly Ile Thr Leu Gly Arg Leu Val Gln Asn Phe Gln Leu
                455                 460                 465 ctg ccg ccg ccg ggg ctg gac aag atc gac acc acg gag aag ccc ggc       1498
Leu Pro Pro Pro Gly Leu Asp Lys Ile Asp Thr Thr Glu Lys Pro Gly
            470                 475                 480 cag ttc agc aac cag atc gcc aag cat gcc acc atc gtc tgc aag ccc       1546
Gln Phe Ser Asn Gln Ile Ala Lys His Ala Thr Ile Val Cys Lys Pro
        485                 490                 495 ctc gag gcc tagaaatcaa tgcgtgtttc ctgcacgcgc ccccgcagat              1595
Leu Glu Ala
    500 gaagcactat gtattttctc tttttttttgt gtgttgtgtt tttttttacta agaggagatg   1655
```

-continued

```
tatttcttgt tcgt                                                    1669
```

<210> SEQ ID NO 28
<211> LENGTH: 1356
<212> TYPE: DNA
<213> ORGANISM: Zea mays
<220> FEATURE:
<221> NAME/KEY: CDS
<222> LOCATION: (135)...(1244)

<400> SEQUENCE: 28

```
tcgacccacg cgtccgccgc caatcgcagt atcggcaccg ttcttccccg cttctccagt    60
ccagctcacc agccgccccc cctccgctgc tgacactgcg aagtgcgaat caaagccacc   120
accgcgcaca aacc atg gca ccg gtg gag gcg gag cag cac cgg cgg agg    170
              Met Ala Pro Val Glu Ala Glu Gln His Arg Arg Arg
                1               5                  10 gcg ttg gcg ctc gcg gcg cac gac gcc tcc ggc gcc gtc tcc ccc atc    218
Ala Leu Ala Leu Ala Ala His Asp Ala Ser Gly Ala Val Ser Pro Ile
         15                  20                  25 cgc atc tcg cga agg gac act gga gat gac gat gtt gcc ata cag ata    266
Arg Ile Ser Arg Arg Asp Thr Gly Asp Asp Asp Val Ala Ile Gln Ile
     30                  35                  40 ctg tac tgc ggg ata tgc cac tct gac ctg cac acc atc aag aac gag    314
Leu Tyr Cys Gly Ile Cys His Ser Asp Leu His Thr Ile Lys Asn Glu
 45                  50                  55                  60 tgg aag aac gcc aac tac cct gtt gtc cct ggg cac gag atc gcc ggg    362
Trp Lys Asn Ala Asn Tyr Pro Val Val Pro Gly His Glu Ile Ala Gly
                 65                  70                  75 ctg atc acc gag gtt ggc aag aac gtg aag agg ttc aac gtc gga gac    410
Leu Ile Thr Glu Val Gly Lys Asn Val Lys Arg Phe Asn Val Gly Asp
         80                  85                  90 aag gtt ggc gtc ggg tgc atg gtc aac aca tgc cag tcc tgc gag agc    458
Lys Val Gly Val Gly Cys Met Val Asn Thr Cys Gln Ser Cys Glu Ser
     95                 100                 105 tgc gag gga ggg cac gag aac tac tgc tcc aag atc atc ttc acc tac    506
Cys Glu Gly Gly His Glu Asn Tyr Cys Ser Lys Ile Ile Phe Thr Tyr
110                 115                 120 aac tcc cac gac agg gac ggc acc gtc acc tac ggt ggc tac tct gac    554
Asn Ser His Asp Arg Asp Gly Thr Val Thr Tyr Gly Gly Tyr Ser Asp
125                 130                 135                 140 atg gtt gtc gtc aac gag cgc ttc gtc atc cgg ttc cct gat ggc atg    602
Met Val Val Val Asn Glu Arg Phe Val Ile Arg Phe Pro Asp Gly Met
                145                 150                 155 ccc ctc gac aga ggc gcg ccg ctg ctc tgt gca ggg ata acc gtg tac    650
Pro Leu Asp Arg Gly Ala Pro Leu Leu Cys Ala Gly Ile Thr Val Tyr
        160                 165                 170 aac ccc atg aag cac cac ggg cta aac gar gca ggc aag cac atc sgc    698
Asn Pro Met Lys His His Gly Leu Asn Xaa Ala Gly Lys His Ile Xaa
    175                 180                 185 gtg ktt gga ctc ggg ggg ctt ggg cac gtc gcc gtg aag ttc gcg aag    746
Val Xaa Gly Leu Gly Gly Leu Gly His Val Ala Val Lys Phe Ala Lys
190                 195                 200 gcg ttc ggg atg arg gtg acc gtg atc agc acg tcc ccg ggg aar agr    794
Ala Phe Gly Met Xaa Val Thr Val Ile Ser Thr Ser Pro Gly Xaa Xaa
205                 210                 215                 220 rrg gaa gct atg gag acg ctt ggt gca gac gcc ttt gtt gtc agc ggt    842
Xaa Glu Ala Met Glu Thr Leu Gly Ala Asp Ala Phe Val Val Ser Gly
                225                 230                 235 gat gct aac cag atg aag gct gcg aag ggc aca atg gat ggc att atg    890
Asp Ala Asn Gln Met Lys Ala Ala Lys Gly Thr Met Asp Gly Ile Met
```

-continued

```
                  240                 245                 250
aac acg gcc tct gca agc atg tcc atg tac gct tac ctt gct ctc ctc      938
Asn Thr Ala Ser Ala Ser Met Ser Met Tyr Ala Tyr Leu Ala Leu Leu
            255                 260                 265 aag ccc cag ggc aag atg atc ctg ctt ggc ctg cct gag aag cct ctg      986
Lys Pro Gln Gly Lys Met Ile Leu Leu Gly Leu Pro Glu Lys Pro Leu
        270                 275                 280 cag atc tct gcc ttc tct ttg gtt act ggg ggc aag act ctg gcc ggg     1034
Gln Ile Ser Ala Phe Ser Leu Val Thr Gly Gly Lys Thr Leu Ala Gly
285                 290                 295                 300 agc tgc atg ggg agc atc agg gac acg cag gag atg atg gac ttc gca     1082
Ser Cys Met Gly Ser Ile Arg Asp Thr Gln Glu Met Met Asp Phe Ala
                305                 310                 315 gcc aag cac ggg ttg gca gcg gac atc gaa ctg atc ggc acc gaa gaa     1130
Ala Lys His Gly Leu Ala Ala Asp Ile Glu Leu Ile Gly Thr Glu Glu
            320                 325                 330 gtt aat gag gcc atg gaa cgc ctc gcc aag ggc gag gtc agg tac cgc     1178
Val Asn Glu Ala Met Glu Arg Leu Ala Lys Gly Glu Val Arg Tyr Arg
        335                 340                 345 ttc gtc atc gac atc ggc aac acc ctc aac gcg gca tca cta ggg agc     1226
Phe Val Ile Asp Ile Gly Asn Thr Leu Asn Ala Ala Ser Leu Gly Ser
350                 355                 360 tcg ccg gtc cca gct ctg tagctgcggc acttgttgat caacaaatgc            1274
Ser Pro Val Pro Ala Leu
365             370 tcacataaac atattgttgt ttgtcgatat atcgtgcgat aagcaagtat atttggaata   1334
aaaaggaact caatttaaac gc                                             1356

<210> SEQ ID NO 29
<211> LENGTH: 1465
<212> TYPE: DNA
<213> ORGANISM: Zea mays
<220> FEATURE:
<221> NAME/KEY: CDS
<222> LOCATION: (160)...(1236)

<400> SEQUENCE: 29
ccacgcgtcc gcgtcctcgt ccccgttcca tttcattatc cccccggagc tggtgcgcga     60
gtcggagctg gtgcagggtc acccttcccc tcggcctcaa gagctctgcg gttgccgcgg    120
ccaagggcgt ccgtggagaa gcgggagcag gtggcggcg atg gaa gag caa ggc       174
                                            Met Glu Glu Gln Gly
                                             1               5 ggc cag gcg gcg ctc ggg tgg gcg gcc agg gac gac tcc ggc gtc ctc      222
Gly Gln Ala Ala Leu Gly Trp Ala Ala Arg Asp Asp Ser Gly Val Leu
            10                  15                  20 tcc ccc tac agc ttc tcc aga agg gtt cct aaa gac gac gat gtc acg      270
Ser Pro Tyr Ser Phe Ser Arg Arg Val Pro Lys Asp Asp Asp Val Thr
        25                  30                  35 atc aag gtg ctc tac tgc ggg atc tgc cac acc gac ctg cac gtc atc      318
Ile Lys Val Leu Tyr Cys Gly Ile Cys His Thr Asp Leu His Val Ile
    40                  45                  50 aag aac gac tgg cga aac gcc atg tac cca gtc gtc ccg ggg cac gag      366
Lys Asn Asp Trp Arg Asn Ala Met Tyr Pro Val Val Pro Gly His Glu
55                  60                  65 atc gtg ggc gtt gtg acc ggc gtc ggc ggc gtc acg cgg ttc aag          414
Ile Val Gly Val Val Thr Gly Val Gly Gly Val Thr Arg Phe Lys
        70                  75                  80                  85 gcc ggc gac acg gtc ggc gtg ggc tac ttc gtg ggg tcc tgc cgc tcc      462
Ala Gly Asp Thr Val Gly Val Gly Tyr Phe Val Gly Ser Cys Arg Ser
```

|  |  |  |  |  |  |  |  |  |  |  |
|---|---|---|---|---|---|---|---|---|---|---|
| | | 90 | | | 95 | | | 100 | | |
| tgc | gac | agc | tgc | ggc | aag | ggg | gac | gac | aac tac tgc gcg ggg atc gtg | 510 |
| Cys | Asp | Ser | Cys | Gly | Lys | Gly | Asp | Asp | Asn Tyr Cys Ala Gly Ile Val | |
| | | 105 | | | | 110 | | | 115 | |

```
ctc acc tcc aac ggc gtc gac cac gcg cac ggc gcg ccc acc agg        558
Leu Thr Ser Asn Gly Val Asp His Ala His Gly Gly Ala Pro Thr Arg
        120                 125                 130 ggg gga ttc tcc gac gtc ctg gtc gcg agc gag cac tac gtg gtc cgc    606
Gly Gly Phe Ser Asp Val Leu Val Ala Ser Glu His Tyr Val Val Arg
135                 140                 145 gtc ccc gac ggc ctg gcg ctg gac cgc acc gcg ccg ctg ctc tgc gcc    654
Val Pro Asp Gly Leu Ala Leu Asp Arg Thr Ala Pro Leu Leu Cys Ala
150                 155                 160                 165 ggc gtc acc gtg tac agc ccc atg atg cgc cac ggc ctc aac gag ccc    702
Gly Val Thr Val Tyr Ser Pro Met Met Arg His Gly Leu Asn Glu Pro
                170                 175                 180 ggc aag cac tcg gcg ttc gtc ggc ctc ggc ggc ctc ggc cac gtc gcc    750
Gly Lys His Ser Ala Phe Val Gly Leu Gly Gly Leu Gly His Val Ala
            185                 190                 195 gtc aag ttc ggc aag gcc ttc ggg atg aag gtc acc gtc atc agc acg    798
Val Lys Phe Gly Lys Ala Phe Gly Met Lys Val Thr Val Ile Ser Thr
        200                 205                 210 tcc gcc agc aag cgc cag gag gcc atc gag aac ctc ggc gcg gac gag    846
Ser Ala Ser Lys Arg Gln Glu Ala Ile Glu Asn Leu Gly Ala Asp Glu
    215                 220                 225 ttc ctc atc agc cgg gac gag gac cag atg aag gcg gcg acg ggg acc    894
Phe Leu Ile Ser Arg Asp Glu Asp Gln Met Lys Ala Ala Thr Gly Thr
230                 235                 240                 245 atg gac ggc atc atc gac acg gtg tcg gcg tgg cac ccg atc acg ccg    942
Met Asp Gly Ile Ile Asp Thr Val Ser Ala Trp His Pro Ile Thr Pro
                250                 255                 260 ctg ctg gcg ctg ctg aag ccg ctg ggg cag atg gtg gtc gtg ggc gcg    990
Leu Leu Ala Leu Leu Lys Pro Leu Gly Gln Met Val Val Val Gly Ala
            265                 270                 275 ccg agc aag ccg ctc gag ctg ccg gcc tac gcc atc gtg ccg ggc ggg    1038
Pro Ser Lys Pro Leu Glu Leu Pro Ala Tyr Ala Ile Val Pro Gly Gly
        280                 285                 290 aag ggc gtg gct ggg aac aat gtc ggc agc gtc agg gac tgc cag gcc    1086
Lys Gly Val Ala Gly Asn Asn Val Gly Ser Val Arg Asp Cys Gln Ala
    295                 300                 305 atg ctc gag ttc gcg ggg aag cac ggc atc ggg gcc gag gtc gag gtc    1134
Met Leu Glu Phe Ala Gly Lys His Gly Ile Gly Ala Glu Val Glu Val
310                 315                 320                 325 atc aag atg gac tac gtc aac acg gcc atg gag cgg ctc gag aag aac    1182
Ile Lys Met Asp Tyr Val Asn Thr Ala Met Glu Arg Leu Glu Lys Asn
                330                 335                 340 gac gtc cgc tac cgc ttc gtc atc gac gtc gcc ggc agc ctc ggc tct    1230
Asp Val Arg Tyr Arg Phe Val Ile Asp Val Ala Gly Ser Leu Gly Ser
            345                 350                 355 gcc gcc taggcatggc tgcaaaggtt tcaatcagag cccagccgca ataatttgtt    1286
Ala Ala agctaccgaa tgaatgatgg tctacgcttg ttgatgagtt ggtgctttgt cgtggttttg    1346
tggatgtaat aattcgatgt acaaataaaa aaggggaga caaggtgctt gttcccttgg     1406
tttggtgaca acttgttcgt ttacaccgat ctatctctaa attagtatga attaaaatt      1465
```

<210> SEQ ID NO 30
<211> LENGTH: 1316
<212> TYPE: DNA

```
<213> ORGANISM: Zea mays
<220> FEATURE:
<221> NAME/KEY: CDS
<222> LOCATION: (58)...(1131)

<400> SEQUENCE: 30
ccacgcgtcc gggttgaggt tgaggaagag cagaggaatc cattccagga gtgttta atg    60
                                                                 Met
                                                                  1
```

| | | | | | | | | | | | | | | | | |
|---|---|---|---|---|---|---|---|---|---|---|---|---|---|---|---|---|
| gcg | gga | ggc | aag | gaa | gcg | cac | ggg | tgg | gca | gcc | agg | gat | gtc | tct | ggt | 108 |
| Ala | Gly | Gly | Lys | Glu | Ala | His | Gly | Trp | Ala | Ala | Arg | Asp | Val | Ser | Gly | |
| | | | 5 | | | | 10 | | | | | 15 | | | | |

| cac | ctc | tcc | cct | tac | cac | ttc | tca | cgg | agg | gtt | cag | aga | gac | gac | gac | 156 |
|---|---|---|---|---|---|---|---|---|---|---|---|---|---|---|---|---|
| His | Leu | Ser | Pro | Tyr | His | Phe | Ser | Arg | Arg | Val | Gln | Arg | Asp | Asp | Asp | |
| | | 20 | | | | | 25 | | | | | 30 | | | | |

| gtc | acc | atc | aag | gtg | ctc | ttc | tgc | ggg | ctt | tgc | cac | act | gac | ctc | cac | 204 |
|---|---|---|---|---|---|---|---|---|---|---|---|---|---|---|---|---|
| Val | Thr | Ile | Lys | Val | Leu | Phe | Cys | Gly | Leu | Cys | His | Thr | Asp | Leu | His | |
| | 35 | | | | | 40 | | | | | 45 | | | | | |

| gtc | atc | aag | aac | gag | ttt | ggc | aac | gcc | aag | tac | ccc | gtc | gtt | ccc | ggg | 252 |
|---|---|---|---|---|---|---|---|---|---|---|---|---|---|---|---|---|
| Val | Ile | Lys | Asn | Glu | Phe | Gly | Asn | Ala | Lys | Tyr | Pro | Val | Val | Pro | Gly | |
| 50 | | | | | 55 | | | | | 60 | | | | | 65 | |

| cac | gag | att | gtc | ggc | gtc | gtc | acc | gac | gtc | ggc | tcc | ggc | gtc | aca | agc | 300 |
|---|---|---|---|---|---|---|---|---|---|---|---|---|---|---|---|---|
| His | Glu | Ile | Val | Gly | Val | Val | Thr | Asp | Val | Gly | Ser | Gly | Val | Thr | Ser | |
| | | | 70 | | | | | 75 | | | | | 80 | | | |

| ttc | aag | ccc | ggc | gac | acg | gtg | ggc | gtg | ggc | tac | ttc | gtc | gac | tcc | tgc | 348 |
|---|---|---|---|---|---|---|---|---|---|---|---|---|---|---|---|---|
| Phe | Lys | Pro | Gly | Asp | Thr | Val | Gly | Val | Gly | Tyr | Phe | Val | Asp | Ser | Cys | |
| | | 85 | | | | | 90 | | | | | 95 | | | | |

| cgc | agc | tgc | gac | agc | tgc | agc | aag | ggg | tac | gag | agc | tac | tgc | ccg | cag | 396 |
|---|---|---|---|---|---|---|---|---|---|---|---|---|---|---|---|---|
| Arg | Ser | Cys | Asp | Ser | Cys | Ser | Lys | Gly | Tyr | Glu | Ser | Tyr | Cys | Pro | Gln | |
| | 100 | | | | | 105 | | | | | 110 | | | | | |

| ctc | gtg | gag | acg | tcc | aac | ggc | gtg | agc | ctg | gac | gac | gat | gac | ggc | ggc | 444 |
|---|---|---|---|---|---|---|---|---|---|---|---|---|---|---|---|---|
| Leu | Val | Glu | Thr | Ser | Asn | Gly | Val | Ser | Leu | Asp | Asp | Asp | Asp | Gly | Gly | |
| 115 | | | | | 120 | | | | | 125 | | | | | | |

| gcc | acc | acc | aag | ggc | ggc | ttc | tcc | gac | gcc | ctc | gtc | gtc | cac | cag | cgc | 492 |
|---|---|---|---|---|---|---|---|---|---|---|---|---|---|---|---|---|
| Ala | Thr | Thr | Lys | Gly | Gly | Phe | Ser | Asp | Ala | Leu | Val | Val | His | Gln | Arg | |
| 130 | | | | | 135 | | | | | 140 | | | | | 145 | |

| tac | gtg | gtg | cgg | gtc | ccg | gcc | agc | ctg | ccg | ccc | gcc | ggg | gcc | gcg | ccg | 540 |
|---|---|---|---|---|---|---|---|---|---|---|---|---|---|---|---|---|
| Tyr | Val | Val | Arg | Val | Pro | Ala | Ser | Leu | Pro | Pro | Ala | Gly | Ala | Ala | Pro | |
| | | | 150 | | | | | 155 | | | | | 160 | | | |

| ctg | ctg | tgc | gcc | ggc | gtc | acc | gtg | ttc | agc | ccc | atg | gtg | cag | tac | ggc | 588 |
|---|---|---|---|---|---|---|---|---|---|---|---|---|---|---|---|---|
| Leu | Leu | Cys | Ala | Gly | Val | Thr | Val | Phe | Ser | Pro | Met | Val | Gln | Tyr | Gly | |
| | | 165 | | | | | 170 | | | | | 175 | | | | |

| ctg | aac | gcg | ccg | ggg | aag | cac | ctg | ggc | gtc | gtc | ggc | ctc | ggc | ggc | ctc | 636 |
|---|---|---|---|---|---|---|---|---|---|---|---|---|---|---|---|---|
| Leu | Asn | Ala | Pro | Gly | Lys | His | Leu | Gly | Val | Val | Gly | Leu | Gly | Gly | Leu | |
| | 180 | | | | | 185 | | | | | 190 | | | | | |

| ggc | cac | ctg | gcc | gtc | cgc | ttc | ggc | aag | gcg | ttc | ggg | atg | aag | gtc | acc | 684 |
|---|---|---|---|---|---|---|---|---|---|---|---|---|---|---|---|---|
| Gly | His | Leu | Ala | Val | Arg | Phe | Gly | Lys | Ala | Phe | Gly | Met | Lys | Val | Thr | |
| 195 | | | | | 200 | | | | | 205 | | | | | | |

| gtc | atc | agc | acg | tcg | ctg | ggc | aag | cgg | gac | gag | gcc | ctc | ggc | cgc | ctc | 732 |
|---|---|---|---|---|---|---|---|---|---|---|---|---|---|---|---|---|
| Val | Ile | Ser | Thr | Ser | Leu | Gly | Lys | Arg | Asp | Glu | Ala | Leu | Gly | Arg | Leu | |
| 210 | | | | | 215 | | | | | 220 | | | | | 225 | |

| ggt | gcc | gac | gcg | ttc | ctg | gtc | agc | cgc | gac | ccc | gag | cag | atg | agg | gcg | 780 |
|---|---|---|---|---|---|---|---|---|---|---|---|---|---|---|---|---|
| Gly | Ala | Asp | Ala | Phe | Leu | Val | Ser | Arg | Asp | Pro | Glu | Gln | Met | Arg | Ala | |
| | | | | 230 | | | | | 235 | | | | | 240 | | |

| gcg | gcg | ggc | acc | ttg | gac | ggc | gtc | atc | gac | acg | gtg | tcg | gcc | gac | cac | 828 |
|---|---|---|---|---|---|---|---|---|---|---|---|---|---|---|---|---|
| Ala | Ala | Gly | Thr | Leu | Asp | Gly | Val | Ile | Asp | Thr | Val | Ser | Ala | Asp | His | |
| | | | 245 | | | | | 250 | | | | | 255 | | | |

| cct | gtc | gtg | ccg | ctg | ctg | gac | ctg | ctc | aag | ccg | atg | ggc | cag | atg | gtc | 876 |
|---|---|---|---|---|---|---|---|---|---|---|---|---|---|---|---|---|
| Pro | Val | Val | Pro | Leu | Leu | Asp | Leu | Leu | Lys | Pro | Met | Gly | Gln | Met | Val | |
| | | 260 | | | | | 265 | | | | | 270 | | | | |

```
gtc gtc ggc ctg ccc acc aag ccg ctc cag gtg cct gcc ttc agc ctc        924
Val Val Gly Leu Pro Thr Lys Pro Leu Gln Val Pro Ala Phe Ser Leu
    275                 280                 285 gtc gcc ggc ggg aag cgc gtg gcc ggg agt gcc ggc ggc gtc ggg            972
Val Ala Gly Gly Lys Arg Val Ala Gly Ser Ala Gly Gly Val Gly
290                 295                 300                 305 gag tgc cag gcc atg ctc gac ttt gcc ggc gag cac ggg atc acc gcg       1020
Glu Cys Gln Ala Met Leu Asp Phe Ala Gly Glu His Gly Ile Thr Ala
                310                 315                 320 gat gtg gag gtc gtc ggg atg gac tac gtc aat acc gcc atc cag cgc       1068
Asp Val Glu Val Val Gly Met Asp Tyr Val Asn Thr Ala Ile Gln Arg
            325                 330                 335 cta gag agg aac gat gtc agg tac cgc ttc gtt gtc gac gtc gcg ggc       1116
Leu Glu Arg Asn Asp Val Arg Tyr Arg Phe Val Val Asp Val Ala Gly
        340                 345                 350 agc aag att gga ggc taggcatcac cattcctagt gttctgtcga tcgacgtgtg       1171
Ser Lys Ile Gly Gly
    355 atttgcttct tcctcgagcg tgtcttattg ttctggttgg agcacgtacg cggccatcac     1231 acgcaggcgt ggataataaa caaggtagag tttcggggttg tgtcgttct ggatgtatgg     1291 tgccggtgga taataaacaa gcttg                                           1316

<210> SEQ ID NO 31
<211> LENGTH: 1160
<212> TYPE: DNA
<213> ORGANISM: Zea mays
<220> FEATURE:
<221> NAME/KEY: CDS
<222> LOCATION: (167)...(940)

<400> SEQUENCE: 31
acccacgcgt ccgcgccttg ccgccgcgcg ttatataagc cgccccggca ggcaaggtcg       60
gtcaatccag caatacccga gtacccgacg cgctagctag ttctattgcc gcgcacccca      120
gatctccagg agggactcgt tcgttcagct aactacactg cacgca atg gcc acc         175
                                                   Met Ala Thr
                                                     1 acg gcg acc gag gcg gcg ccg gcg cag gag cag cag gcc aac ggc aac        223
Thr Ala Thr Glu Ala Ala Pro Ala Gln Glu Gln Gln Ala Asn Gly Asn
    5                  10                  15 ggc gag cag aag acg cgg cac tcc gag gtc ggc cac aag agc ctg ctc        271
Gly Glu Gln Lys Thr Arg His Ser Glu Val Gly His Lys Ser Leu Leu
20                  25                  30                  35 aag agc gac gac ctc tac cag tac atc ctg gac acg agc gtg tac ccg        319
Lys Ser Asp Asp Leu Tyr Gln Tyr Ile Leu Asp Thr Ser Val Tyr Pro
                40                  45                  50 cgg gag ccg gag agc atg aag gag ctc cgc gag atc acc gcc aag cac        367
Arg Glu Pro Glu Ser Met Lys Glu Leu Arg Glu Ile Thr Ala Lys His
            55                  60                  65 cca tgg aac ctg atg acg acc tcc gcc gac gag ggg cag ttc ctg aac        415
Pro Trp Asn Leu Met Thr Thr Ser Ala Asp Glu Gly Gln Phe Leu Asn
        70                  75                  80 atg ctc atc aag ctc atc ggc gcc aag aag acc atg gag atc ggc gtg        463
Met Leu Ile Lys Leu Ile Gly Ala Lys Lys Thr Met Glu Ile Gly Val
    85                  90                  95 tac acc ggc tac tcc ctc ctc gcc acg gcg ctc gcc ctc ccg gag gac        511
Tyr Thr Gly Tyr Ser Leu Leu Ala Thr Ala Leu Ala Leu Pro Glu Asp
100                 105                 110                 115 ggc acg atc ttg gcc atg gac atc aac cgc gag aac tac gag ctg ggc        559
Gly Thr Ile Leu Ala Met Asp Ile Asn Arg Glu Asn Tyr Glu Leu Gly
```

-continued

```
ctg ccc tgc atc gag aag gcc ggc gtc gcc cac aag atc gac ttc cgc     607
Leu Pro Cys Ile Glu Lys Ala Gly Val Ala His Lys Ile Asp Phe Arg
            135                 140                 145 gag ggc ccc gcg ctc ccc gtc ctc gac gac ctc atc gcg gag gag aag     655
Glu Gly Pro Ala Leu Pro Val Leu Asp Asp Leu Ile Ala Glu Glu Lys
        150                 155                 160 aac cac ggg tcg ttc gac ttc gtc ttc gtg gac gcc gac aag gac aac     703
Asn His Gly Ser Phe Asp Phe Val Phe Val Asp Ala Asp Lys Asp Asn
    165                 170                 175 tac ctc aac tac cac gag cgg ctg ctg aag ctg gtg aag ctg ggc ggc     751
Tyr Leu Asn Tyr His Glu Arg Leu Leu Lys Leu Val Lys Leu Gly Gly
180                 185                 190                 195 ctc atc ggc tac gac aac acg ctg tgg aac ggc tcc gtc gtg ctc ccc     799
Leu Ile Gly Tyr Asp Asn Thr Leu Trp Asn Gly Ser Val Val Leu Pro
                200                 205                 210 gac gac gcg ccc atg cgc aag tac atc cgc ttc tac cgc gac ttc gtg     847
Asp Asp Ala Pro Met Arg Lys Tyr Ile Arg Phe Tyr Arg Asp Phe Val
            215                 220                 225 ctc gtc ctc aac aag gcg ctc gcc gcc gac gac cgc gtc gag atc tgc     895
Leu Val Leu Asn Lys Ala Leu Ala Ala Asp Asp Arg Val Glu Ile Cys
        230                 235                 240 cag ctc ccc gtc ggc gac ggc gtc acc ctc tgc cgc cgc gtc aag         940
Gln Leu Pro Val Gly Asp Gly Val Thr Leu Cys Arg Arg Val Lys
    245                 250                 255 tgaaaacatg ccctggcctg ccccaccacc gccaccgacg gcgccgccgg ccgcatcctc   1000
attccaatca taatagacga cccgcagcat taattatcca ccggcttttt ttttggctct   1060
ttgttgcccc ctgtaatctt tctcctcctc ttcttcttgg gaattgtcgc cgccgtttcg   1120
atacgtaaat cacgagatcg gtaatacagt aatgctcctc                         1160

<210> SEQ ID NO 32
<211> LENGTH: 944
<212> TYPE: DNA
<213> ORGANISM: Zea mays
<220> FEATURE:
<221> NAME/KEY: CDS
<222> LOCATION: (60)...(803)

<400> SEQUENCE: 32
ccacgcgtcc gcttcccaca agaacatcac acggcgatag caaaaccttc cgtcggagg      59 atg gct tcc gcc ggc gct gga gaa ggg aag gag acg gct gcc ggg agc     107
Met Ala Ser Ala Gly Ala Gly Glu Gly Lys Glu Thr Ala Ala Gly Ser
1               5                   10                  15 agc ctc cac agc aag act ctc ctc aag agc caa cca ctg tac cag tac     155
Ser Leu His Ser Lys Thr Leu Leu Lys Ser Gln Pro Leu Tyr Gln Tyr
            20                  25                  30 ata ctg gaa tcc acc gtc ttc cca cgc gag ccg gac tgc ctg cgg gag     203
Ile Leu Glu Ser Thr Val Phe Pro Arg Glu Pro Asp Cys Leu Arg Glu
        35                  40                  45 ctc cgc gtc gcc acc gcc acc cac ccc atg gcg ggc atg gct gcg tcg     251
Leu Arg Val Ala Thr Ala Thr His Pro Met Ala Gly Met Ala Ala Ser
    50                  55                  60 ccg gac gag gtg cag ctg ctg cag ctc ctg atc gag att ctt ggc gcc     299
Pro Asp Glu Val Gln Leu Leu Gln Leu Leu Ile Glu Ile Leu Gly Ala
65                  70                  75                  80 aag aac gcc atc gag gtt ggc gtc ttc acc ggg tac tcg ctg ctc gcc     347
Lys Asn Ala Ile Glu Val Gly Val Phe Thr Gly Tyr Ser Leu Leu Ala
                85                  90                  95
```

```
acc gcc ctc gcc ctc ccc gac gac ggc aag att gtg gcc atc gac gtt      395
Thr Ala Leu Ala Leu Pro Asp Asp Gly Lys Ile Val Ala Ile Asp Val
        100                 105                 110 acc cgc gag agc tac gac cag ata ggg tcg ccg gtg atc gag aag gcc      443
Thr Arg Glu Ser Tyr Asp Gln Ile Gly Ser Pro Val Ile Glu Lys Ala
    115                 120                 125 ggc gtg gcg cac aag atc gac ttc cgc gtc ggg ctc gcg ctg ccc gtg      491
Gly Val Ala His Lys Ile Asp Phe Arg Val Gly Leu Ala Leu Pro Val
130                 135                 140 ctg gac cag atg gtg gcc gag gag ggg aac aag ggc aag ttc gac ttc      539
Leu Asp Gln Met Val Ala Glu Glu Gly Asn Lys Gly Lys Phe Asp Phe
145                 150                 155                 160 gcg ttc gtg gac gcg gac aag gtg aac ttc ctc aac tac cac gag cgg      587
Ala Phe Val Asp Ala Asp Lys Val Asn Phe Leu Asn Tyr His Glu Arg
                165                 170                 175 ctg ctg cag ctg ctc agg gtc ggg ggc ctc atc gcc tac gac aac acg      635
Leu Leu Gln Leu Leu Arg Val Gly Gly Leu Ile Ala Tyr Asp Asn Thr
            180                 185                 190 ctg tgg ggc ggc tcc gtg gcc gcg tcc ccc gac gag ccg ctc tcc gag      683
Leu Trp Gly Gly Ser Val Ala Ala Ser Pro Asp Glu Pro Leu Ser Glu
        195                 200                 205 cgg gac cgc gcg ctc gct gcg gcc acc agg gag ttc aac gcg gcc gtg      731
Arg Asp Arg Ala Leu Ala Ala Thr Arg Glu Phe Asn Ala Ala Val
    210                 215                 220 gcc gcc gat ccc cgc gtt cac gtc tgc cag gtc gcc atc gcc gac ggg      779
Ala Ala Asp Pro Arg Val His Val Cys Gln Val Ala Ile Ala Asp Gly
225                 230                 235                 240 ctc acg ctg tgc cgc cgc gtc gcc tgatccgtat ccggttatcc gcctcgaaat     833
Leu Thr Leu Cys Arg Arg Val Ala
                245 acagcagagc tgtgggctgt cgctgacact gctgtgagct ctgtgcttga aatggccatg    893 gtctgtaata cgaactggg cttgagcgaa aataaatcca ccagcgcgct a              944

<210> SEQ ID NO 33
<211> LENGTH: 1003
<212> TYPE: DNA
<213> ORGANISM: Zea mays
<220> FEATURE:
<221> NAME/KEY: CDS
<222> LOCATION: (55)...(798)

<400> SEQUENCE: 33
acagctagca ccaccacctt gcaccgcacc cgcaccgaga cgaacagatc gacc atg      57
                                                             Met
                                                              1 gct gcc ggc ggc gac gac acc acc atc gcg cag gtc cac agc ggc atc      105
Ala Ala Gly Gly Asp Asp Thr Thr Ile Ala Gln Val His Ser Gly Ile
      5                  10                  15 gac agc agc aac aag acg ctg ctc aag agc gag gcc ctc tac aag tac      153
Asp Ser Ser Asn Lys Thr Leu Leu Lys Ser Glu Ala Leu Tyr Lys Tyr
            20                  25                  30 gtg ctg gac acg tcg gtg ctg ccg cac gag ccg gag agc atg cgt gag      201
Val Leu Asp Thr Ser Val Leu Pro His Glu Pro Glu Ser Met Arg Glu
        35                  40                  45 ctg cgg ctg gtg acc gac aag cac gag tgg ggg ttc atg cag tcg tcc      249
Leu Arg Leu Val Thr Asp Lys His Glu Trp Gly Phe Met Gln Ser Ser
 50                  55                  60                  65 ccg gac gag gcg tcg ctg ctg cgg atg ctg atc aag ctg agc ggc gcg      297
Pro Asp Glu Ala Ser Leu Leu Arg Met Leu Ile Lys Leu Ser Gly Ala
                70                  75                  80
```

```
cgg cgg acg ctg gag gtg ggc gtg ttc acg ggc tac tcg ctg ctg gcg      345
Arg Arg Thr Leu Glu Val Gly Val Phe Thr Gly Tyr Ser Leu Leu Ala
            85                  90                  95 acg gct ctg gcg ctg ccc gcc gac ggc aag gtc atc gca ttc gac gtg      393
Thr Ala Leu Ala Leu Pro Ala Asp Gly Lys Val Ile Ala Phe Asp Val
                100                 105                 110 agc cgc gag tac tac gac atc ggc cgc ccc ttc atc gag cgc gcc ggg      441
Ser Arg Glu Tyr Tyr Asp Ile Gly Arg Pro Phe Ile Glu Arg Ala Gly
        115                 120                 125 gtg gcg ggc aag gtg gac ttc cgg gag ggc ccg gcg ctg gag cag ctg      489
Val Ala Gly Lys Val Asp Phe Arg Glu Gly Pro Ala Leu Glu Gln Leu
130                 135                 140                 145 gac gag ctc ctc gcc gac ccg gcc aac cac ggc gcc ttc gac ttc gcc      537
Asp Glu Leu Leu Ala Asp Pro Ala Asn His Gly Ala Phe Asp Phe Ala
                150                 155                 160 ttc gtc gac gcc gac aag cct aac tac gtc cgg tac cac gag cag ctg      585
Phe Val Asp Ala Asp Lys Pro Asn Tyr Val Arg Tyr His Glu Gln Leu
            165                 170                 175 ctc cgc ctg gtg cgc gtc ggg ggt acc gtc gtg tac gac aac acg ctg      633
Leu Arg Leu Val Arg Val Gly Gly Thr Val Val Tyr Asp Asn Thr Leu
        180                 185                 190 tgg gcc ggt act gtg gcg ctt ccc ccc gac gcg ccg ctc agc gac ctc      681
Trp Ala Gly Thr Val Ala Leu Pro Pro Asp Ala Pro Leu Ser Asp Leu
195                 200                 205 gac cgc agg ttc tcc gcc gcc atc agg gaa ctc aac gtc cgg ctt tct      729
Asp Arg Arg Phe Ser Ala Ala Ile Arg Glu Leu Asn Val Arg Leu Ser
210                 215                 220                 225 cag gat ccc cgc gtc gag gtc tgc cag ctc gcc atc gcc gac ggc gtc      777
Gln Asp Pro Arg Val Glu Val Cys Gln Leu Ala Ile Ala Asp Gly Val
                230                 235                 240 acc atc tgc cgc cgc gtc gtc tgatgtgatg atgatccgac gaccaagatc        828
Thr Ile Cys Arg Arg Val Val
            245 atatatcatt cgctcgtcgt ctctgtcatc tttcaactgc ctgcccgccg ctgtccgctg    888 ccgtcgtcaa ttaataatgc atggttcttg ttctttttt ttttgtactt gcactgtgtg    948 tgttgagttg aacatccggc gatgtactgc aacaactgga atgcaatgca acaaa        1003

<210> SEQ ID NO 34
<211> LENGTH: 1559
<212> TYPE: DNA
<213> ORGANISM: Zea mays
<220> FEATURE:
<221> NAME/KEY: CDS
<222> LOCATION: (231)...(1343)
<220> FEATURE:
<221> NAME/KEY: misc_feature
<222> LOCATION: (1)...(1559)
<223> OTHER INFORMATION: n = A,T,C or G

<400> SEQUENCE: 34
gtcgacccac gcgtccggga agagagaatc ctaccaaacc tagctaccaa ctcgatcgtc     60
gtcatcacgc tcgaccgcac aactgcacca aggggggagg agacctaaaa actactacat    120
cttttagcta cacatctagc taaagatcga gaggggtaaa taaggacgag cgggcgcgag    180
ctagaagagc agctgcaggt actaccatca tcgtcgtcgt cgtcgccagg atg acc      236
                                                          Met Thr
                                                            1 gtc gtc gac gcc gtc gtc tcc tcc acc gat gcc ggc gcc cct gct gcc      284
Val Val Asp Ala Val Val Ser Ser Thr Asp Ala Gly Ala Pro Ala Ala
        5                   10                  15
```

| | | |
|---|---|---|
| gcc gcc acc gcg gta ccg gcg ggg aac ggg cag acc gtg tgc gtg acc<br>Ala Ala Thr Ala Val Pro Ala Gly Asn Gly Gln Thr Val Cys Val Thr<br>20                        25                        30 | 332 | |
| ggc gcg gcc ggg tac atc gcc tcg tgg ttg gtg aag ctg ctg ctc gag<br>Gly Ala Ala Gly Tyr Ile Ala Ser Trp Leu Val Lys Leu Leu Leu Glu<br>35                        40                        45                        50 | 380 | |
| aag gga tac act gtg aag ggc acc gtc agg aac cca gat gac ccg aag<br>Lys Gly Tyr Thr Val Lys Gly Thr Val Arg Asn Pro Asp Asp Pro Lys<br>                    55                        60                        65 | 428 | |
| aac gcg cac ctc aag gcg ctg gac ggc gcc gcc gag cgg ctg atc ctc<br>Asn Ala His Leu Lys Ala Leu Asp Gly Ala Ala Glu Arg Leu Ile Leu<br>                    70                        75                        80 | 476 | |
| tgc aag gcc gat ctg ctg gac tac gac gcc atc tgc cgc gcc gtg cag<br>Cys Lys Ala Asp Leu Leu Asp Tyr Asp Ala Ile Cys Arg Ala Val Gln<br>85                        90                        95 | 524 | |
| ggc tgc cag ggc gtc ttc cac acc gcc tcc ccc gtc acc gac gac ccg<br>Gly Cys Gln Gly Val Phe His Thr Ala Ser Pro Val Thr Asp Asp Pro<br>100                       105                      110 | 572 | |
| gag caa atg gtg gag ccg gcg gtg cgc ggc acc gag tac gtg atc aac<br>Glu Gln Met Val Glu Pro Ala Val Arg Gly Thr Glu Tyr Val Ile Asn<br>115                       120                      125                  130 | 620 | |
| gcg gcg gcg gat gcc ggc acg gtg cgg cgg gtg gtg ttc acg tcg tcc<br>Ala Ala Ala Asp Ala Gly Thr Val Arg Arg Val Val Phe Thr Ser Ser<br>                        135                      140                      145 | 668 | |
| atc ggc gcc gtg acc atg gac ccc aag cgc ggg ccc gac gtc gtg gtc<br>Ile Gly Ala Val Thr Met Asp Pro Lys Arg Gly Pro Asp Val Val Val<br>                    150                      155                      160 | 716 | |
| gac gag tcg tgc tgg agc gac ctc gag ttc tgc gag aaa acc agg aac<br>Asp Glu Ser Cys Trp Ser Asp Leu Glu Phe Cys Glu Lys Thr Arg Asn<br>165                       170                      175 | 764 | |
| tgg tac tgc tac ggc aag gcg gtg gcg gaa cag gcg gcg tgg gag acg<br>Trp Tyr Cys Tyr Gly Lys Ala Val Ala Glu Gln Ala Ala Trp Glu Thr<br>180                       185                      190 | 812 | |
| gcc cgg cgg cgg ggc gtg gac ctg gtg gtg gtg aac ccc gtg ctg gtg<br>Ala Arg Arg Arg Gly Val Asp Leu Val Val Val Asn Pro Val Leu Val<br>195                       200                      205                  210 | 860 | |
| gtg ggc ccc ctg ctg cag gcg acg gtg aac gcc agc atc gcg cac atc<br>Val Gly Pro Leu Leu Gln Ala Thr Val Asn Ala Ser Ile Ala His Ile<br>                       215                      220                  225 | 908 | |
| ctc aag tac ctg gac ggc tcg gcc cgc acc ttc gcc aac gcc gtg cag<br>Leu Lys Tyr Leu Asp Gly Ser Ala Arg Thr Phe Ala Asn Ala Val Gln<br>                    230                      235                  240 | 956 | |
| gcg tac gtg gac gtg cgc gac gtg gcc gac gcg cac ctc cgc gtc ttc<br>Ala Tyr Val Asp Val Arg Asp Val Ala Asp Ala His Leu Arg Val Phe<br>245                       250                      255 | 1004 | |
| gag agc ccc cgc gcg tcc ggc cgc can ctc tgc gcc gag cgc gtc ctc<br>Glu Ser Pro Arg Ala Ser Gly Arg Xaa Leu Cys Ala Glu Arg Val Leu<br>260                       265                      270 | 1052 | |
| cac cgc gag gac gtc gtc cgc atc ctc gcc aag ctc ttc ccc gag tac<br>His Arg Glu Asp Val Val Arg Ile Leu Ala Lys Leu Phe Pro Glu Tyr<br>275                       280                      285                  290 | 1100 | |
| ccc gtc cca gcc agg tgc tcc gac gag gtg aat ccg cgg aag cag ccg<br>Pro Val Pro Ala Arg Cys Ser Asp Glu Val Asn Pro Arg Lys Gln Pro<br>                       295                      300                  305 | 1148 | |
| tac aag ttc tcc aac cag aag ctc cgg gac ctg ggg ctg cag ttc cgg<br>Tyr Lys Phe Ser Asn Gln Lys Leu Arg Asp Leu Gly Leu Gln Phe Arg<br>                    310                      315                  320 | 1196 | |
| ccg gtc agc cag tcg ctt tac gac acg gtg aag aac ctc cag gag aag<br>Pro Val Ser Gln Ser Leu Tyr Asp Thr Val Lys Asn Leu Gln Glu Lys<br>325                       330                      335 | 1244 | |

-continued

```
gga cac ctg ccg gtg ctc gga gag cgg acg acg acg gag gcc gcc gac      1292
Gly His Leu Pro Val Leu Gly Glu Arg Thr Thr Thr Glu Ala Ala Asp
            340                 345                 350 aag gat gcc ccc acg gcc gag atg cag cag gga ggg atc gcc atc cgt      1340
Lys Asp Ala Pro Thr Ala Glu Met Gln Gln Gly Gly Ile Ala Ile Arg
355                 360                 365                 370 gcc tgagagggcg atgccacaca tgaacacaaa gcaatgttca tactgctgcc           1393
Ala ctgcacctgc tgtgtaaaca ggcctgtgtt tgttctggct gatagtgatg taccctaaga   1453
cttgtaacgt catgttcgtt cttgtgaact atagcgagtg aataaaattg gttaatgttg   1513
gatgttcaaa aaaaaaaaaa aaaaaaaaaa aaaaaagggc ggccgc                   1559
```

<210> SEQ ID NO 35
<211> LENGTH: 755
<212> TYPE: DNA
<213> ORGANISM: Zea mays
<220> FEATURE:
<221> NAME/KEY: CDS
<222> LOCATION: (3)...(533)

<400> SEQUENCE: 35

```
cc acg cgt ccg gtc gtg ggc ctc gac cgc aac gtg agc gag tcg gac        47
   Thr Arg Pro Val Val Gly Leu Asp Arg Asn Val Ser Glu Ser Asp
     1               5                  10                  15 ctg gac agg ctc ccc ttc ctc agg tgc gtc atc aag gag acg ctc cgg       95
Leu Asp Arg Leu Pro Phe Leu Arg Cys Val Ile Lys Glu Thr Leu Arg
             20                  25                  30 ctg cac ccg ccc atc ccg ctg ctc ctc cac gag acc gcc gac gac tgc      143
Leu His Pro Pro Ile Pro Leu Leu Leu His Glu Thr Ala Asp Asp Cys
         35                  40                  45 gtc gtg gcc ggg tac tcc gtg ccc agg ggc tcc cgc gtc atg gtc aac      191
Val Val Ala Gly Tyr Ser Val Pro Arg Gly Ser Arg Val Met Val Asn
     50                  55                  60 gtc tgg gcc atc ggc cgc cac cgc gcc tcg tgg aag gac gcc gac gcg      239
Val Trp Ala Ile Gly Arg His Arg Ala Ser Trp Lys Asp Ala Asp Ala
 65                  70                  75 ttc cgc ccg tcg cgg ttc gcg gcg ccc gag ggg gag gcc gcg ggg ctc      287
Phe Arg Pro Ser Arg Phe Ala Ala Pro Glu Gly Glu Ala Ala Gly Leu
 80                  85                  90                  95 gac ttc aag ggc ggg tgc ttc gag ttc ctg ccg ttc ggg tcg ggc cgc      335
Asp Phe Lys Gly Gly Cys Phe Glu Phe Leu Pro Phe Gly Ser Gly Arg
             100                 105                 110 cgg tcc tgc ccc ggg atg gcg ctc ggc ctg tac gcg ctg gag ctc gcc      383
Arg Ser Cys Pro Gly Met Ala Leu Gly Leu Tyr Ala Leu Glu Leu Ala
         115                 120                 125 gtc gcc cag ctc gcg cac gcc ttc aac tgg tcg ctg ccc gac gga atg      431
Val Ala Gln Leu Ala His Ala Phe Asn Trp Ser Leu Pro Asp Gly Met
     130                 135                 140 aag ccc tcg gag atg gac atg ggc gac atc ttc ggc ctt acc gcg ccg      479
Lys Pro Ser Glu Met Asp Met Gly Asp Ile Phe Gly Leu Thr Ala Pro
145                 150                 155 cgc gcc acg cgg ctc tac gcc gtg cct acg ccc cgg ctc aac tgc ccc      527
Arg Ala Thr Arg Leu Tyr Ala Val Pro Thr Pro Arg Leu Asn Cys Pro
160                 165                 170                 175 ttg tac tgacgccctg cacgtggcgc gcggggactg ccattacgca tgcatgcgtt       583
Leu Tyr tggactttgg tgttcatccc tggggtgggg ccgccgtggg ggaagttagg agtttggtgg    643 cttttctagct ctgtcttctt gtattctgtt tattataaat tttcccaacc cttccatgcc   703
```

```
tgatcgatgt gcggtaataa ttgttagaaa atgtgacatt ttgtatgtaa tc          755

<210> SEQ ID NO 36
<211> LENGTH: 972
<212> TYPE: DNA
<213> ORGANISM: Zea mays
<220> FEATURE:
<221> NAME/KEY: CDS
<222> LOCATION: (2)...(706)

<400> SEQUENCE: 36 g gca cga gat ttc ccg gac ggt ccg ccg ccc agc ggc acg gcg atg tcg     49
  Ala Arg Asp Phe Pro Asp Gly Pro Pro Pro Ser Gly Thr Ala Met Ser
  1               5                  10                  15 gtg ggg acc aag ctc aat aag ctc agc tac aac tcg gtg gtg gag atc       97
Val Gly Thr Lys Leu Asn Lys Leu Ser Tyr Asn Ser Val Val Glu Ile
            20                  25                  30 gtg ctg cag aac ccg gcg gcc gtc ccg acg gag aac cac ccg atc cac      145
Val Leu Gln Asn Pro Ala Ala Val Pro Thr Glu Asn His Pro Ile His
        35                  40                  45 ctc cac ggc ttc aac ttc ttc gtg ctg gcg cag ggg atg ggt acc ttc      193
Leu His Gly Phe Asn Phe Phe Val Leu Ala Gln Gly Met Gly Thr Phe
    50                  55                  60 gcc ccg gga agc gtg gcc tac aac ctg gtg gac ccg gtg gcc cgc aac      241
Ala Pro Gly Ser Val Ala Tyr Asn Leu Val Asp Pro Val Ala Arg Asn
65                  70                  75                  80 acc atc gcc gtg cct ggc ggt ggc tgg gct gtc ata cgc ttc gtc gcc      289
Thr Ile Ala Val Pro Gly Gly Gly Trp Ala Val Ile Arg Phe Val Ala
                85                  90                  95 aac aat cca ggc atg tgg ttc ttt cac tgc cac ctg gac ccg cac gtg      337
Asn Asn Pro Gly Met Trp Phe Phe His Cys His Leu Asp Pro His Val
            100                 105                 110 cct atg ggc ctg ggc atg gtg ttc cag gtg gac agc ggg acg acg ccc      385
Pro Met Gly Leu Gly Met Val Phe Gln Val Asp Ser Gly Thr Thr Pro
        115                 120                 125 ggc tcc acg ctc cct acg ccg ccg ggg gat tgg gtg gga gta tgc gac      433
Gly Ser Thr Leu Pro Thr Pro Pro Gly Asp Trp Val Gly Val Cys Asp
    130                 135                 140 gcg cag cac tac gcg gcc gcg gcg gta gca gca gcg ccg gtg cca          481
Ala Gln His Tyr Ala Ala Ala Ala Val Ala Ala Ala Pro Val Pro
145                 150                 155                 160 gtt ccg gcc cca gcc cca gtc cca gca cca atc cta gcg cca gca cca      529
Val Pro Ala Pro Ala Pro Val Pro Ala Pro Ile Leu Ala Pro Ala Pro
                165                 170                 175 gca gaa tcg ccg ttg cca cct ccg cgc gcg gtg gac cac aag ccg tcg      577
Ala Glu Ser Pro Leu Pro Pro Arg Ala Val Asp His Lys Pro Ser
            180                 185                 190 ccc aac ctt cct cag cgc agg gag cac acg ggt acc tct aat tcc gct      625
Pro Asn Leu Pro Gln Arg Arg Glu His Thr Gly Thr Ser Asn Ser Ala
        195                 200                 205 gct gga cgg aga gct aag ggg cac ctc gct tgt ttc ttg tgt tct gtc      673
Ala Gly Arg Arg Ala Lys Gly His Leu Ala Cys Phe Leu Cys Ser Val
    210                 215                 220 ctc ctt ttc ttt ctt ctt cgt caa cac aag gcc tagctcatgg gaagctttgg   726
Leu Leu Phe Phe Leu Leu Arg Gln His Lys Ala
225                 230                 235 cgtgataccc gcgcagaatc tgcagttttg ttcgttcgtg taagtaatat gaaattgttt    786
attctttaaa tgttttatac acgtgtatat ggacttatat tttgatgtaa ttgtgtgacc    846
ttttccttct ccacgtgggc agttgtgcat agcaaagttc atgtttaggg tttattggct    906
```

```
ctctgtattc atgatagaca ttgatacaaa gtaatatcat acactacggt ttgatttgaa     966
accccc                                                                972
```

```
<210> SEQ ID NO 37
<211> LENGTH: 25
<212> TYPE: DNA
<213> ORGANISM: Zea mays

<400> SEQUENCE: 37
atgggcgacg cggccatcgc cgccg                                           25

<210> SEQ ID NO 38
<211> LENGTH: 25
<212> TYPE: DNA
<213> ORGANISM: Zea mays

<400> SEQUENCE: 38
cgctgctgcc gtcttcttga cgaac                                           25

<210> SEQ ID NO 39
<211> LENGTH: 25
<212> TYPE: DNA
<213> ORGANISM: Zea mays

<400> SEQUENCE: 39
atgggttccg tagacgcggc gatcg                                           25

<210> SEQ ID NO 40
<211> LENGTH: 25
<212> TYPE: DNA
<213> ORGANISM: Zea mays

<400> SEQUENCE: 40
ctgaacaccg gcggcgagcc tggct                                           25

<210> SEQ ID NO 41
<211> LENGTH: 25
<212> TYPE: DNA
<213> ORGANISM: Zea mays

<400> SEQUENCE: 41
atgatcacgg tggcagcacc ggagg                                           25

<210> SEQ ID NO 42
<211> LENGTH: 25
<212> TYPE: DNA
<213> ORGANISM: Zea mays

<400> SEQUENCE: 42
ggcggtcgcg gctgccgcga gcttg                                           25

<210> SEQ ID NO 43
<211> LENGTH: 25
<212> TYPE: DNA
<213> ORGANISM: Zea mays

<400> SEQUENCE: 43
atggccaccg ccatagttcc cacgg                                           25

<210> SEQ ID NO 44
<211> LENGTH: 25
<212> TYPE: DNA
```

<213> ORGANISM: Zea mays

<400> SEQUENCE: 44
tgggtagacc tcgatgacac cacga 25

<210> SEQ ID NO 45
<211> LENGTH: 25
<212> TYPE: DNA
<213> ORGANISM: Zea mays

<400> SEQUENCE: 45
atggccctca tgcaggagag tagta 25

<210> SEQ ID NO 46
<211> LENGTH: 25
<212> TYPE: DNA
<213> ORGANISM: Zea mays

<400> SEQUENCE: 46
aggatagacc tcgatgatga ccgat 25

<210> SEQ ID NO 47
<211> LENGTH: 25
<212> TYPE: DNA
<213> ORGANISM: Zea mays

<400> SEQUENCE: 47
atggcactca tgcaagagag cagta 25

<210> SEQ ID NO 48
<211> LENGTH: 25
<212> TYPE: DNA
<213> ORGANISM: Zea mays

<400> SEQUENCE: 48
aggatagacc tcgatgatga ccgac 25

<210> SEQ ID NO 49
<211> LENGTH: 25
<212> TYPE: DNA
<213> ORGANISM: Zea mays

<400> SEQUENCE: 49
atggcactca tgcaggagag cagcc 25

<210> SEQ ID NO 50
<211> LENGTH: 25
<212> TYPE: DNA
<213> ORGANISM: Zea mays

<400> SEQUENCE: 50
tggatagacc tcgatgaccg acatg 25

<210> SEQ ID NO 51
<211> LENGTH: 25
<212> TYPE: DNA
<213> ORGANISM: Zea mays

<400> SEQUENCE: 51
atggtccttc tcttcgtgga gaagc 25

<210> SEQ ID NO 52
<211> LENGTH: 25

```
<212> TYPE: DNA
<213> ORGANISM: Zea mays

<400> SEQUENCE: 52
aagcgttctt ggcttgcaca cgatg                                    25

<210> SEQ ID NO 53
<211> LENGTH: 25
<212> TYPE: DNA
<213> ORGANISM: Zea mays

<400> SEQUENCE: 53
atggacctcg ccctcctaga gaagg                                    25

<210> SEQ ID NO 54
<211> LENGTH: 25
<212> TYPE: DNA
<213> ORGANISM: Zea mays

<400> SEQUENCE: 54
ggcctcgagg ggcttgcaga cgatg                                    25

<210> SEQ ID NO 55
<211> LENGTH: 25
<212> TYPE: DNA
<213> ORGANISM: Zea mays

<400> SEQUENCE: 55
atggcaccgg tggaggcgga gcagc                                    25

<210> SEQ ID NO 56
<211> LENGTH: 25
<212> TYPE: DNA
<213> ORGANISM: Zea mays

<400> SEQUENCE: 56
cagagctggg accggcgagc tccct                                    25

<210> SEQ ID NO 57
<211> LENGTH: 25
<212> TYPE: DNA
<213> ORGANISM: Zea mays

<400> SEQUENCE: 57
atggaagagc aaggcggcca ggcgg                                    25

<210> SEQ ID NO 58
<211> LENGTH: 25
<212> TYPE: DNA
<213> ORGANISM: Zea mays

<400> SEQUENCE: 58
ggcggcagag ccgaggctgc cggcg                                    25

<210> SEQ ID NO 59
<211> LENGTH: 25
<212> TYPE: DNA
<213> ORGANISM: Zea mays

<400> SEQUENCE: 59
atggcgggag gcaaggaagc gcacg                                    25

<210> SEQ ID NO 60
```

<211> LENGTH: 25
<212> TYPE: DNA
<213> ORGANISM: Zea mays

<400> SEQUENCE: 60
gcctccaatc ttgctgcccg cgacg 25

<210> SEQ ID NO 61
<211> LENGTH: 25
<212> TYPE: DNA
<213> ORGANISM: Zea mays

<400> SEQUENCE: 61
atggccacca cggcgaccga ggcgg 25

<210> SEQ ID NO 62
<211> LENGTH: 25
<212> TYPE: DNA
<213> ORGANISM: Zea mays

<400> SEQUENCE: 62
cttgacgcgg cggcagaggg tgacg 25

<210> SEQ ID NO 63
<211> LENGTH: 25
<212> TYPE: DNA
<213> ORGANISM: Zea mays

<400> SEQUENCE: 63
atggcttccg ccggcgctgg agaag 25

<210> SEQ ID NO 64
<211> LENGTH: 25
<212> TYPE: DNA
<213> ORGANISM: Zea mays

<400> SEQUENCE: 64
ggcgacgcgg cggcacagcg tgagc 25

<210> SEQ ID NO 65
<211> LENGTH: 25
<212> TYPE: DNA
<213> ORGANISM: Zea mays

<400> SEQUENCE: 65
atggctgccg gcggcgacga cacca 25

<210> SEQ ID NO 66
<211> LENGTH: 25
<212> TYPE: DNA
<213> ORGANISM: Zea mays

<400> SEQUENCE: 66
gacgacgcgg cggcagatgg tgacg 25

<210> SEQ ID NO 67
<211> LENGTH: 25
<212> TYPE: DNA
<213> ORGANISM: Zea mays

<400> SEQUENCE: 67
atgaccgtcg tcgacgccgt cgtct 25

```
<210> SEQ ID NO 68
<211> LENGTH: 25
<212> TYPE: DNA
<213> ORGANISM: Zea mays

<400> SEQUENCE: 68
ggcacggatg gcgatccctc cctgc                                  25

<210> SEQ ID NO 69
<211> LENGTH: 25
<212> TYPE: DNA
<213> ORGANISM: Zea mays

<400> SEQUENCE: 69
ccacgcgtcc ggtcgtgggc ctcga                                  25

<210> SEQ ID NO 70
<211> LENGTH: 25
<212> TYPE: DNA
<213> ORGANISM: Zea mays

<400> SEQUENCE: 70
tcaggcatgg aagggttggg aaaat                                  25

<210> SEQ ID NO 71
<211> LENGTH: 25
<212> TYPE: DNA
<213> ORGANISM: Zea mays

<400> SEQUENCE: 71
ggcacgagat ttcccggacg gtccg                                  25

<210> SEQ ID NO 72
<211> LENGTH: 25
<212> TYPE: DNA
<213> ORGANISM: Zea mays

<400> SEQUENCE: 72
ctaggccttg tgttgacgaa gaaga                                  25

<210> SEQ ID NO 73
<211> LENGTH: 526
<212> TYPE: PRT
<213> ORGANISM: Zea mays

<400> SEQUENCE: 73

Met Val Thr Val Ala Lys Ile Ala Met Glu Trp Leu Gln Asp Pro Leu
 1               5                  10                  15

Ser Trp Val Phe Leu Gly Thr Leu Ala Leu Val Val Leu Gln Leu Arg
            20                  25                  30

Arg Arg Gly Lys Ala Pro Leu Pro Pro Gly Pro Lys Pro Leu Pro Ile
        35                  40                  45

Val Gly Asn Met Ala Met Met Asp Gln Leu Thr His Arg Gly Leu Ala
    50                  55                  60

Ala Leu Ala Glu Arg Tyr Gly Gly Leu Leu His Leu Arg Leu Gly Arg
65                  70                  75                  80

Leu His Ala Phe Ala Val Ser Thr Pro Glu Tyr Ala Arg Glu Val Leu
                85                  90                  95

Gln Ala Gln Asp Gly Ala Phe Ser Asn Arg Pro Ala Thr Ile Ala Ile
            100                 105                 110

Ala Tyr Leu Thr Tyr Asp Arg Ala Asp Met Ala Phe Ala His Tyr Gly
```

-continued

```
              115                 120                 125
Pro Phe Trp Arg Gln Met Arg Lys Leu Cys Val Met Lys Leu Phe Ser
    130                 135                 140

Arg Arg Arg Ala Glu Thr Trp Val Ala Val Arg Asp Glu Cys Ala Ala
145                 150                 155                 160

Leu Val Arg Ala Val Ala Ser Gly Gly Gly Gly Gly Glu Ala Val
                165                 170                 175

Asn Leu Gly Glu Leu Ile Phe Asn Leu Thr Lys Asn Val Thr Phe Arg
            180                 185                 190

Ala Ala Phe Gly Thr Arg Asp Gly Glu Asp Gln Glu Glu Phe Ile Ala
        195                 200                 205

Ile Leu Gln Glu Phe Ser Lys Leu Phe Gly Ala Phe Asn Val Val Asp
    210                 215                 220

Phe Leu Pro Trp Leu Ser Trp Met Asp Leu Gln Gly Ile Asn Arg Arg
225                 230                 235                 240

Leu Arg Ala Ala Arg Ser Ala Leu Asp Arg Phe Ile Asp Lys Ile Ile
                245                 250                 255

Asp Glu His Val Arg Arg Gly Lys Asn Pro Asp Asp Ala Asp Ala Asp
            260                 265                 270

Met Val Asp Asp Met Leu Ala Phe Phe Ala Glu Ala Lys Pro Pro Lys
        275                 280                 285

Lys Gly Pro Ala Ala Ala Asp Gly Asp Asp Leu His Asn Thr Leu
    290                 295                 300

Arg Leu Thr Arg Asp Asn Ile Lys Ala Ile Ile Met Asp Val Met Phe
305                 310                 315                 320

Gly Gly Thr Glu Thr Val Ala Ser Ala Ile Glu Trp Ala Met Ala Glu
                325                 330                 335

Met Met His Ser Pro Asp Asp Leu Arg Arg Leu Gln Gln Glu Leu Ala
            340                 345                 350

Asp Val Gly Leu Asp Arg Asn Val Asn Glu Ser Asp Leu Asp Lys
        355                 360                 365

Leu Pro Phe Leu Lys Cys Val Ile Lys Glu Thr Leu Arg Leu His Pro
    370                 375                 380

Pro Ile Pro Leu Leu Leu His Glu Thr Ala Gly Asp Cys Val Val Gly
385                 390                 395                 400

Gly Tyr Ser Val Pro Arg Gly Ser Arg Val Met Val Asn Val Trp Ala
                405                 410                 415

Ile Gly Arg His Arg Ala Ser Trp Lys Asp Ala Asp Ala Phe Arg Pro
            420                 425                 430

Ser Arg Phe Thr Pro Glu Gly Glu Ala Ala Gly Leu Asp Phe Lys Gly
        435                 440                 445

Gly Cys Phe Glu Phe Leu Pro Phe Gly Ser Gly Arg Arg Ser Cys Pro
    450                 455                 460

Gly Thr Ala Leu Gly Leu Tyr Ala Leu Glu Leu Ala Val Ala Gln Leu
465                 470                 475                 480

Ala His Gly Phe Asn Trp Ser Leu Pro Asp Gly Met Lys Pro Ser Glu
                485                 490                 495

Leu Asp Met Gly Asp Val Phe Gly Leu Thr Ala Pro Arg Ala Thr Arg
            500                 505                 510

Leu Tyr Ala Val Pro Thr Pro Arg Leu Asn Cys Pro Leu Tyr
        515                 520                 525
```

<210> SEQ ID NO 74

-continued

```
<211> LENGTH: 263
<212> TYPE: PRT
<213> ORGANISM: Zea mays

<400> SEQUENCE: 74

Met Ala Thr Thr Ala Thr Glu Ala Ala Lys Ala Pro Ala Gln Glu
 1               5                  10                  15

Gln Gln Ala Asn Gly Asn Gly Asn Gly Glu Gln Lys Thr Arg His Ser
            20                  25                  30

Glu Val Gly His Lys Ser Leu Leu Lys Ser Asp Asp Leu Tyr Gln Tyr
        35                  40                  45

Ile Leu Asp Thr Ser Val Tyr Pro Arg Glu Pro Glu Ser Met Lys Glu
    50                  55                  60

Leu Arg Glu Ile Thr Ala Lys His Pro Trp Asn Leu Met Thr Thr Ser
65                  70                  75                  80

Ala Asp Glu Gly Gln Phe Leu Asn Met Leu Ile Lys Leu Ile Gly Ala
                85                  90                  95

Lys Lys Thr Met Glu Ile Gly Val Tyr Thr Gly Tyr Ser Leu Leu Ala
            100                 105                 110

Thr Ala Leu Ala Leu Pro Glu Asp Gly Thr Ile Leu Ala Met Asp Ile
        115                 120                 125

Asn Arg Glu Asn Tyr Glu Leu Gly Leu Pro Cys Ile Asn Lys Ala Gly
    130                 135                 140

Val Gly His Lys Ile Asp Phe Arg Glu Gly Pro Ala Leu Pro Val Leu
145                 150                 155                 160

Asp Asp Leu Val Ala Asp Lys Glu Gln His Gly Ser Phe Asp Phe Ala
                165                 170                 175

Phe Val Asp Ala Asp Lys Asp Asn Tyr Leu Ser Tyr His Glu Arg Leu
            180                 185                 190

Leu Lys Leu Val Arg Pro Gly Gly Leu Ile Gly Tyr Asp Asn Thr Leu
        195                 200                 205

Trp Asn Gly Ser Val Val Leu Pro Asp Asp Ala Pro Met Arg Lys Tyr
    210                 215                 220

Ile Arg Phe Tyr Arg Asp Phe Val Leu Ala Leu Asn Ser Ala Leu Ala
225                 230                 235                 240

Ala Asp Asp Arg Val Glu Ile Cys Gln Leu Pro Val Gly Asp Gly Val
                245                 250                 255

Thr Leu Cys Arg Arg Val Lys
            260

<210> SEQ ID NO 75
<211> LENGTH: 585
<212> TYPE: PRT
<213> ORGANISM: Zea mays
<220> FEATURE:
<221> NAME/KEY: VARIANT
<222> LOCATION: (1)...(585)
<223> OTHER INFORMATION: Xaa = Any Amino Acid

<400> SEQUENCE: 75

Met Ala Met Ala Ile Ser Ser Ala Leu Pro Cys Ser Leu Leu Val Ala
 1               5                  10                  15

Ala Leu Met Leu Leu Ala Ser Val Val Gln Val Gln Gly Ile Thr Arg
            20                  25                  30

His Tyr Asp Phe Asn Val Thr Met Ala Asn Val Thr Arg Leu Cys Ala
        35                  40                  45

Ser Lys Ser Ile Ile Thr Val Asn Gly Gln Phe Pro Gly Pro Lys Ile
```

-continued

```
                50                  55                  60
Val Ala Arg Glu Gly Asp Arg Leu Val Ile Arg Val Thr Asn His Ala
 65                  70                  75                  80

Gln His Asn Ile Ser Xaa His Trp His Gly Ile Arg Gln Leu Arg Thr
                 85                  90                  95

Gly Trp Ala Asp Gly Pro Ala Tyr Ile Thr Gln Cys Pro Ile Gln Thr
                100                 105                 110

Gly Gln Ser Tyr Val Tyr Asn Tyr Thr Val Val Gly Gln Arg Gly Thr
                115                 120                 125

Leu Trp Trp His Ala His Ile Ser Trp Leu Arg Ala Thr Val Tyr Gly
130                 135                 140

Pro Leu Val Ile Leu Pro Lys Leu Gly Val Pro Tyr Pro Phe Pro Ala
145                 150                 155                 160

Pro Tyr Lys Glu Val Pro Val Ile Phe Gly Glu Trp Trp Leu Ala Asp
                165                 170                 175

Thr Glu Val Val Ile Lys Gln Ala Leu Gln Leu Gly Ala Gly Pro Asn
                180                 185                 190

Val Ser Asp Ala His Thr Ile Asn Gly Leu Pro Trp Pro Leu Tyr Asn
195                 200                 205

Cys Ser Ala Lys Asp Thr Tyr Lys Leu Lys Val Lys Pro Gly Lys Thr
210                 215                 220

Tyr Met Leu Arg Leu Ile Asn Ala Ala Leu Asn Asp Glu Leu Phe Phe
225                 230                 235                 240

Ser Val Ala Asn His Ser Leu Thr Val Val Glu Val Asp Ala Val Tyr
                245                 250                 255

Val Lys Pro Phe Thr Val Asp Thr Leu Leu Ile Ala Pro Gly Gln Thr
                260                 265                 270

Thr Asn Val Leu Leu Ala Ala Lys Pro Ser Tyr Pro Gly Ala Asn Tyr
                275                 280                 285

Tyr Met Ser Ala Ala Pro Tyr Ser Thr Ala Arg Pro Ala Thr Phe Asp
290                 295                 300

Asn Thr Thr Val Ala Gly Ile Leu Glu Tyr Glu Leu Tyr Pro Asp Ala
305                 310                 315                 320

Pro Arg Pro Ser Ala Ser Ala Gly Ser Phe Asn Glu Ala Leu Pro Leu
                325                 330                 335

Tyr Arg Pro Thr Leu Pro Gln Leu Asn Asp Thr Asn Phe Val Gly Asn
                340                 345                 350

Phe Thr Ala Lys Leu Arg Ser Leu Ala Thr Pro Arg Tyr Pro Ala Ala
                355                 360                 365

Val Pro Arg Thr Val Asp Arg Arg Phe Phe Ala Val Gly Leu Gly
370                 375                 380

Thr His Pro Cys Pro Ala Asn Ala Thr Cys Gln Gly Pro Thr Asn Thr
385                 390                 395                 400

Thr Gln Phe Ala Ala Ser Val Asn Asn Val Ser Phe Val Leu Pro Thr
                405                 410                 415

Lys Ala Leu Leu His Ser His Phe Thr Gly Leu Ser Ser Gly Val Tyr
                420                 425                 430

Ser Pro Asp Phe Pro Val Ala Pro Leu Ala Pro Phe Asn Tyr Thr Gly
                435                 440                 445

Thr Pro Pro Asn Asn Thr Asn Val Ala Ser Gly Thr Lys Leu Met Val
                450                 455                 460

Val Pro Tyr Gly Ala Asn Val Glu Leu Val Met Gln Gly Thr Ser Ile
465                 470                 475                 480
```

-continued

```
Leu Gly Val Glu Ser His Pro Leu His Leu His Gly Phe Asn Phe Phe
                485                 490                 495
Val Val Gly Gln Gly Tyr Gly Asn Tyr Asp Pro Val Asn Asp Pro Ser
            500                 505                 510
Lys Phe Asn Leu Val Asp Pro Val Glu Arg Asn Thr Val Gly Val Pro
        515                 520                 525
Ala Gly Gly Trp Val Ala Ile Arg Phe Leu Ala Asp Asn Pro Gly Val
    530                 535                 540
Trp Phe Met His Cys His Leu Glu Ala His Thr Thr Trp Gly Leu Arg
545                 550                 555                 560
Met Ala Trp Leu Val Leu Asp Gly Ser Leu Pro His Gln Lys Leu Leu
                565                 570                 575
Pro Pro Pro Ser Asp Leu Pro Lys Cys
            580                 585

<210> SEQ ID NO 76
<211> LENGTH: 1859
<212> TYPE: DNA
<213> ORGANISM: Zea mays
<220> FEATURE:
<221> NAME/KEY: CDS
<222> LOCATION: (79)...(1656)

<400> SEQUENCE: 76
gtcgacccac gcgtccgcta aaacccaaac gaaataaaag gaagaggtca aaaaataaaa        60
ggtgttgtgc aatcgatc atg gtg acc gtg gcc aag atc gcc atg gag tgg       111
                    Met Val Thr Val Ala Lys Ile Ala Met Glu Trp
                     1               5                  10 ctc caa gac cct ctg agc tgg gtg ttc ctg ggc acg ctg gcc ttg gtg       159
Leu Gln Asp Pro Leu Ser Trp Val Phe Leu Gly Thr Leu Ala Leu Val
            15                  20                  25 gtc ctg cag ctg cga cga cgg ggc aaa gcg ccg ctg ccg ccc ggg ccg       207
Val Leu Gln Leu Arg Arg Arg Gly Lys Ala Pro Leu Pro Pro Gly Pro
        30                  35                  40 aag ccg ctg ccg atc gtg ggc aac atg gcg atg atg gac cag ctg acc       255
Lys Pro Leu Pro Ile Val Gly Asn Met Ala Met Met Asp Gln Leu Thr
    45                  50                  55 cac cgc ggg ctg gcg gcg ctg gcc gag agg tac ggc ggg ctg ctg cac       303
His Arg Gly Leu Ala Ala Leu Ala Glu Arg Tyr Gly Gly Leu Leu His
60                  65                  70                  75 ctc cgc ctg ggc cgg ctg cac gcg ttc gcg gtg tcg acg ccc gag tac       351
Leu Arg Leu Gly Arg Leu His Ala Phe Ala Val Ser Thr Pro Glu Tyr
                80                  85                  90 gcg cgc gag gtg ctg cag gcg cag gac ggc gcg ttc tcg aac cgg ccg       399
Ala Arg Glu Val Leu Gln Ala Gln Asp Gly Ala Phe Ser Asn Arg Pro
            95                 100                 105 gcc act atc gcc atc gcg tac ctg acg tac gac cgc gcc gac atg gcg       447
Ala Thr Ile Ala Ile Ala Tyr Leu Thr Tyr Asp Arg Ala Asp Met Ala
        110                 115                 120 ttc gcg cac tac ggg ccc ttc tgg cgc cag atg cgc aag ctg tgc gtg       495
Phe Ala His Tyr Gly Pro Phe Trp Arg Gln Met Arg Lys Leu Cys Val
    125                 130                 135 atg aag ctg ttc agc cgg cgc cgc gcc gag acg tgg gtg gcc gtg cgc       543
Met Lys Leu Phe Ser Arg Arg Arg Ala Glu Thr Trp Val Ala Val Arg
140                 145                 150                 155 gac gag tgc gcg gcg ctg gtc cgc gcc gtg gcg tcc ggc ggc ggc ggc       591
Asp Glu Cys Ala Ala Leu Val Arg Ala Val Ala Ser Gly Gly Gly Gly
                160                 165                 170
```

-continued

| | |
|---|---|
| ggc ggc gag gcc gtg aac ctg ggc gag ctc atc ttc aac ctg acc aag<br>Gly Gly Glu Ala Val Asn Leu Gly Glu Leu Ile Phe Asn Leu Thr Lys<br>          175                 180                   185 | 639 |
| aac gtg acg ttc cgc gcc gcc ttc ggc acc cgc gac ggc gag gac cag<br>Asn Val Thr Phe Arg Ala Ala Phe Gly Thr Arg Asp Gly Glu Asp Gln<br>        190                 195                   200 | 687 |
| gag gag ttc atc gcc atc ctg cag gag ttc tcg aag ctg ttc ggc gcc<br>Glu Glu Phe Ile Ala Ile Leu Gln Glu Phe Ser Lys Leu Phe Gly Ala<br>205                   210                   215 | 735 |
| ttc aac gtc gtc gac ttc ctg ccg tgg ctg agc tgg atg gac ctg cag<br>Phe Asn Val Val Asp Phe Leu Pro Trp Leu Ser Trp Met Asp Leu Gln<br>220                   225                 230                235 | 783 |
| ggc atc aac cgc cgc ctc cgc gcc gca cga tcc gcg ctg gac cgg ttc<br>Gly Ile Asn Arg Arg Leu Arg Ala Ala Arg Ser Ala Leu Asp Arg Phe<br>               240                   245                   250 | 831 |
| atc gac aag atc atc gac gag cac gtg agg cgg ggg aag aac ccc gac<br>Ile Asp Lys Ile Ile Asp Glu His Val Arg Arg Gly Lys Asn Pro Asp<br>               255                 260                 265 | 879 |
| gac gcc gac gcc gac atg gtc gac gac atg ctc gcc ttc ttc gcc gag<br>Asp Ala Asp Ala Asp Met Val Asp Asp Met Leu Ala Phe Phe Ala Glu<br>270                   275                 280 | 927 |
| gcc aag ccg ccc aag aag ggg ccc gcc gcc gcc gcg gac ggt gac gac<br>Ala Lys Pro Pro Lys Lys Gly Pro Ala Ala Ala Ala Asp Gly Asp Asp<br>285                   290                 295 | 975 |
| ctg cac aac acc ctc cgg ctc acg cgc gac aat atc aag gct atc atc<br>Leu His Asn Thr Leu Arg Leu Thr Arg Asp Asn Ile Lys Ala Ile Ile<br>300                   305                   310                315 | 1023 |
| atg gac gtg atg ttt ggc ggg acg gag acg gtg gcg tcg gcg atc gag<br>Met Asp Val Met Phe Gly Gly Thr Glu Thr Val Ala Ser Ala Ile Glu<br>               320                   325                 330 | 1071 |
| tgg gcg atg gcg gag atg atg cac agc ccc gac gac ctg cgc cgg ctg<br>Trp Ala Met Ala Glu Met Met His Ser Pro Asp Asp Leu Arg Arg Leu<br>               335                 340                 345 | 1119 |
| cag cag gag ctc gcc gac gtc gtg ggc ctg gac cgg aac gtg aac gag<br>Gln Gln Glu Leu Ala Asp Val Val Gly Leu Asp Arg Asn Val Asn Glu<br>               350                 355                 360 | 1167 |
| tcg gac ctg gac aag ctc ccc ttc ctc aag tgc gtc atc aag gag acg<br>Ser Asp Leu Asp Lys Leu Pro Phe Leu Lys Cys Val Ile Lys Glu Thr<br>365                   370                 375 | 1215 |
| ctc cgg ctg cac ccg ccg atc ccg ctg ctc ctg cac gag acc gcc ggc<br>Leu Arg Leu His Pro Pro Ile Pro Leu Leu Leu His Glu Thr Ala Gly<br>380                   385                 390                395 | 1263 |
| gac tgc gtc gtg ggc ggc tac tcc gtg ccc agg ggc tcc cgc gtc atg<br>Asp Cys Val Val Gly Gly Tyr Ser Val Pro Arg Gly Ser Arg Val Met<br>               400                   405                 410 | 1311 |
| gtc aac gtg tgg gcc atc ggc cgc cac cgc gcc tcg tgg aag gac gcc<br>Val Asn Val Trp Ala Ile Gly Arg His Arg Ala Ser Trp Lys Asp Ala<br>               415                 420                 425 | 1359 |
| gac gcg ttc cgg ccg tcg cgc ttc acg ccc gag ggc gag gcc gcg ggg<br>Asp Ala Phe Arg Pro Ser Arg Phe Thr Pro Glu Gly Glu Ala Ala Gly<br>430                   435                 440 | 1407 |
| ctc gac ttc aag ggc ggc tgc ttc gag ttc ctg ccc ttc ggc tcc ggc<br>Leu Asp Phe Lys Gly Gly Cys Phe Glu Phe Leu Pro Phe Gly Ser Gly<br>445                   450                 455 | 1455 |
| cgc cgc tcg tgc ccc ggc acg gcg ctg ggc ctg tac gcg ctg gag ctc<br>Arg Arg Ser Cys Pro Gly Thr Ala Leu Gly Leu Tyr Ala Leu Glu Leu<br>460                   465                 470                475 | 1503 |
| gcc gtc gcc cag ctc gcg cac ggc ttc aac tgg tcg ctg ccc gac ggc<br>Ala Val Ala Gln Leu Ala His Gly Phe Asn Trp Ser Leu Pro Asp Gly<br>               480                 485                 490 | 1551 |

-continued

```
atg aag ccc tcg gag ctg gac atg ggc gac gtc ttc ggc ctc acc gcg       1599
Met Lys Pro Ser Glu Leu Asp Met Gly Asp Val Phe Gly Leu Thr Ala
            495                 500                 505 ccg cgc gcc acg agg ctc tac gcc gtg cct acg ccc cgg ctc aac tgc       1647
Pro Arg Ala Thr Arg Leu Tyr Ala Val Pro Thr Pro Arg Leu Asn Cys
        510                 515                 520 ccc ttg tac tgacgccatg cgcgggcgac tgccattacc atcgtccct                1696
Pro Leu Tyr
    525 cgggtgggtg tggggtacgg gggtaggagt ttggtgcctt tctctgtcgt ctttttccc      1756 tttaaaaaac atgcctggtc gatgttgtag ggtgtgttgt agacagccat tatcaatttt     1816 ttttattctc aaaaaaaaaa aaaaaaaaaa aaagggcggc cgc                       1859

<210> SEQ ID NO 77
<211> LENGTH: 1218
<212> TYPE: DNA
<213> ORGANISM: Zea mays
<220> FEATURE:
<221> NAME/KEY: CDS
<222> LOCATION: (112)...(900)

<400> SEQUENCE: 77
gtcgacccac gcgtccgata cccgacgcgc aaccagtgcc gcacccagac cagatctccg     60
cgacatatca gtcgttcgtc cagctaactg cactgcactg cactgcacgc a atg gcc     117
                                                        Met Ala
                                                          1 acc acg gcg acc gag gcg gcc aag gct gca ccg gcg cag gag cag cag       165
Thr Thr Ala Thr Glu Ala Ala Lys Ala Ala Pro Ala Gln Glu Gln Gln
        5                   10                  15 gcc aac ggc aac ggc aac ggc gag cag aag acg cgc cac tcc gag gtc       213
Ala Asn Gly Asn Gly Asn Gly Glu Gln Lys Thr Arg His Ser Glu Val
    20                  25                  30 ggc cac aag agc ctg ctc aag agc gac gac ctg tac cag tac atc ctg       261
Gly His Lys Ser Leu Leu Lys Ser Asp Asp Leu Tyr Gln Tyr Ile Leu
35                  40                  45                  50 gac acg agc gtg tac ccg cgg gag ccg gag agc atg aag gag ctg cgc       309
Asp Thr Ser Val Tyr Pro Arg Glu Pro Glu Ser Met Lys Glu Leu Arg
                55                  60                  65 gag atc acc gcc aag cac cca tgg aac ctg atg acc acc tcc gcc gac       357
Glu Ile Thr Ala Lys His Pro Trp Asn Leu Met Thr Thr Ser Ala Asp
            70                  75                  80 gag ggc cag ttc ctc aac atg ctc atc aag ctc atc ggc gcc aag aag       405
Glu Gly Gln Phe Leu Asn Met Leu Ile Lys Leu Ile Gly Ala Lys Lys
        85                  90                  95 acc atg gag atc ggc gtc tac acc ggc tac tcg ctc ctc gcc acc gcg       453
Thr Met Glu Ile Gly Val Tyr Thr Gly Tyr Ser Leu Leu Ala Thr Ala
    100                 105                 110 ctc gca ctc ccg gag gac ggc acg atc ttg gcc atg gac atc aac cgc       501
Leu Ala Leu Pro Glu Asp Gly Thr Ile Leu Ala Met Asp Ile Asn Arg
115                 120                 125                 130 gag aac tac gag cta ggc ctt ccc tgc atc aac aag gcc ggc gtg ggc       549
Glu Asn Tyr Glu Leu Gly Leu Pro Cys Ile Asn Lys Ala Gly Val Gly
                135                 140                 145 cac aag atc gac ttc cgc gag ggc ccc gcg ctc ccc gtc ctg gac gac       597
His Lys Ile Asp Phe Arg Glu Gly Pro Ala Leu Pro Val Leu Asp Asp
            150                 155                 160 ctc gtg gcg gac aag gag cag cac ggg tcg ttc gac ttc gcc ttc gtg       645
Leu Val Ala Asp Lys Glu Gln His Gly Ser Phe Asp Phe Ala Phe Val
        165                 170                 175
```

-continued

| | |
|---|---|
| gac gcc gac aag gac aac tac ctc agc tac cac gag cgg ctc ctg aag<br>Asp Ala Asp Lys Asp Asn Tyr Leu Ser Tyr His Glu Arg Leu Leu Lys<br>    180                         185                        190 | 693 |
| ctg gtg agg ccc ggc ggc ctc atc ggc tac gac aac acg ctg tgg aac<br>Leu Val Arg Pro Gly Gly Leu Ile Gly Tyr Asp Asn Thr Leu Trp Asn<br>195                        200                        205                    210 | 741 |
| ggc tcc gtc gtg ctc ccc gac gac gcg ccc atg cgc aag tac atc cgc<br>Gly Ser Val Val Leu Pro Asp Asp Ala Pro Met Arg Lys Tyr Ile Arg<br>                    215                        220                        225 | 789 |
| ttc tac cgc gac ttc gtc ctc gcc ctc aac agc gcg ctc gcc gcc gac<br>Phe Tyr Arg Asp Phe Val Leu Ala Leu Asn Ser Ala Leu Ala Ala Asp<br>          230                        235                        240 | 837 |
| gac cgc gtc gag atc tgc cag ctc ccc gtc ggc gac ggc gtc acg ctc<br>Asp Arg Val Glu Ile Cys Gln Leu Pro Val Gly Asp Gly Val Thr Leu<br>               245                        250                        255 | 885 |
| tgc cgc cgc gtc aag tgaaaaaaag aagaagaaga aaaaaaacat aatacccctgc<br>Cys Arg Arg Val Lys<br>      260 | 940 |
| gttcctgctg ccccggctgt ctggcccca ctactgccac cgacggcggc gccgaacccc | 1000 |
| cgttccaatc atcatatcgt agacgacgcg cagcattaaa ctatcaatca ccggatctgg | 1060 |
| ctctttcttg gccctgtact gtactattaa tgttccgttc ttgttttttt attcggaatt | 1120 |
| gtcgccgttt cagtatacgt aaatctcgag gtcgataata cagtaatact accaatttaa | 1180 |
| ctgtataaaa aaaaaaaaaa aaaaaaaagg gcggccgc | 1218 |

<210> SEQ ID NO 78
<211> LENGTH: 2230
<212> TYPE: DNA
<213> ORGANISM: Zea mays
<220> FEATURE:
<221> NAME/KEY: CDS
<222> LOCATION: (170)...(1924)
<220> FEATURE:
<221> NAME/KEY: misc_feature
<222> LOCATION: (1)...(2230)
<223> OTHER INFORMATION: n = A,T,C or G

<400> SEQUENCE: 78

| | |
|---|---|
| tggtacgcnt gcaggtaccg gtccggantt cccgggtcga cccacgcgtc cgcattattc | 60 |
| ttcctccacc catctcttga gtcgcctggc cggccgccgt cttggttccc ctctagagct | 120 |
| caacagcaga gcagctgtgt agcatagagc gaggtttaac catcagcgc atg gcc atg<br>                                                                                         Met Ala Met<br>                                                                                            1 | 178 |
| gcg atc tcc tct gct ctt ccg tgc tcc ctc ctc gtg gcg gcc ctg atg<br>Ala Ile Ser Ser Ala Leu Pro Cys Ser Leu Leu Val Ala Ala Leu Met<br>  5                         10                            15 | 226 |
| ctc ctc gcc tcc gtc gtc caa gtg caa ggc atc acg agg cac tac gac<br>Leu Leu Ala Ser Val Val Gln Val Gln Gly Ile Thr Arg His Tyr Asp<br>20                        25                        30                        35 | 274 |
| ttc aat gtg acc atg gcg aac gtg aca cgg ctg tgc gcc agc aag agc<br>Phe Asn Val Thr Met Ala Asn Val Thr Arg Leu Cys Ala Ser Lys Ser<br>                    40                            45                        50 | 322 |
| atc atc acg gtg aac ggg cag ttc ccc ggg ccc aag atc gtg gcg agg<br>Ile Ile Thr Val Asn Gly Gln Phe Pro Gly Pro Lys Ile Val Ala Arg<br>                         55                          60                        65 | 370 |
| gaa ggc gac cgg ctc gtc atc cgc gtc acc aac cac gcc cag cac aac<br>Glu Gly Asp Arg Leu Val Ile Arg Val Thr Asn His Ala Gln His Asn<br>      70                          75                            80 | 418 |
| atc tcg ntg cac tgg cac ggc atc cgg cag ctg cgc acg ggg tgg gcg | 466 |

-continued

```
                Ile Ser Xaa His Trp His Gly Ile Arg Gln Leu Arg Thr Gly Trp Ala
                    85                  90                  95 gac ggg ccg gcg tac atc acg cag tgc ccg atc cag acg ggg cag agt         514
Asp Gly Pro Ala Tyr Ile Thr Gln Cys Pro Ile Gln Thr Gly Gln Ser
100                 105                 110                 115 tac gtg tac aac tac acc gtc gtg ggg cag cgc ggc acg ctg tgg tgg         562
Tyr Val Tyr Asn Tyr Thr Val Val Gly Gln Arg Gly Thr Leu Trp Trp
                120                 125                 130 cac gcg cac atc tcc tgg ctg cgc gcc acc gtc tac ggg ccc ctc gtc         610
His Ala His Ile Ser Trp Leu Arg Ala Thr Val Tyr Gly Pro Leu Val
            135                 140                 145 atc ctg ccc aag ctc ggc gtc ccc tac ccg ttc ccg gcg ccc tac aag         658
Ile Leu Pro Lys Leu Gly Val Pro Tyr Pro Phe Pro Ala Pro Tyr Lys
        150                 155                 160 gag gtc ccc gtc atc ttc ggt gag tgg tgg ctg gcg gac acg gag gtg         706
Glu Val Pro Val Ile Phe Gly Glu Trp Trp Leu Ala Asp Thr Glu Val
    165                 170                 175 gtg atc aag cag gcg ctt cag ctc ggc gct ggc ccc aat gtc tct gac         754
Val Ile Lys Gln Ala Leu Gln Leu Gly Ala Gly Pro Asn Val Ser Asp
180                 185                 190                 195 gcc cac acc atc aac ggc ctg cca tgg ccg ctc tac aac tgc tct gcc         802
Ala His Thr Ile Asn Gly Leu Pro Trp Pro Leu Tyr Asn Cys Ser Ala
                200                 205                 210 aaa gac acg tac aag ctg aag gtg aag ccc ggg aag acg tac atg ctg         850
Lys Asp Thr Tyr Lys Leu Lys Val Lys Pro Gly Lys Thr Tyr Met Leu
            215                 220                 225 cgc ctc atc aac gcg gcg ctc aac gac gag ctc ttc ttc tcc gtc gcc         898
Arg Leu Ile Asn Ala Ala Leu Asn Asp Glu Leu Phe Phe Ser Val Ala
        230                 235                 240 aac cac tcg ctc acg gtc gtc gag gtc gac gcc gtc tac gtc aag ccc         946
Asn His Ser Leu Thr Val Val Glu Val Asp Ala Val Tyr Val Lys Pro
    245                 250                 255 ttc acc gtc gac acg ctg ctc atc gcg ccg ggc cag acc acc aac gtg         994
Phe Thr Val Asp Thr Leu Leu Ile Ala Pro Gly Gln Thr Thr Asn Val
260                 265                 270                 275 ctg ctc gcc gcc aag ccg tcc tac ccg ggc gcc aac tac tac atg tcc        1042
Leu Leu Ala Ala Lys Pro Ser Tyr Pro Gly Ala Asn Tyr Tyr Met Ser
                280                 285                 290 gcc gcg ccc tac tcc acc gcc agg ccg gcc acc ttc gac aac acc acc        1090
Ala Ala Pro Tyr Ser Thr Ala Arg Pro Ala Thr Phe Asp Asn Thr Thr
            295                 300                 305 gtc gcc ggc atc ctc gag tac gag ctg tac ccc gac gcg ccc cgg ccc        1138
Val Ala Gly Ile Leu Glu Tyr Glu Leu Tyr Pro Asp Ala Pro Arg Pro
        310                 315                 320 tcc gcc tcc gcg ggg agc ttc aac gag gcc ctg ccg ctc tac aga ccg        1186
Ser Ala Ser Ala Gly Ser Phe Asn Glu Ala Leu Pro Leu Tyr Arg Pro
    325                 330                 335 acc ctg ccg cag ctc aac gac acc aac ttc gtc ggc aac ttc acg gcc        1234
Thr Leu Pro Gln Leu Asn Asp Thr Asn Phe Val Gly Asn Phe Thr Ala
340                 345                 350                 355 aag ctc cgc agc ctc gcg acg ccg cgg tac ccg gcg gcc gtg ccg cgg        1282
Lys Leu Arg Ser Leu Ala Thr Pro Arg Tyr Pro Ala Ala Val Pro Arg
                360                 365                 370 acg gtg gac agg cgg ttc ttc ttc gcg gtc ggg ctc ggc acg cac ccg        1330
Thr Val Asp Arg Arg Phe Phe Phe Ala Val Gly Leu Gly Thr His Pro
            375                 380                 385 tgc ccc gcc aac gcc acg tgc cag ggc ccc acc aac acc acg cag ttc        1378
Cys Pro Ala Asn Ala Thr Cys Gln Gly Pro Thr Asn Thr Thr Gln Phe
        390                 395                 400
```

| | | | | | | | | | | | | |
|---|---|---|---|---|---|---|---|---|---|---|---|---|
| gcg | gcg | tcc | gtc | aac | aac | gtc | tcc | ttc | gtg | ctc | ccc | acc | aag | gcg | ctg | 1426 |
| Ala | Ala | Ser | Val | Asn | Asn | Val | Ser | Phe | Val | Leu | Pro | Thr | Lys | Ala | Leu | |
| 405 | | | | 410 | | | | | 415 | | | | | | | |

```
gcg gcg tcc gtc aac aac gtc tcc ttc gtg ctc ccc acc aag gcg ctg   1426
Ala Ala Ser Val Asn Asn Val Ser Phe Val Leu Pro Thr Lys Ala Leu
405                 410                 415 ctg cac tcc cac ttc acc ggc ctg tcc agc ggc gtc tac tcg ccg gac   1474
Leu His Ser His Phe Thr Gly Leu Ser Ser Gly Val Tyr Ser Pro Asp
420                 425                 430                 435 ttc ccc gtc gcg ccc ctg gcg ccg ttc aac tac acg ggg acg ccg ccc   1522
Phe Pro Val Ala Pro Leu Ala Pro Phe Asn Tyr Thr Gly Thr Pro Pro
                440                 445                 450 aac aac acc aac gtg gcc agc ggg acc aag ctc atg gtc gtc ccg tac   1570
Asn Asn Thr Asn Val Ala Ser Gly Thr Lys Leu Met Val Val Pro Tyr
        455                 460                 465 ggc gcc aac gtg gag ctc gtc atg cag ggc acc agc atc ctc ggc gtc   1618
Gly Ala Asn Val Glu Leu Val Met Gln Gly Thr Ser Ile Leu Gly Val
    470                 475                 480 gag agc cac ccg ctg cac ctg cac ggc ttc aac ttc ttc gtg gtc ggc   1666
Glu Ser His Pro Leu His Leu His Gly Phe Asn Phe Phe Val Val Gly
485                 490                 495 caa ggg tac ggc aac tac gac ccc gtc aac gac ccg tcc aag ttc aac   1714
Gln Gly Tyr Gly Asn Tyr Asp Pro Val Asn Asp Pro Ser Lys Phe Asn
500                 505                 510                 515 ctc gtc gac ccc gtc gag cgc aac acc gtc ggc gtg ccg gcc ggc gga   1762
Leu Val Asp Pro Val Glu Arg Asn Thr Val Gly Val Pro Ala Gly Gly
                520                 525                 530 tgg gtg gcc atc cgc ttc ctc gcc gac aac ccc ggg gtc tgg ttc atg   1810
Trp Val Ala Ile Arg Phe Leu Ala Asp Asn Pro Gly Val Trp Phe Met
                535                 540                 545 cat tgc cat ttg gag gcg cac aca aca tgg ggc ctc agg atg gca tgg   1858
His Cys His Leu Glu Ala His Thr Thr Trp Gly Leu Arg Met Ala Trp
        550                 555                 560 ttg gtg ctc gac ggc agc ctc ccg cac cag aag ctg ctc ccg ccg ccg   1906
Leu Val Leu Asp Gly Ser Leu Pro His Gln Lys Leu Leu Pro Pro Pro
565                 570                 575 tca gac tta ccc aaa tgt tgattagact cttcctctat ctctatcctg          1954
Ser Asp Leu Pro Lys Cys
580             585 ccggtcgctt caaattaaag ggaatgtgaa ttagacaaat gtttgtttgt ttttttgttt  2014
actttcttca ttgccaattg caattttttc aacttgcatt ttaactagtc cgttccgttc  2074
ctagctgacc tggactttt tgtaattttt ttcttccatt tgtttgccac cacaaatgtt  2134
tttgtacact cctctgaaaa taaagaatgg cgtgacttgc accagataaa aaaaaaaaa   2194 aaaaaaaaa aaaaaaaaa aaaaagggc ggccgc                              2230

<210> SEQ ID NO 79
<211> LENGTH: 25
<212> TYPE: DNA
<213> ORGANISM: Zea mays

<400> SEQUENCE: 79
atggtgaccg tggccaagat cgcca                                         25

<210> SEQ ID NO 80
<211> LENGTH: 25
<212> TYPE: DNA
<213> ORGANISM: Zea mays

<400> SEQUENCE: 80
tcagtacaag gggcagttga gccgg                                         25
```

```
<210> SEQ ID NO 81
<211> LENGTH: 25
<212> TYPE: DNA
<213> ORGANISM: Zea mays

<400> SEQUENCE: 81
atggccacca cggcgaccga ggcgg                                               25

<210> SEQ ID NO 82
<211> LENGTH: 25
<212> TYPE: DNA
<213> ORGANISM: Zea mays

<400> SEQUENCE: 82
tcacttgacg cggcggcaga gcgtg                                               25

<210> SEQ ID NO 83
<211> LENGTH: 25
<212> TYPE: DNA
<213> ORGANISM: Zea mays

<400> SEQUENCE: 83
atggccatgg cgatctcctc tgctc                                               25

<210> SEQ ID NO 84
<211> LENGTH: 25
<212> TYPE: DNA
<213> ORGANISM: Zea mays

<400> SEQUENCE: 84
tcaacatttg ggtaagtctg acggc                                               25

<210> SEQ ID NO 85
<211> LENGTH: 36
<212> TYPE: DNA
<213> ORGANISM: Artificial Sequence
<220> FEATURE:
<223> OTHER INFORMATION: Designed oligonucleotide based upon the adapter
      sequence and poly T to remove clones which have a
      poly A tail but no cDNA.

<400> SEQUENCE: 85
tcgacccacg cgtccgaaaa aaaaaaaaaa aaaaaa                                   36
```

GENES ENCODING ENZYMES FOR LIGNIN BIOSYNTHESIS AND USES THEREOF

CROSS-REFERENCE TO RELATED APPLICATIONS

This application is a continuation of U.S. patent application Ser. No. 09/076,851, filed May 12, 1998, now abandoned, and which claims the benefit of U.S. Provisional Application No. 60/057,082, filed Aug. 27, 1997, all of which are hereby incorporated by reference.

TECHNICAL FIELD

The present invention relates generally to plant molecular biology. More specifically, it relates to nucleic acids and methods for modifying the lignin content in plants.

BACKGROUND OF THE INVENTION

Differences in plant cell wall composition account for much of the variation in chemical reactivity, mechanical strength, and energy content of plant material. In turn, differences in chemical and mechanical properties of plant material greatly impact the utilization of plant biomass by agriculture and industry. One abundant component of many types of plant cells, and one which has garnered increasing attention because of its importance in plant utilization, are lignins.

Lignins are a class of complex heterpolymers associated with the polysaccharide components of the wall in specific plant cells. Lignins play an essential role in providing rigidity, compressive strength, and structural support to plant tissues. They also render cell walls hydrophobic allowing the conduction of water and solutes. Reflecting their importance, lignins represent the second most abundant organic compound on Earth after cellulose accounting for approximately 25% of plant biomass. Lignins result from the oxidative coupling of three monomers: coumaryl, coniferyl, and sinapyl alcohols. Variability in lignin structure is dependent, in part, upon the relative proportion of the three constitutive monomers.

The biosynthesis of lignins proceeds from phenylalanine through the phenylpropanoid pathway to the cinnamoyl CoAs which are the general precursors of a wide range of phenolic compounds. The enzymes involved in this pathway are phenylalanine ammonia-lyase (PAL), cinnamate-4-hydroxylase (C4H), 4-coumarate-3-hydroxylase (C3H), O-methyltransferase (OMT), ferulate-5-hydroxylase (F5H), caffeoyl-CoA 3-O-methyltransferase (CCoA-OMT), and 4-coumarate:CoA ligase (4CL). Whetten and Sederoff, *The Plant Cell*, 7: 1001–1013 (1995); Boudet and Grima-Pettenati, *Molecular Breeding*, 2:25–39 (1996).

The lignin specific pathway channels cinnamoyl CoAs towards the synthesis of monolignols and lignins. This pathway involves two reductive enzymes that convert the hydroxycinnamoyl-CoA esters into monolignols: cinnamoyl-CoA reductase (CCR), and cinnamyl alcohol dehydrogenase (CAD).

While lignins are a vital component in terrestrial vascular plants, they often pose an obstacle to the utilization of plant biomass. For example, in the pulp and paper industry lignins have to be separated from cellulose by an expensive and polluting process. Lignin content also limits the digestability of crops consumed by livestock. While reduction of lignin content for such applications is generally desirable, increasing lignin content in plant material intended as a chemical feedstock for production of phenolics, for use as a fuel source, or for improvement in agronomically desirable properties (e.g., standability) is also advantageous. Accordingly, what is needed in the art is the ability to modulate lignin content in plants. The present invention addresses these and other needs.

SUMMARY OF THE INVENTION

Generally, it is the object of the present invention to provide nucleic acids and proteins relating to lignin biosynthesis. It is an object of the present invention to provide antigenic fragments of the proteins of the present invention. It is an object of the present invention to provide transgenic plants comprising the nucleic acids of the present invention. Additionally, it is an object of the present invention to provide methods for modulating, in a transgenic plant, the expression of the nucleic acids of the present invention.

Therefore, in one aspect, the present invention relates to an isolated nucleic acid comprising a member selected from the group consisting of (a) a polynucleotide having at least 60% identity to a polynucleotide encoding a polypeptide selected from the group consisting of SEQ ID NOS:1–18 and 73–75, wherein the polypeptide when presented as an immunogen elicits the production of an antibody which is specifically reactive to the polypeptide; (b) a polynucleotide which is complementary to the polynucleotide of (a); and (c) a polynucleotide comprising at least 25 contiguous nucleotides from a polynucleotide of (a) or (b). In some embodiments, the polynucleotide has a sequence selected from the group consisting of SEQ ID NOS: 19–36 and 76–78. The isolated nucleic acid can be DNA.

In another aspect, the present invention relates to recombinant expression cassettes, comprising a nucleic acid as described, supra, operably linked to a promoter.

In some embodiments, the nucleic acid is operably linked in antisense orientation to the promoter.

In another aspect, the present invention is directed to a host cell transfected with the recombinant expression cassette as described, supra. In some embodiments, the host cell is a sorghum (*Sorghum bicolor*) or maize (*Zea mays*) cell.

In a further aspect, the present invention relates to an isolated protein comprising a polypeptide of at least 10 contiguous amino acids encoded by the isolated nucleic acid referred to, supra. In some embodiments, the polypeptide has a sequence selected from the group consisting of SEQ ID NOS: 1–18 and 73–75.

In another aspect, the present invention relates to an isolated nucleic acid comprising a polynucleotide of at least 25 nucleotides in length which selectively hybridizes under stringent conditions to a nucleic acid selected from the group consisting of SEQ ID NOS: 19–36 and 76–78, or a complement thereof. In some embodiments, the isolated nucleic acid is operably linked to a promoter.

In yet another aspect, the present invention relates to an isolated nucleic acid comprising a polynucleotide, the polynucleotide having at least 80% sequence identity to an identical length of a nucleic acid selected from the group consisting of SEQ ID NOS: 19–36 and 76–78 or a complement thereof.

In another aspect, the present invention relates to an isolated nucleic acid comprising a polynucleotide having a sequence of a nucleic acid amplified from a *Zea mays* nucleic acid library using the primers selected from the group consisting of SEQ ID NOS: 37–72 and 79–84, or complements thereof. In some embodiments, the nucleic acid library is a cDNA library.

In another aspect, the present invention relates to a recombinant expression cassette comprising a nucleic acid amplified from a library as referred to supra, wherein the nucleic acid is operably linked to a promoter. In some embodiments, the present invention relates to a host cell transfected with this recombinant expression cassette In some embodiments, the present invention relates to a protein of the present invention which is produced from this host cell.

In an additional aspect, the present invention is directed to an isolated nucleic acid comprising a polynucleotide encoding a polypeptide wherein: (a) the polypeptide comprises at least 10 contiguous amino acid residues from a first polypeptide selected from the group consisting of SEQ ID NOS: 1–18 and 73–75, wherein said polypeptide, when presented as an immunogen, elicits the production of an antibody which specifically binds to said first polypeptide; (b) the polypeptide does not bind to antisera raised against the first polypeptide which has been fully immunosorbed with the first polypeptide; (c) the polypeptide has a molecular weight in non-glycosylated form within 10% of the first polypeptide.

In a further aspect, the present invention relates to a heterologous promoter operably linked to a non-isolated polynucleotide of the present invention, wherein the polypeptide is encoded by a nucleic acid amplified from a nucleic acid library.

In yet another aspect, the present invention relates to a transgenic plant comprising a recombinant expression cassette comprising a plant promoter operably linked to any of the isolated nucleic acids of the present invention. In some embodiments, the transgenic plant is *Zea mays*. The present invention also provides transgenic seed from the transgenic plant.

In a further aspect, the present invention relates to a method of modulating expression of the genes encoding the proteins of the present invention in a plant, comprising the steps of (a) transforming a plant cell with a recombinant expression cassette comprising a polynucleotide of the present invention operably linked to a promoter; (b) growing the plant cell under plant growing conditions; and (c) inducing expression of the polynucleotide for a time sufficient to modulate expression of the genes in the plant. In some embodiments, the plant is maize. Expression of the genes encoding the proteins of the present invention can be increased or decreased relative to a non-transformed control plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substance capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control which is a native (non-synthetic) endogenous cellular form of the specified nucleic acid or protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, generated to a particular epitope, to bind to that epitope to a detectably greater degree (e.g., at least 2-fold over background) than the antibody binds to substantially all other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "manmade") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "lignin biosynthesis nucleic acid" means a nucleic acid comprising a polynucleotide ("lignin biosynthesis polynucleotide") encoding a lignin biosynthesis polypeptide. A "lignin biosynthesis gene" refers to a non-heterologous genomic form of a full-length lignin biosynthesis polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual,* 2nd ed., Vol. 1–3 (1989); and *Current Protocols in Molecular Biology,* F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays.*

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins—Structure and Molecular Properties,* 2nd ed., T. E. Creighton, W.H. Freeman and Company, New York (1993). Many detailed reviews are available on this subject, such as, for example, those provided by Wold, F., Posttranslational Protein Modifications: Perspectives and Prospects, pp. 1–12 in *Posttranslational Covalent Modification of Proteins*, B. C. Johnson, Ed., Academic Press, New York (1983); Seifter et al., *Meth. Enzymol*. 182: 626–646 (1990) and Rattan et al., *Protein Synthesis: Posttranslational Modifications and Aging*, Ann. N.Y. Acad. Sci. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formyl-methionine. During post-translational modification of the peptide, a methionine residue at the $NH_2$-terminus may be deleted. Accordingly, this invention contemplates the use of both the methionine-containing and the methionineless amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, seeds, fibers, xylem vessels, tracheids, or sclerenchyma. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "lignin biosynthesis polypeptide" refer to one or more amino acid sequences, in glycosylated or non-glycosylated form, involved in the lignin biosynthesis pathway. The term is also inclusive of fragments, variants, homologs, alleles or precursors (e.g., preproproteins or proproteins) thereof. A "lignin biosynthesis protein" comprises a lignin biosynthesis polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual*, Cold Spring Harbor Publications, New York (1988), for a description of immunoassay formats and conditions that can be used to determine selective reactivity.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0.1 suite of programs using default parameters. Altschul et al., *Nucleic Acids Res.* 25:3389–3402 (1997).

As those of ordinary skill in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides, inter alia, compositions and methods for modulating (i.e., increasing or decreasing) the total levels of proteins of the present invention and/or altering their ratios in plants. Thus, the present invention provides utility in such exemplary applications as improving the digestibility of fodder crops, increasing the value of plant material for pulp and paper production, improving the standability of crops, as well as for improving the utility of plant material where lignin content or composition is important, such as the use of plant lignins as a chemical feedstock, or the use of hyperlignified plant material for use as a fuel source. In particular, the polypeptides of the present invention can be expressed at times or in quantities which are not characteristic of non-recombinant plants.

The present invention also provides isolated nucleic acid comprising polynucleotides of sufficient length and complementarity to a lignin biosynthesis gene to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of lignin biosynthesis polypeptides, or for use as immunogens in the preparation and/or screening of antibodies. The isolated nucleic acids of the present invention can also be employed for use in sense or antisense suppression of one or more lignin biosynthesis genes in a host cell, tissue, or plant. Attachment of chemical agents which bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identity insertion sequence inactivated lignin biosynthesis genes from a cDNA library prepared from insertion sequence mutagenized plants. Progeny seed from the plants comprising the desired inactivated gene can be grown to a plant to study the phenotypic changes characteristic of that inactivation. See, *Tools to Determine the Function of Genes,* 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention also provides isolated proteins comprising polypeptides including an amino acid sequence from the lignin biosynthesis polypeptides (e.g., preproenzyme, proenzyme, or enzymes) as disclosed herein. The present invention also provides proteins comprising at least one epitope from a lignin biosynthesis polypeptide. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of lignin biosynthesis polypeptides.

The isolated nucleic acids of the present invention can be used over a broad range of plant types, including species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea,* and *Populus.*

Nucleic Acids

The present invention provides, inter alia, isolated nucleic acids of RNA, DNA, and analogs and/or chimeras thereof, comprising a lignin biosynthesis polynucleotide encoding such enzymes as: cinnamate-4-hydroxylase (C4H), 4-coumarate-3-hydroxylase (C3H), caffeic O-methyltransferase (C-OMT), ferulate-5-hydroxylase (F5H), caffeoyl-CoA 3-O-methyltransferase (CCoA-OMT), 4-coumarate:CoA ligase (4CL), cinnamoyl-CoA reductase (CCR), cinnamyl alcohol dehydrogenase (CAD), as well as diphenyl oxidase (DPO), a laccase involved in monomer polymerization.

The lignin biosynthesis nucleic acids of the present invention comprise an isolated lignin biosynthesis polynucleotides which, are inclusive of:

(a) a polynucleotide encoding a lignin biosynthesis polypeptide of SEQ ID NOS: 1–18 and 73–75 and conservatively modified and polymorphic variants thereof, including exemplary polynucleotides of SEQ ID NOS: 19–36 and 76–78;

(b) a polynucleotide which is the product of amplification from a *Zea mays* nucleic acid library using primer pairs from amongst the consecutive pairs from SEQ ID NOS: 37–72 and 79–84, which amplify polynucleotides having substantial identity to polynucleotides from amongst those having SEQ ID NOS: 19–36 and 76–78;

(c) a polynucleotide which selectively hybridizes to a polynucleotide of (a) or (b);

(d) a polynucleotide having at least 60% sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e); and (g) a polynucleotide comprising at least 15 contiguous nucleotides from a polynucleotide of (a), (b), (c), (d), (e), or (f).

A. Polynucleotides Encoding A Protein of SEQ ID NOS: 1–18 and 73–75 or Conservatively Modified or Polymorphic Variants Thereof As indicated in (a), supra, the present invention provides isolated heterologous nucleic acids comprising a lignin biosynthesis polynucleotide, wherein the polynucleotide encodes a lignin biosynthesis polypeptide, disclosed herein in SEQ ID NOS: 1–18 and 73–75, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 19–36 and 76–78, and silent variations of polynucleotides encoding a polypeptide of SEQ ID NOS: 1–18 and 73–75. The present invention further provides isolated nucleic acids comprising polynucleotides encoding conservatively modified variants of a polypeptide of SEQ ID NOS: 1–18 and 73–75. Conservatively modified variants can be used to generate or select antibodies immunoreactive to the non-variant polypeptide. Additionally, the present invention further provides isolated nucleic acids comprising polynucleotides encoding one or more polymorphic (allelic) variants of polypeptides/polynucleotides. Polymorphisms are frequently used to follow segregation of chromosomal regions in, for example, marker assisted selection methods for crop improvement. Exemplary polymorphisms are provided in Table I.

TABLE I

SEQ. ID NO.:20
Position of Polymorphism

| At/Between Nucleotide No(s). | Codon No. | Polymorphic Variants | Encoded Amino Acid(s) |
|---|---|---|---|
| 248 | 31 | T, C | Leu |
| 376 | 141 | A, C | Arg |
| 719 | 188 | C, T | Ala |
| 1169 | 338 | T, C | Ile |
| 1431 | 426 | A, C | Lys, Gln |
| 1454 | 433 | A, C | Gly |
| 1613 | 486 | T, C | Asp |
| 1820 | 555 | G, C | Gln, His |
| 1846 | | A, G | |
| 1851 | | C, G | |
| 1859 | | A, G | |
| 2021, 2022 | | G (Insertion) | |
| 2075 | | T, C | |

4-coumarate:CoA ligase is coded for by the polypeptides of SEQ ID NOS: 1, 2, and 3 which are encoded for by the nucleic acids of SEQ ID NOS:19, 20, and 21, respectively.

Caffeic O-methyltransferase (C-OMT) is coded for by the polypeptides of SEQ ID NOS: 4, 5, 6, and 7 which are encoded for by the nucleic acids of SEQ ID NOS: 22, 23, 24, and 25, respectively.

Cinnamate-4-hydroxylase (C4H) is coded for by the polypeptides of SEQ ID NOS: 8 and 9 which are encoded for by the nucleic acids of SEQ ID NOS: 26 and 27, respectively.

Cinnamyl alcohol dehydrogenase (CAD) is coded for by the polypeptides of SEQ ID NOS: 10, 11 and 12 which are encoded for by the nucleic acids of SEQ ID NOS: 28, 29, and 30, respectively.

Caffeoyl-CoA 3-O-methyltransferase (CCoA-OMT) is coded for by the polypeptides of SEQ ID NOS: 13, 14, 15, and 74 which are encoded for by the nucleic acids of SEQ ID NOS: 31, 32, 33, and 77, respectively.

Cinnamoyl-CoA reductase (CCR) is coded for by the polypeptides of SEQ ID NO: 16 which is encoded for by the nucleic acid of SEQ ID NO: 34.

A partial sequence for ferulate-5-hydroxylase (F5H) is coded for by the polypeptide of SEQ ID NO: 17 which is encoded for by the nucleic acid of SEQ ID NO: 35.

A partial sequence for diphenyl oxidase (DPO) is coded for by the polypeptides of SEQ ID NO: 18 which is encoded for by the nucleic acid of SEQ ID NO:36.

Ferulate-5-hydroxylase (F5H) is coded for by the polypeptide of SEQ ID NO: 73 which is encoded for by the nucleic acid of SEQ ID NO: 76.

Diphenyl oxidase (DPO) is coded for by the polypeptide of SEQ ID NO: 75 which is encoded for by the nucleic acid of SEQ ID NO:78.

B. Polynucleotides Amplified from a *Zea mays* Nucleic Acid Library

As indicated in (b), supra, the present invention provides isolated nucleic acids comprising lignin biosynthesis polynucleotides, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. Generally, a cDNA nucleic acid library will be constructed to comprise a majority of full-length cDNAs. Often, cDNA libraries will be normalized to increase the representation of relatively rare cDNAs. In preferred embodiments, the cDNA library is constructed mature lignified tissue such as root, leaf, or tassel tissue. The cDNA library can be constructed using a full-length cDNA synthesis method. Examples of such methods include Oligo-Capping (Maruyama, K. and Sugano, S. Gene 138: 171–174, 1994), Biotinylated CAP Trapper (Carninci, P., Kvan, C., et al. Genomics 37: 327–336, 1996), and CAP Retention Procedure (Edery, E., Chu, L. L., et al. Molecular and Cellular Biology 15: 3363–3371, 1995). cDNA synthesis is preferably catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as mRNA sources.

The polynucleotides of the present invention include those amplified using the following primer pairs:

SEQ ID NOS: 37 and 38 which yield an amplicon comprising a sequence having substantial identity to SEQ ID NO:19;

SEQ ID NOS: 39 and 40 which yield an amplicon comprising a sequence having substantial identity to SEQ ID NO:20;

SEQ ID NOS: 41 and 42 which yield an amplicon comprising a sequence having substantial identity to SEQ ID NO:21;

SEQ ID NOS: 43 and 44 which yield an amplicon comprising a sequence having substantial identity to SEQ ID NO:22;

SEQ ID NOS: 45 and 46 which yield an amplicon comprising a sequence having substantial identity to SEQ ID NO:23;
SEQ ID NOS: 47 and 48 which yield an amplicon comprising a sequence having substantial identity to SEQ ID NO:24;
SEQ ID NOS: 49 and 50 which yield an amplicon comprising a sequence having substantial identity to SEQ ID NO:25;
SEQ ID NOS: 51 and 52 which yield an amplicon comprising a sequence having substantial identity to SEQ ID NO:26;
SEQ ID NOS: 53 and 54 which yield an amplicon comprising a sequence having substantial identity to SEQ ID NO:27;
SEQ ID NOS: 55 and 56 which yield an amplicon comprising a sequence having substantial identity to SEQ ID NO:28;
SEQ ID NOS: 57 and 58 which yield an amplicon comprising a sequence having substantial identity to SEQ ID NO:29;
SEQ ID NOS: 59 and 60 which yield an amplicon comprising a sequence having substantial identity to SEQ ID NO:30;
SEQ ID NOS: 61 and 62 which yield an amplicon comprising a sequence having substantial identity to SEQ ID NO:31;
SEQ ID NOS: 63 and 64 which yield an amplicon comprising a sequence having substantial identity to SEQ ID NO:32;
SEQ ID NOS: 65 and 66 which yield an amplicon comprising a sequence having substantial identity to SEQ ID NO:33;
SEQ ID NOS: 67 and 68 which yield an amplicon comprising a sequence having substantial identity to SEQ ID NO:34;
SEQ ID NOS: 69 and 70 which yield an amplicon comprising a sequence having substantial identity to SEQ ID NO:35;
SEQ ID NOS: 71 and 72 which yield an amplicon comprising a sequence having substantial identity to SEQ ID NO:36.
SEQ ID NOS: 79 and 80 which yield an amplicon comprising a sequence having substantial identity to SEQ ID NO:76.
SEQ ID NOS: 81 and 82 which yield an amplicon comprising a sequence having substantial identity to SEQ ID NO:77.
SEQ ID NOS: 83 and 84 which yield an amplicon comprising a sequence having substantial identity to SEQ ID NO:78.

The present invention also provides subsequences of full-length nucleic acids. Any number of subsequences can be obtained by reference to SEQ ID NOS: 19–36 and 76–78, and using primers which selectively amplify, under stringent conditions to: at least two sites to the polynucleotides of the present invention, or to two sites within the nucleic acid which flank and comprise a polynucleotide of the present invention, or to a site within a polynucleotide of the present invention and a site within the nucleic acid which comprises it. A variety of methods for obtaining 5' and/or 3' ends is well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28–38.); see also, U.S. Pat. No. 5,470,722, and *Current Protocols in Molecular Biology*, Unit 15.6, Ausubel, et al., Eds., Greene Publishing and Wiley-Interscience, New York (1995). Thus, the present invention provides lignin biosynthesis polynucleotides having the sequence of the lignin biosynthesis gene, nuclear transcript, cDNA, or complementary sequences and/or subsequences thereof.

Primer sequences can be obtained by reference to a contiguous subsequence of a polynucleotide of the present invention. Primers are chosen to selectively hybridize, under PCR amplification conditions, to a polynucleotide of the present invention in an amplification mixture comprising a genomic and/or cDNA library from the same species. Generally, the primers are complementary to a subsequence of the amplicon they yield. In some embodiments, the primers will be constructed to anneal at their 5' terminal end's to the codon encoding the carboxy or amino terminal amino acid residue (or the complements thereof) of the polynucleotides of the present invention. The primer length in nucleotides is selected from the group of integers consisting of from at least 15 to 50. Thus, the primers can be at least 15, 18, 20, 25, 30, 40, or 50 nucleotides in length. A non-annealing sequence at the 5'end of the primer (a "tail") can be added, for example, to introduce a cloning site at the terminal ends of the amplicon.

The amplification primers may optionally be elongated in the 3' direction with additional contiguous nucleotides from the polynucleotide sequences, such as SEQ ID NOS: 19–36 and 76–78, from which they are derived. The number of nucleotides by which the primers can be elongated is selected from the group of integers consisting of from at least 1 to 25. Thus, for example, the primers can be elongated with an additional 1, 5, 10, or 15 nucleotides. Those of skill will recognize that a lengthened primer sequence can be employed to increase specificity of binding (i.e., annealing) to a target sequence.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p. 354.

C. Polynucleotides Which Selectively Hybridize to a Polynucleotide of (A) or (B)

As indicated in (c), supra, the present invention provides isolated nucleic acids comprising lignin biosynthesis polynucleotides, wherein the polynucleotides selectively hybridize, under selective hybridization conditions, to a polynucleotide of paragraphs (A) or (B) as discussed, supra. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated from a *Zea mays* nucleic acid library. Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having at Least 60% Sequence Identity with the Polynucleotides of (A), (B) or (C)

As indicated in (d), supra, the present invention provides isolated nucleic acids comprising lignin biosynthesis polynucleotides, wherein the polynucleotides have a specified identity at the nucleotide level to a polynucleotide as disclosed above in paragraphs (A), (B), or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will share an epitope with a polypeptide encoded by the polynucleotides of (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Ser. Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), supra, the present invention provides isolated nucleic acids comprising lignin biosynthesis polynucleotides, wherein the polynucleotides encode a protein having a subsequence of contiguous amino acids from a prototype lignin biosynthesis polypeptide. Exemplary prototype lignin biosynthesis polypeptides are provided in SEQ ID NOS: 1–18 and 73–75. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as, but not limited to, a polypeptide encoded by the polynucleotide of (b), supra, or exemplary polypeptides of SEQ ID NOS: 1–18 and 73–75. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated lignin biosynthesis polypeptides as disclosed herein (e.g., SEQ ID NOS: 1–18 and 73–75). Molecular weight can be readily determined by SDS-PAGE under reducing conditions. Preferably, the molecular weight is within 15% of a full length lignin biosynthesis polypeptide, more preferably within 10% or 5%, and most preferably within 3%, 2%, or 1% of a full length lignin biosynthesis polypeptide of the present invention. Molecular weight determination of a protein can be conveniently performed by SDS-PAGE under denaturing conditions.

Optionally, the polynucleotides of this embodiment will encode a protein having a specific activity at least 20%, 30%, 40%, or 50% of the native, endogenous (i.e., non-isolated), full-length lignin biosynthesis polypeptide. Further, the proteins encoded by polynucleotides of this embodiment will optionally have a substantially similar apparent dissociation constant ($K_m$) and/or catalytic activity (i.e., the microscopic rate constant, $k_{cat}$) as the native endogenous, full-length lignin biosynthesis protein. Those of skill in the art will recognize that $k_{cat}/K_m$ value determines the specificity for competing substrates and is often referred to as the specificity constant. Proteins of this embodiment can have a $k_{cat}/K_m$ value at least 10% of the non-isolated full-length lignin biosynthesis polypeptide as determined using the substrate of that polypeptide from the lignin biosynthesis specific pathways, supra. Optionally, the $k_{cat}/K_m$ value will be at least 20%, 30%, 40%, 50%, and most preferably at least 60%, 70%, 80%, 90%, or 95% the $k_{cat}/K_m$ value of the non-isolated, full-length lignin biosynthesis polypeptide. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), supra, the present invention provides isolated nucleic acids comprising lignin biosynthesis polynucleotides, wherein the polynucleotides are complementary to the polynucleotides of paragraphs A–E, above. As those of skill in the art will recognize, complementary sequences base-pair throughout the entirety of their length with the polynucleotides of (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), supra, the present invention provides isolated nucleic acids comprising lignin biosynthesis polynucleotides, wherein the polynucleotide comprises at least 15 contiguous bases from the polynucleotides of (A) through (F) as discussed above. The length of the polynucleotide is given as an integer selected from the group consisting of from at least 15 to the length of the nucleic acid sequence of which the polynucleotide is a subsequence. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype sequence, such as SEQ ID NOS: 1–18 and 73–75, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays. Particularly preferred is the use of Zea mays tissue from root, leaf, or tassel.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adaptors, and linkers is well known in the art. Exemplary nucleic acids include such vectors as: M13, lambda ZAP Express, lambda ZAP II, lambda gt10, lambda gt11, pBK-CMV, PBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pOPRSVI CAT, pOP13 CAT, pXT1, pSG5, pPbac, pMbac, pMClneo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)+ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)+ mRNA template using a poly(dT) primer or random hexanucleotides. Second, the resultant RNA-DNA hybrid is converted into double stranded cDNA, typically by a combination of RNAse H and DNA polymerase I (or Klenow fragment). Third, the termini of the double stranded cDNA are ligated to adaptors. Ligation of the adaptors will produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as: Stratagene, and Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*,15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique,* 3(2):58–63 (1991); Sive and St. John, *Nucl. Acids Res.,* 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8):1954 (1991). cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *Bio Techniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, supra.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter lignin biosynthesis content and/or composition in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a lignin biosynthesis gene so as to control the expression of the gene. Gene expression can be modulated under conditions suitable for plant growth so as to alter lignin biosynthesis content and/or composition. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114–115, Freeling and Walbot, Eds., Springer, N.Y. (1994); *Corn and Corn Improvement*, 3$^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, N.Y., (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221–227 1983. In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the anti-sense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci.* (USA) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672, 593; 5,484,908; 5,256,648; and, 5,681,941.

Proteins

The isolated proteins of the present invention comprise a polypeptide having at least 10 amino acids encoded by any one of the polynucleotides of the present invention as discussed more fully, supra, or polypeptides which are conservatively modified variants thereof. Exemplary polypeptide sequences are provided in SEQ ID NOS: 1–18 and 73–75. The proteins of the present invention or variants thereof can comprise any number of contiguous amino acid residues from a polypeptide of the present invention, wherein that number is selected from the group of integers consisting of from 10 to the number of residues in a full-length lignin biosynthesis polypeptide. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention encoded by a polynucleotide of the present invention as described, supra. Exemplary polypeptides include those which are full-length, such as those disclosed in SEQ ID NOS: 1–18 and 73–75. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al, *Methods in Yeast Genetics*, Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8: 17–24 (1979); Broach, et al., *Gene* 8: 121–133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A. Plant Transformation

A DNA sequence coding for the desired polynucleotide of the present invention, for example a cDNA or a genomic sequence encoding a full length protein, will be used to construct a recombinant expression cassette which can be introduced into the desired plant.

Isolated nucleic acid acids of the present invention can be introduced into plants according techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22: 421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

The introduction of DNA constructs using polyethylene glycol precipitation is described in Paszkowski et al., *Embo J.* 3: 2717–2722 (1984). Electroporation techniques are described in Fromm et al., *Proc. Natl. Acad. Sci.* 82: 5824 (1985). Ballistic transformation techniques are described in Klein et al., *Nature* 327: 70–73 (1987).

*Agrobacterium tumefaciens*-meditated transformation techniques are well described in the scientific literature. See, for example Horsch et al., *Science* 233: 496–498 (1984), and Fraley et al., *Proc. Natl. Acad. Sci.* 80:4803 (1983). Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985),Application PCT/US87/02512 (WO 88/02405 published Apr. 7,1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25: 1353, 1984), (3) the vortexing method (see, e.g., Kindle, *Proc. Natl. Acad. Sci., USA* 87: 1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding genes can be obtained by injection of the DNA into reproductive organs of a plant as described by Pena et al., Nature, 325.:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J.,

*Biochemical Methods in Cell Culture and Virology,* Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis*, Part A.; Merrifield, et al., *J. Am. Chem. Soc.* 85: 2149–2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: N.Y. (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement,* $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype, (e.g., altered lignin biosynthesis content or composition).

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered lignification relative to a control plant (i.e., native, non-transgenic). Back-crossing to a parental plant and out-crossing with a non- transgenic plant are also contemplated.

Modulating Lignin Biosynthesis Content and/or Composition

The present invention further provides a method for modulating (i.e., increasing or decreasing) lignin biosynthesis content or composition in a plant or part thereof. Modulation can be effected by increasing or decreasing the lignin biosynthesis content (i.e., the total amount of lignin biosynthesis) and/or the lignin biosynthesis composition (the ratio of various lignin biosynthesis monomers in the plant) in a plant. The method comprises transforming a plant cell with a recombinant expression cassette comprising a polynucleotide of the present invention as described above to obtain a transformed plant cell, growing the transformed plant cell under plant forming conditions, and inducing expression of a polynucleotide of the present invention in the plant for a time sufficient to modulate lignin biosynthesis content and/or composition in the plant or plant part.

In some embodiments, lignification in a plant may be modulated by altering, in vivo or in vitro, the promoter of a non-isolated lignin biosynthesis gene to up- or down-regulate gene expression. In some embodiments, the coding regions of native lignin biosynthesis genes can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate lignin biosynthesis content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, lignification is modulated in monocots, particularly maize.

Molecular Markers

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a lignin biosynthesis gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a lignin biosynthesis gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table 1, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.*15:8125 (1987)) and the 5<G>7 methyl GppppG cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J.-H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an increased $K_m$ and/or $K_{cat}$ over the wild-type protein as provided herein. In other embodiments, a protein or polyculeotide generated from sequence shuffling will have a ligand binding affinity greater than the non-shuffled wild-type polynucleotide. The increase in such properties can be at least 110%, 120%, 130%, 140% or at least 150% of the wild-type value.

Detection of Nucleic Acids

The present invention further provides methods for detecting a polynucleotide of the present invention in a nucleic acid sample suspected of comprising a polynucleotide of the present invention, such as a plant cell lysate, particularly a lysate of corn. In some embodiments, a lignin biosynthesis gene or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-lignin biosynthesis genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3): 230–250 (1986); Haase et al., *Methods in Virology*, Vol. VII, pp. 189–226 (1984); Wilkinson, The theory and practice of in situ hybridization in: *In situ Hybridization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radio-active isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K., *A Colorimetric Method for DNA Hybridization*, Nucl. Acids Res. 12: 3435–3444 (1984)) and synthetic oligonucleotides have been coupled directly with alkaline phosphatase (Jablonski, E., et al., *Preparation of Oligodeoxynucleotide-Alkaline Phosphatase Conjugates and Their Use as Hybridization Probes*, Nuc. Acids. Res. 14: 6115–6128 (1986); and Li P., et al., *Enzyme-linked Synthetic Oligonucleotide probes: Non-Radioactive Detection of Enterotoxigenic Escherichia Coli in Faeca Specimens*, Nucl. Acids Res. 15: 5275–5287 (1987)).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native lignin biosynthesis protein of 5 amino acids in length or greater and selected from a protein encoded by a polynucleotide of the present invention, such as exemplary sequences of SEQ ID NOS: 1–18 and 73–75, are the preferred immunogens (antigen) for the production of monoclonal or polyclonal antibodies. Those of skill will readily understand that the proteins of the present invention are typically denatured, and optionally reduced, prior to formation of antibodies for screening expression libraries or other assays in which a putative protein of the present invention is expressed or denatured in a non-native secondary, tertiary, or quarternary structure. Naturally occurring lignin biosynthesis polypeptides can be used either in pure or impure form.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology*, Wiley/Greene, New York (1991); and Harlow and Lane, *Antibodies: A Laboratory Manual*, Cold Spring Harbor Press, New York (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a protein from which the immunogen was derived. Specific monoclonal and polyclonal antibodies will usually have an antibody binding site with an affinity constant for its cognate monovalent antigen at least between $10^6$–$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256: 495–497 (1975). Summarized briefly, this method proceeds by injecting an animal with an immunogen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of recombinant antibodies in phage or similar vectors (see, e.g., Huse et al., *Science* 246: 1275–1281 (1989); and Ward, et al., *Nature* 341: 544–546 (1989); and Vaughan et al., *Nature Biotechnology*, 14: 309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14: 845–851 (1996). Also, recombinant immunoglobulins may be produced. See, Cabilly, U.S. Pat. No. 4,816,567; and Queen et al., *Proc. Nat'l Acad. Sci.* 86: 10029–10033 (1989).

The antibodies of this invention are also used for affinity chromatography in isolating proteins of the present invention. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Protein Immunoassays

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassaysm*, Price and Newman Eds., Stockton Press, New York (1991); and *Non-isotopic Immunoassays*, Ngo, Ed., Plenum Press, New York (1988). Immunological binding assays (or immunoassays) typically utilize a "capture agent" to specifically bind to and often immobilize the analyte (in this case, a protein of the present invention). The capture agent is a moiety that specifically binds to the analyte. In a preferred embodiment, the capture agent is an antibody that specifically binds a protein(s) of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (See, generally Kronval, et al., *J. Immunol.* 111: 1401–1406 (1973), and Akerstrom, et al., *J. Immunol.* 135: 2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Non-competitive immunoassays are assays in which the amount of captured analyte (i.e., a protein of the present invention) is directly measured. In one preferred "sandwich" assay, for example, the capture agent (e.g., an antibody specifically reactive, under immunoreactive conditions, to a protein of the present invention) can be bound directly to a solid substrate where they are immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In a particularly preferred embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another preferred competitive assay. In this assay a known analyte, (such as a protein of the present invention) is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Generation of Pooled Antisera for Use in Immunoassays

A protein that specifically binds to or that is specifically immunoreactive with an antibody generated against a defined immunogen, such as an immunogen consisting of the amino acid sequence of SEQ ID NOS: 1–18 and 73–75, is determined in an immunoassay. The immunoassay uses a polyclonal antiserum which is raised to a polypeptide of the present invention (i.e., the immunogenic polypeptide). This antiserum is selected to have low crossreactivity against other proteins and any such crossreactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide (e.g., SEQ ID NOS: 1–18 and 73–75) is isolated as described herein. For example, recombinant protein can be produced in a mammalian or other eukaryotic cell line. An inbred strain of mice is immunized with the protein of using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570–573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In a particularly preferred embodiment, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and calorimetric labels or colored glass or plastic beads, as discussed for nucleic acid labels, supra.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length lignin biosynthesis polypeptide (e.g., enzyme). Generally, the polypeptide will be present in a range sufficient to determine the effect of the compound, typically about 1 nM to 10 µM. Likewise, the compound will be present in a concentration of from about 1 nM to 10 µM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics are well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLE 1

This example describes the construction of cDNA libraries.

Total RNA Isolation

Total RNA was isolated from corn tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adaptors were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 $cm^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 $cm^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook,J., Fritsch, E. F. and Maniatis, T., (in Molecular Cloning: A laboratory Manual, $2^{nd}$ Edition). The following probes were used in colony hybridization:
1. First strand cDNA from the same tissue as the library was made from to remove the most redundant clones.
2. 48–192 most redundant cDNA clones from the same library based on previous sequencing data.
3. 192 most redundant cDNA clones from previous sequencing in corn.
4. A Sal-A20 oligo nucleotide: TCG ACC CAC GCG TCC GAA AAA AAA AAA AAA AAA AAA, SEQ ID NO.: 85, removes clones containing a poly A tail but no cDNA.
5. cDNA clones derived from rRNA.

The image of the autoradiography was scanned into computer and the signal intensity and cold colony addresses of each colony were analyzed. Rearraying of cold-colonies from 384 well plates to 96 well plates was conducted using Q-bot.

EXAMPLE b 3

This example describes the tissue and tissue treatment used for construction of cDNA libraries.

The polynucleotide having the DNA sequences given in SEQ ID NOS:19–36 were obtained from the sequencing of a library of cDNA clones prepared from maize. The library from which SEQ ID NO:19 was obtained was constructed from premeiotic to uninucleate tassel from line A632. The library from which SEQ ID NO:20 was obtained was constructed from a shoot culture from the maize line Crusader. The library from which SEQ ID NO:21 was obtained was constructed from immature ear of line AP9. The library from which SEQ ID NO:22 was obtained was constructed from tissue culture during induced apoptosis of line BMS-P2#10. The library from which SEQ ID NO:23 was obtained was constructed from premeiotic to uninucleate tassel from line A632. The library from which SEQ ID NO:24 was obtained was constructed from early meiotic tassel (16–18 mm). The library from which SEQ ID NO:25 was obtained was constructed from corn root worm infested roots of line B73. The library from which SEQ ID NO:26 was obtained was constructed from immature ear of line AP9. The library from which SEQ ID NO:27 was obtained was constructed from scutellar node of germinating maize seeds of line B73. The library from which SEQ ID NO:28 was obtained was constructed from B73 embryo 13 days after pollination. The library from which SEQ ID NO:29 was obtained was constructed from 8-hour heat shock recovery B73 seedling. The library from which SEQ ID NO:30 was obtained was constructed from corn root worm infested roots of line B73. The library from which SEQ ID NO:31 was obtained was constructed from shoot culture of line CM45. The library from which SEQ ID NO:32 was obtained was constructed from 8-hour heat shock recovery B73 seedling. The library from which SEQ ID NO:33 was obtained was constructed from root tips (less than 5mm in length) of B73. The library from which SEQ ID NO:34 was obtained was constructed from green leaves of B73 treated with jasmonic acid. The library from which SEQ ID NO:35 was obtained was constructed from green leaves of B73. The library from which SEQ ID NO:36 was obtained was constructed from immature ear of inbred B73. The library from which SEQ ID NO:76 was obtained was constructed from ear leaf collar tissue after pollen shed from inbred B73. The library from which SEQ ID NO:77 was obtained was constructed from leaf collars for the ear leaf of inbred B73. The library was subject to a subtraction procedure as described in Example 2. The library from which SEQ ID NO:78 was obtained was constructed from a 7-cm section of the whorl from B73 that had been previously infected with European corn borer ($1^{st}$ brood) at the V9 (nine node stage, vegetative growth) stage of development.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated polynucleotide encoding a lignin biosynthetic enzyme cinnamate-4-hydroxylase, wherein said encoded enzyme is functional in *Zea mays* and wherein said polynucleotide comprises SEQ ID NO: 26.

2. A recombinant expression cassette, comprising the polynucleotide of claim 1 operably linked to a promoter.

3. An isolated host cell comprising the recombinant expression cassette of claim 2.

4. The host cell of claim 3, wherein said host cell is a sorghum (*Sorghum bicolor*) or maize (*Zea mays*) cell.

5. A transgenic plant comprising a recombinant expression cassette comprising a plant promoter operably linked to the isolated polynucleotide of claim 1.

6. The transgenic plant of claim 5, wherein said plant is *Zea mays*.

7. A transgenic seed comprising a recombinant expression cassette comprising a plant promoter operably linked to the isolated polynucleotide of claim 1.

8. The transgenic seed of claim 7, wherein the seed is from *Zea mays*.

9. An isolated polynucleotide encoding a lignin biosynthetic enzyme cinnamate-4-hydroxylase, wherein said encoded enzyme is functional in *Zea mays* and wherein said polynucleotide encodes the polypeptide of SEQ ID NO: 8.

* * * * *